(12) United States Patent
Burns et al.

(10) Patent No.: US 11,564,833 B2
(45) Date of Patent: Jan. 31, 2023

(54) PUNCTAL IMPLANTS WITH CONTROLLED DRUG DELIVERY FEATURES AND METHODS OF USING SAME

(71) Applicant: GLAUKOS CORPORATION, San Clemente, CA (US)

(72) Inventors: Thomas W. Burns, Dana Point, CA (US); Douglas Daniel Crimaldi, San Marcos, CA (US); David Applegate, Palm Springs, CA (US); Kenneth Martin Curry, Oceanside, CA (US)

(73) Assignee: GLAUKOS CORPORATION, San Clemente, CA (US)

( * ) Notice: Subject to any disclaimer, the term of this patent is extended or adjusted under 35 U.S.C. 154(b) by 366 days.

(21) Appl. No.: 15/762,969

(22) PCT Filed: Sep. 23, 2016

(86) PCT No.: PCT/US2016/053570
§ 371 (c)(1),
(2) Date: Mar. 23, 2018

(87) PCT Pub. No.: WO2017/053885
PCT Pub. Date: Mar. 30, 2017

(65) Prior Publication Data
US 2019/0083307 A1    Mar. 21, 2019

Related U.S. Application Data

(60) Provisional application No. 62/233,259, filed on Sep. 25, 2015.

(51) Int. Cl.
*A61F 9/00* (2006.01)
*A61K 31/56* (2006.01)
(Continued)

(52) U.S. Cl.
CPC ........ *A61F 9/0017* (2013.01); *A61F 9/00772* (2013.01); *A61K 31/56* (2013.01);
(Continued)

(58) Field of Classification Search
CPC .................................................. A61F 9/00772
See application file for complete search history.

(56) References Cited

U.S. PATENT DOCUMENTS 663,670 A    12/1900   Wiswall
3,416,530 A  12/1968   Ness
(Continued)

FOREIGN PATENT DOCUMENTS

AU    2004264913    12/2011
CA    2442652       1/2011
(Continued)

OTHER PUBLICATIONS

US 7,524,280 B2, 04/2009, Connors et al. (withdrawn)
(Continued)

*Primary Examiner* — Catharine L Anderson
*Assistant Examiner* — Arjuna P Chatrathi
(74) *Attorney, Agent, or Firm* — Knobbe, Martens, Olson & Bear, LLP

(57) ABSTRACT

Disclosed herein are drug delivery punctal implants and methods of using the implants for the treatment of ocular disorders requiring targeted and controlled administration of a drug to an interior portion of the eye for reduction or prevention of symptoms of the disorder. The physical arrangement of drugs within the punctal plugs disclosed herein results, in several embodiments, in advantageous controlled delivery of one or more drugs to the eye of a patient.

17 Claims, 23 Drawing Sheets

(51) Int. Cl.
*A61K 31/573* (2006.01)
*A61K 31/58* (2006.01)
*A61K 38/13* (2006.01)
*A61F 9/007* (2006.01)

(52) U.S. Cl.
CPC ............ *A61K 31/573* (2013.01); *A61K 31/58* (2013.01); *A61K 38/13* (2013.01); *A61F 2210/0004* (2013.01); *A61F 2210/0014* (2013.01); *A61F 2220/0008* (2013.01); *A61F 2220/0016* (2013.01); *A61F 2250/0068* (2013.01)

(56) References Cited

U.S. PATENT DOCUMENTS

| | | | |
|---|---|---|---|
| 3,710,795 A | 1/1973 | Higuchi et al. | |
| 3,949,750 A | 4/1976 | Freeman | |
| 3,961,628 A | 6/1976 | Arnold | |
| 4,034,756 A | 7/1977 | Higuchi et al. | |
| 4,093,708 A | 6/1978 | Zaffaroni et al. | |
| 4,113,088 A | 9/1978 | Binkhorst | |
| 4,207,890 A | 6/1980 | Mamajek et al. | |
| 4,328,803 A | 5/1982 | Pape | |
| 4,450,150 A | 5/1984 | Sidman | |
| 4,521,210 A | 6/1985 | Wong | |
| 4,736,836 A | 4/1988 | Along et al. | |
| 4,743,248 A | 5/1988 | Bartoo et al. | |
| 4,846,793 A | 7/1989 | Leonard et al. | |
| 4,853,224 A | 8/1989 | Wong | |
| 4,863,457 A | 9/1989 | Lee | |
| 4,878,905 A | 11/1989 | Blass | |
| 4,883,864 A | 11/1989 | Scholz | |
| 4,955,881 A | 9/1990 | Eckenhoff | |
| 4,997,652 A | 3/1991 | Wong | |
| 5,017,381 A * | 5/1991 | Maruyama ............ A61K 9/0004 424/472 | |
| 5,098,443 A | 3/1992 | Parel et al. | |
| 5,128,145 A | 7/1992 | Edgren et al. | |
| 5,164,188 A | 11/1992 | Wong | |
| 5,324,280 A | 6/1994 | Wong et al. | |
| 5,334,137 A * | 8/1994 | Freeman ............ A61B 17/12022 604/244 | |
| 5,364,374 A | 11/1994 | Morrison et al. | |
| 5,378,474 A | 1/1995 | Morelia et al. | |
| 5,378,475 A | 1/1995 | Smith et al. | |
| 5,384,333 A | 1/1995 | Davis et al. | |
| 5,443,505 A | 8/1995 | Wong et al. | |
| 5,464,450 A | 11/1995 | Buscemi et al. | |
| 5,466,233 A | 11/1995 | Weiner et al. | |
| 5,500,465 A | 3/1996 | Krishnan et al. | |
| 5,502,052 A | 3/1996 | DeSantis | |
| 5,516,522 A | 5/1996 | Peyman et al. | |
| 5,547,993 A | 8/1996 | Miki | |
| 5,599,534 A | 2/1997 | Himmelstein et al. | |
| 5,629,008 A | 5/1997 | Lee | |
| 5,645,856 A | 7/1997 | Lacy et al. | |
| 5,652,014 A | 7/1997 | Galin et al. | |
| 5,652,236 A | 7/1997 | Krauss | |
| 5,663,205 A | 9/1997 | Ogawa et al. | |
| 5,665,114 A | 9/1997 | Weadock et al. | |
| 5,670,161 A | 9/1997 | Healy et al. | |
| 5,686,425 A | 11/1997 | Lee | |
| 5,709,854 A | 1/1998 | Griffith-Cima et al. | |
| 5,725,493 A | 3/1998 | Avery et al. | |
| 5,733,327 A | 3/1998 | Igaki et al. | |
| 5,766,242 A | 6/1998 | Wong et al. | |
| 5,767,079 A | 6/1998 | Glaser et al. | |
| 5,773,019 A | 6/1998 | Ashton et al. | |
| 5,814,620 A | 9/1998 | Robinson et al. | |
| 5,824,072 A | 10/1998 | Wong | |
| 5,869,079 A | 2/1999 | Wong et al. | |
| 5,869,468 A | 2/1999 | Freeman | |
| 5,891,084 A | 4/1999 | Lee | |
| 5,902,598 A | 5/1999 | Chen et al. | |
| 5,925,342 A | 7/1999 | Adorante et al. | |
| 5,952,378 A | 9/1999 | Stjerschantz et al. | |
| 5,980,928 A | 11/1999 | Terry | |
| 5,981,598 A | 11/1999 | Tatton | |
| 6,004,302 A | 12/1999 | Brierley | |
| 6,007,511 A | 12/1999 | Prywes | |
| 6,059,812 A | 5/2000 | Clerc et al. | |
| 6,060,463 A | 5/2000 | Freeman | |
| 6,063,116 A | 5/2000 | Kelleher | |
| 6,063,396 A | 5/2000 | Kelleher | |
| 6,110,912 A | 8/2000 | Kaufman et al. | |
| 6,129,761 A | 10/2000 | Hubbell | |
| 6,159,458 A | 12/2000 | Bowman et al. | |
| 6,196,993 B1 * | 3/2001 | Cohan ................... A61F 9/0017 604/93.01 | |
| 6,228,873 B1 | 5/2001 | Brandt et al. | |
| 6,231,600 B1 | 5/2001 | Zhong | |
| 6,231,853 B1 | 5/2001 | Hillman et al. | |
| 6,248,363 B1 | 6/2001 | Patel et al. | |
| 6,251,090 B1 | 6/2001 | Avery et al. | |
| 6,268,398 B1 | 7/2001 | Ghosh et al. | |
| 6,274,138 B1 | 8/2001 | Bandman et al. | |
| 6,290,684 B1 * | 9/2001 | Herrick ............... A61F 9/00772 128/887 | |
| 6,299,895 B1 | 10/2001 | Hammang et al. | |
| 6,306,120 B1 | 10/2001 | Tan | |
| 6,331,313 B1 | 12/2001 | Wong et al. | |
| 6,348,042 B1 | 2/2002 | Warren, Jr. | |
| 6,369,116 B1 | 4/2002 | Wong et al. | |
| 6,375,972 B1 | 4/2002 | Guo et al. | |
| 6,378,526 B1 | 4/2002 | Bowman | |
| 6,397,849 B1 | 6/2002 | Bowman et al. | |
| 6,413,245 B1 | 7/2002 | Yaacobi et al. | |
| 6,416,777 B1 | 7/2002 | Yaacobi | |
| 6,423,001 B1 | 7/2002 | Abreu | |
| 6,436,427 B1 | 8/2002 | Hammang et al. | |
| 6,450,984 B1 | 9/2002 | Lynch et al. | |
| 6,454,787 B1 | 9/2002 | Maddalo et al. | |
| 6,455,062 B1 | 9/2002 | Olejnik et al. | |
| 6,464,724 B1 | 10/2002 | Lynch et al. | |
| 6,503,231 B1 | 1/2003 | Prausnitz et al. | |
| 6,506,411 B2 | 1/2003 | Hunter et al. | |
| 6,524,275 B1 | 2/2003 | Lynch et al. | |
| 6,533,769 B2 | 3/2003 | Homen | |
| 6,548,078 B2 | 4/2003 | Guo et al. | |
| 6,551,618 B2 | 4/2003 | Baird et al. | |
| 6,562,374 B1 | 5/2003 | Han et al. | |
| 6,576,219 B2 | 6/2003 | Brandt et al. | |
| 6,589,198 B1 | 7/2003 | Soltanpour et al. | |
| 6,626,858 B2 | 9/2003 | Lynch et al. | |
| 6,638,239 B1 | 10/2003 | Bergheim et al. | |
| 6,649,184 B2 | 11/2003 | Hammang et al. | |
| 6,656,490 B1 | 12/2003 | Steinemann et al. | |
| 6,660,870 B1 | 12/2003 | Ruskinko et al. | |
| 6,666,841 B2 | 12/2003 | Gharib et al. | |
| 6,682,500 B2 | 1/2004 | Soltanpour et al. | |
| 6,692,759 B1 | 2/2004 | Wong et al. | |
| 6,693,093 B2 | 2/2004 | Chowdhary et al. | |
| 6,699,493 B2 | 3/2004 | Wong | |
| 6,726,666 B2 | 4/2004 | de Juan, Jr. | |
| 6,726,918 B1 | 4/2004 | Wong et al. | |
| D490,152 S | 5/2004 | Myall et al. | |
| 6,730,056 B1 | 5/2004 | Ghaem et al. | |
| 6,736,791 B1 | 5/2004 | Tu et al. | |
| 6,758,837 B2 | 7/2004 | Peclat et al. | |
| 6,764,698 B1 | 7/2004 | Byun et al. | |
| 6,780,164 B2 | 8/2004 | Bergheim et al. | |
| 6,783,544 B2 | 8/2004 | Lynch et al. | |
| 6,827,699 B2 | 12/2004 | Lynch et al. | |
| 6,827,700 B2 | 12/2004 | Lynch et al. | |
| 6,939,298 B2 | 9/2005 | Brown et al. | |
| 6,955,656 B2 | 10/2005 | Bergheim et al. | |
| 6,981,958 B1 | 1/2006 | Gharib et al. | |
| 6,998,137 B2 | 2/2006 | Shih et al. | |
| 7,033,603 B2 | 4/2006 | Nelson et al. | |
| 7,048,946 B1 | 5/2006 | Wong et al. | |
| 7,083,802 B2 | 8/2006 | Peyman | |
| 7,094,225 B2 | 8/2006 | Tu et al. | |
| 7,094,226 B2 | 8/2006 | Yaacobi | |

(56) References Cited

U.S. PATENT DOCUMENTS

| | | |
|---|---|---|
| 7,101,567 B1 | 9/2006 | Sano et al. |
| 7,135,009 B2 | 11/2006 | Tu et al. |
| 7,163,543 B2 | 1/2007 | Smedley et al. |
| 7,182,747 B2 | 2/2007 | Kwon |
| 7,186,232 B1 | 3/2007 | Smedley et al. |
| 7,192,412 B1 | 3/2007 | Zhou et al. |
| 7,195,774 B2 | 3/2007 | Carvalho et al. |
| 7,220,238 B2 | 5/2007 | Lynch et al. |
| 7,226,435 B2 | 6/2007 | Darnell |
| 7,261,529 B2 | 8/2007 | Persyn et al. |
| 7,273,475 B2 | 9/2007 | Tu et al. |
| 7,297,130 B2 | 11/2007 | Bergheim et al. |
| 7,402,156 B2 | 7/2008 | Kiehlbauch et al. |
| 7,431,710 B2 | 10/2008 | Tu et al. |
| 7,458,953 B2 | 12/2008 | Peyman |
| 7,488,303 B1 | 2/2009 | Haffner et al. |
| 7,494,487 B2 | 2/2009 | Timm |
| 7,496,174 B2 | 2/2009 | Gertner et al. |
| 7,513,893 B2 | 4/2009 | Soroudi |
| 7,563,241 B2 | 7/2009 | Tu et al. |
| 7,563,255 B2 | 7/2009 | Adamis et al. |
| 7,585,517 B2 | 9/2009 | Cooper et al. |
| 7,592,016 B2 | 9/2009 | Wong et al. |
| 7,638,137 B2 | 11/2009 | Rathjen et al. |
| 7,678,065 B2 | 3/2010 | Haffner et al. |
| 7,678,078 B1 | 3/2010 | Peyman et al. |
| 7,680,244 B2 | 3/2010 | Gertner et al. |
| 7,680,245 B2 | 3/2010 | Gertner |
| 7,697,663 B2 | 4/2010 | Gertner |
| 7,708,711 B2 | 5/2010 | Tu et al. |
| 7,709,049 B2 | 5/2010 | Chappa |
| 7,749,528 B2 | 7/2010 | DeCarvalho et al. |
| 7,776,024 B2 | 8/2010 | Santini et al. |
| 7,794,751 B2 | 9/2010 | Chudzik et al. |
| 7,811,252 B2 | 10/2010 | Dacquay et al. |
| 7,822,175 B2 | 10/2010 | Gertner |
| 7,846,468 B2 | 12/2010 | Wong |
| 7,850,637 B2 | 12/2010 | Lynch et al. |
| 7,857,782 B2 | 12/2010 | Tu et al. |
| 7,867,186 B2 | 1/2011 | Haffner et al. |
| 7,867,205 B2 | 1/2011 | Bergheim et al. |
| 7,879,001 B2 | 2/2011 | Haffner et al. |
| 7,879,079 B2 | 2/2011 | Tu et al. |
| 7,887,517 B2 | 2/2011 | Santos et al. |
| 7,887,521 B2 | 2/2011 | Dacquey et al. |
| 7,951,155 B2 | 5/2011 | Smedley et al. |
| 7,953,203 B2 | 5/2011 | Gertner et al. |
| 7,958,840 B2 | 6/2011 | Chappa |
| 7,967,772 B2 | 6/2011 | McKenzie et al. |
| 7,978,819 B2 | 7/2011 | Gertner et al. |
| 7,985,415 B2 | 7/2011 | Giroux |
| 7,997,460 B2 | 8/2011 | Pardes et al. |
| 8,007,459 B2 | 8/2011 | Haffner et al. |
| D645,489 S | 9/2011 | Gille et al. |
| D645,490 S | 9/2011 | Gille et al. |
| 8,012,136 B2 | 9/2011 | Collins, Jr. et al. |
| 8,059,784 B2 | 11/2011 | Gertner |
| 8,060,211 B2 | 11/2011 | Greenberg et al. |
| 8,062,244 B2 | 11/2011 | Tu et al. |
| 8,062,657 B2 | 11/2011 | Edelman et al. |
| 8,070,290 B2 | 12/2011 | Gille et al. |
| 8,071,120 B2 | 12/2011 | Wong |
| 8,073,105 B2 | 12/2011 | Gertner et al. |
| 8,075,511 B2 | 12/2011 | Tu et al. |
| 8,118,768 B2 | 2/2012 | Tu et al. |
| 8,142,364 B2 | 3/2012 | Haffner et al. |
| 8,152,752 B2 | 4/2012 | Lynch et al. |
| 8,235,053 B2 | 8/2012 | Sanchez et al. |
| 8,241,656 B2 | 8/2012 | Chudzik et al. |
| 8,273,050 B2 | 9/2012 | Bergheim et al. |
| 8,273,366 B2 | 9/2012 | Chauhan et al. |
| 8,277,830 B2 | 10/2012 | De Juan, Jr. et al. |
| 8,282,593 B2 | 10/2012 | Dacey, Jr. et al. |
| 8,298,578 B2 | 10/2012 | De Juan, Jr. et al. |
| 8,333,726 B2 | 12/2012 | Rapaki et al. |
| 8,333,742 B2 | 12/2012 | Bergheim et al. |
| 8,337,445 B2 | 12/2012 | Tu et al. |
| 8,343,086 B2 | 1/2013 | Dacey, Jr. et al. |
| 8,348,877 B2 | 1/2013 | Tu et al. |
| 8,366,652 B2 | 2/2013 | Dacey et al. |
| 8,388,568 B2 | 3/2013 | Lynch et al. |
| 8,404,269 B2 | 3/2013 | Snyder et al. |
| 8,414,517 B2 | 4/2013 | Dacey, Jr. et al. |
| 8,414,518 B2 | 4/2013 | Schieber et al. |
| 8,425,929 B2 | 4/2013 | Huang et al. |
| 8,440,216 B2 | 5/2013 | Huang et al. |
| 8,444,589 B2 | 5/2013 | Silvestrini |
| 8,452,391 B2 | 5/2013 | Roy |
| 8,454,582 B2 | 6/2013 | deJuan et al. |
| 8,486,031 B2 | 7/2013 | Bogdan |
| 8,486,052 B2 | 7/2013 | Varner et al. |
| 8,506,515 B2 | 8/2013 | Burns et al. |
| 8,529,492 B2 | 9/2013 | Luke et al. |
| 8,579,846 B2 | 11/2013 | Tu et al. |
| 8,617,094 B2 | 12/2013 | Smedley et al. |
| 8,642,066 B2 | 2/2014 | Abe et al. |
| 8,656,958 B2 | 2/2014 | Unger et al. |
| 8,657,804 B2 | 2/2014 | Horne et al. |
| 8,771,217 B2 | 7/2014 | Lynch et al. |
| 8,801,648 B2 | 8/2014 | Bergheim et al. |
| 8,808,219 B2 | 8/2014 | Bergheim et al. |
| 8,814,820 B2 | 8/2014 | Bergheim et al. |
| 8,882,781 B2 | 11/2014 | Smedley et al. |
| 9,022,967 B2 | 5/2015 | Oliver et al. |
| 9,066,782 B2 | 6/2015 | Tu et al. |
| 9,155,654 B2 | 10/2015 | Tu et al. |
| 9,173,775 B2 | 11/2015 | Haffner et al. |
| 9,220,632 B2 | 12/2015 | Smedley et al. |
| 9,301,875 B2 | 4/2016 | Tu et al. |
| 9,492,320 B2 | 11/2016 | Lynch et al. |
| 9,554,940 B2 | 1/2017 | Haffner et al. |
| 9,561,131 B2 | 2/2017 | Tu et al. |
| 9,572,963 B2 | 2/2017 | Tu et al. |
| 9,585,789 B2 | 3/2017 | Silvestrini et al. |
| 9,592,151 B2 | 3/2017 | Rangel-Friedman et al. |
| 9,597,230 B2 | 3/2017 | Haffner et al. |
| 9,603,738 B2 | 3/2017 | Haffner et al. |
| 9,636,255 B2 | 5/2017 | Haffner et al. |
| 9,668,915 B2 | 6/2017 | Haffner et al. |
| 9,730,638 B2 | 8/2017 | Haffner et al. |
| 9,789,001 B2 | 10/2017 | Tu et al. |
| 9,827,143 B2 | 11/2017 | Lynch et al. |
| 9,962,290 B2 | 5/2018 | Burns et al. |
| 9,987,472 B2 | 6/2018 | Tu et al. |
| 9,993,368 B2 | 6/2018 | Bergheim et al. |
| D833,008 S | 11/2018 | Kalina, Jr. et al. |
| 10,188,551 B2 | 1/2019 | Rangel-Friedman et al. |
| 10,206,813 B2 | 2/2019 | Haffner et al. |
| D846,738 S | 4/2019 | Kalina, Jr. et al. |
| 10,245,178 B1 | 4/2019 | Heitzmann et al. |
| 10,271,989 B2 | 4/2019 | Haffner et al. |
| 10,285,853 B2 | 5/2019 | Rangel-Friedman et al. |
| 10,285,856 B2 | 5/2019 | Tu et al. |
| 10,406,029 B2 | 9/2019 | Tu et al. |
| 10,485,701 B2 | 11/2019 | Haffner et al. |
| 10,485,702 B2 | 11/2019 | Bergheim et al. |
| 10,492,950 B2 | 12/2019 | Lynch et al. |
| 10,499,809 B2 | 12/2019 | Kalina, Jr. et al. |
| 10,517,759 B2 | 12/2019 | Crimaldi et al. |
| 10,568,762 B2 | 2/2020 | Lynch et al. |
| D886,997 S | 6/2020 | Kalina, Jr. et al. |
| 10,674,906 B2 | 6/2020 | Kalina, Jr. et al. |
| 10,813,789 B2 | 10/2020 | Haffner et al. |
| D901,683 S | 11/2020 | Kalina, Jr. et al. |
| 10,828,195 B2 | 11/2020 | Burns et al. |
| 10,828,473 B2 | 11/2020 | Haffner et al. |
| 10,959,941 B2 | 3/2021 | Haffner |
| 11,019,996 B2 | 6/2021 | Kalina, Jr. et al. |
| 11,019,997 B2 | 6/2021 | Kalina, Jr. et al. |
| 11,116,625 B2 | 9/2021 | Kalina, Jr. |
| D938,585 S | 12/2021 | Kalina, Jr. et al. |
| 11,197,780 B2 | 12/2021 | Haffner et al. |
| 11,253,394 B2 | 2/2022 | Haffner et al. |
| 11,318,043 B2 | 5/2022 | Heitzmann et al. |

(56) References Cited

U.S. PATENT DOCUMENTS

| | | |
|---|---|---|
| 11,376,040 B2 | 7/2022 | Kalina, Jr. et al. |
| 11,426,306 B2 | 8/2022 | Haffner et al. |
| 2002/0013572 A1 | 1/2002 | Berlin |
| 2002/0052640 A1 | 5/2002 | Bigus et al. |
| 2002/0071866 A1 | 6/2002 | Geerke |
| 2002/0102307 A1 | 8/2002 | Guo et al. |
| 2002/0106395 A1 | 8/2002 | Brubaker |
| 2002/0110591 A1 | 8/2002 | Brubaker et al. |
| 2002/0110592 A1 | 8/2002 | Brubaker et al. |
| 2002/0110635 A1 | 8/2002 | Brubaker et al. |
| 2002/0111601 A1 | 8/2002 | Thompson |
| 2002/0111603 A1 | 8/2002 | Cheikh |
| 2002/0127250 A1 | 9/2002 | Guo et al. |
| 2002/0128704 A1 | 9/2002 | Daum et al. |
| 2002/0133168 A1 | 9/2002 | Smedley et al. |
| 2002/0143284 A1 | 10/2002 | Tu et al. |
| 2002/0176844 A1 | 11/2002 | Ng et al. |
| 2002/0182185 A1 | 12/2002 | Wong |
| 2002/0188282 A1 | 12/2002 | Greenberg |
| 2002/0197298 A1 | 12/2002 | Yaacobi |
| 2003/0003129 A1 | 1/2003 | Yaacobi |
| 2003/0004209 A1 | 1/2003 | Hunter et al. |
| 2003/0010638 A1 | 1/2003 | Hansord et al. |
| 2003/0018295 A1 | 1/2003 | Henley et al. |
| 2003/0019833 A1 | 1/2003 | Unger et al. |
| 2003/0021828 A1 | 1/2003 | Guo et al. |
| 2003/0055372 A1 | 3/2003 | Lynch et al. |
| 2003/0060752 A1 | 3/2003 | Bergheim et al. |
| 2003/0060873 A1 | 3/2003 | Gertner et al. |
| 2003/0064088 A1 | 4/2003 | Carvalho et al. |
| 2003/0083646 A1 | 5/2003 | Sirhan et al. |
| 2003/0095995 A1 | 5/2003 | Wong et al. |
| 2003/0097117 A1 | 5/2003 | Buono |
| 2003/0097151 A1 | 5/2003 | Smedley et al. |
| 2003/0108588 A1 | 6/2003 | Chen et al. |
| 2003/0119000 A1 | 6/2003 | Polansky |
| 2003/0139784 A1 | 7/2003 | Morimoto et al. |
| 2003/0143274 A1 | 7/2003 | Viegas et al. |
| 2003/0175324 A1 | 9/2003 | Robinson et al. |
| 2003/0176854 A1 | 9/2003 | Rodstrom |
| 2003/0181848 A1 | 9/2003 | Bergheim et al. |
| 2003/0187384 A1 | 10/2003 | Bergheim et al. |
| 2003/0195438 A1 | 10/2003 | Petillo |
| 2003/0203003 A1 | 10/2003 | Nelson et al. |
| 2003/0208163 A1 | 11/2003 | Yaron et al. |
| 2003/0211071 A1 | 11/2003 | Bologna et al. |
| 2003/0229303 A1 | 12/2003 | Haffner et al. |
| 2003/0236484 A1 | 12/2003 | Lynch et al. |
| 2004/0013702 A1 | 1/2004 | Glover |
| 2004/0018238 A1 | 1/2004 | Shukla |
| 2004/0022853 A1 | 2/2004 | Ashton et al. |
| 2004/0024345 A1 | 2/2004 | Gharib et al. |
| 2004/0034357 A1 | 2/2004 | Beane et al. |
| 2004/0057979 A1 | 3/2004 | Wong et al. |
| 2004/0082939 A1 | 4/2004 | Berlin |
| 2004/0092548 A1 | 5/2004 | Embleton et al. |
| 2004/0092911 A1 | 5/2004 | Yaacobi |
| 2004/0111050 A1 | 6/2004 | Smedley et al. |
| 2004/0111080 A1 | 6/2004 | Harper et al. |
| 2004/0115268 A1 | 6/2004 | Ashton et al. |
| 2004/0127843 A1 | 7/2004 | Tu et al. |
| 2004/0131654 A1 | 7/2004 | Yaacobi |
| 2004/0131655 A1 | 7/2004 | Yaacobi |
| 2004/0137059 A1 | 7/2004 | Nivaggioli et al. |
| 2004/0147870 A1 | 7/2004 | Burns et al. |
| 2004/0151714 A1 | 8/2004 | Soll |
| 2004/0154946 A1 | 8/2004 | Solovay et al. |
| 2004/0163652 A1 | 8/2004 | Watson |
| 2004/0175410 A1 | 9/2004 | Ashton et al. |
| 2004/0176341 A1 | 9/2004 | Chou et al. |
| 2004/0176737 A1 | 9/2004 | Henley et al. |
| 2004/0180075 A1 | 9/2004 | Robinson et al. |
| 2004/0186533 A1 | 9/2004 | Greenberg et al. |
| 2004/0186534 A1 | 9/2004 | Shadduck |
| 2004/0208909 A1 | 10/2004 | Brubaker et al. |
| 2004/0208910 A1 | 10/2004 | Ashton et al. |
| 2004/0210185 A1 | 10/2004 | Tu et al. |
| 2004/0216749 A1 | 11/2004 | Tu |
| 2004/0219181 A1 | 11/2004 | Viscasillas |
| 2004/0220537 A1 | 11/2004 | Embleton et al. |
| 2004/0249404 A1 | 12/2004 | Haefliger |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0008673 A1 | 1/2005 | Snyder et al. |
| 2005/0042293 A1 | 2/2005 | Jackson et al. |
| 2005/0049578 A1 | 3/2005 | Tu et al. |
| 2005/0055075 A1 | 3/2005 | Pinchuk et al. |
| 2005/0064010 A1 | 3/2005 | Cooper et al. |
| 2005/0069893 A1 | 3/2005 | Flammer et al. |
| 2005/0112175 A1 | 5/2005 | Yaacobi |
| 2005/0119737 A1 | 6/2005 | Bene et al. |
| 2005/0137538 A1 | 6/2005 | Kunzler et al. |
| 2005/0165368 A1 | 7/2005 | Py et al. |
| 2005/0171490 A1 | 8/2005 | Weaver et al. |
| 2005/0175708 A1 | 8/2005 | Carrasquillo et al. |
| 2005/0181018 A1 | 8/2005 | Peyman |
| 2005/0186245 A1 | 8/2005 | Hunter et al. |
| 2005/0186279 A1 | 8/2005 | Guo et al. |
| 2005/0208102 A1 | 9/2005 | Schultz |
| 2005/0209549 A1 | 9/2005 | Bergheim et al. |
| 2005/0222537 A1 | 10/2005 | Dinsmoor et al. |
| 2005/0232972 A1 | 10/2005 | Odrich |
| 2005/0244461 A1 | 11/2005 | Nivaggioli et al. |
| 2005/0244464 A1 | 11/2005 | Hughes |
| 2005/0244465 A1 | 11/2005 | Nivaggioli et al. |
| 2005/0244467 A1 | 11/2005 | Nivaggioli et al. |
| 2005/0244470 A1 | 11/2005 | Hughes et al. |
| 2005/0244475 A1 | 11/2005 | Edelman et al. |
| 2005/0244477 A1 | 11/2005 | Hughes et al. |
| 2005/0244500 A1 | 11/2005 | Whitcup et al. |
| 2005/0244506 A1 | 11/2005 | Burke et al. |
| 2005/0249710 A1 | 11/2005 | Wong |
| 2005/0250788 A1 | 11/2005 | Tu et al. |
| 2005/0261641 A1 | 11/2005 | Warchol et al. |
| 2005/0276841 A1 | 12/2005 | Davis et al. |
| 2005/0277864 A1 | 12/2005 | Haffner et al. |
| 2005/0281861 A1 | 12/2005 | Hughes et al. |
| 2005/0287188 A1 | 12/2005 | Anderson et al. |
| 2005/0288619 A1 | 12/2005 | Gharib et al. |
| 2006/0009498 A1 | 1/2006 | Whitcup |
| 2006/0020248 A1 | 1/2006 | Prescott |
| 2006/0020253 A1* | 1/2006 | Prescott .............. A61F 9/00772 604/500 |
| 2006/0021623 A1 | 2/2006 | Varner et al. |
| 2006/0024350 A1 | 2/2006 | Miller et al. |
| 2006/0032507 A1 | 2/2006 | Tu |
| 2006/0034929 A1 | 2/2006 | Brubaker |
| 2006/0039952 A1 | 2/2006 | Yaacobi |
| 2006/0039979 A1 | 2/2006 | Yamada et al. |
| 2006/0062826 A1 | 3/2006 | Brubaker et al. |
| 2006/0067978 A1 | 3/2006 | Heiler et al. |
| 2006/0074375 A1 | 4/2006 | Bergheim et al. |
| 2006/0083772 A1 | 4/2006 | DeWitt et al. |
| 2006/0084907 A1 | 4/2006 | Bergheim et al. |
| 2006/0084952 A1 | 4/2006 | Pallikaris et al. |
| 2006/0089590 A1 | 4/2006 | Powell et al. |
| 2006/0100408 A1 | 5/2006 | Higuchi et al. |
| 2006/0110429 A1 | 5/2006 | Reiff et al. |
| 2006/0135918 A1 | 6/2006 | LaRuffa |
| 2006/0136022 A1 | 6/2006 | Wong, Jr. et al. |
| 2006/0167435 A1 | 7/2006 | Adamis et al. |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0200097 A1 | 9/2006 | Humayun et al. |
| 2006/0200113 A1 | 9/2006 | Haffner et al. |
| 2006/0210604 A1 | 9/2006 | Dadey et al. |
| 2006/0216329 A1 | 9/2006 | Peyman |
| 2006/0246112 A1 | 11/2006 | Snyder et al. |
| 2006/0246145 A1 | 11/2006 | Chang et al. |
| 2006/0253151 A1 | 11/2006 | Nun |
| 2006/0257450 A1 | 11/2006 | Mudumba et al. |
| 2006/0257451 A1 | 11/2006 | Varner et al. |

(56) References Cited

U.S. PATENT DOCUMENTS

| | | |
|---|---|---|
| 2006/0258994 A1 | 11/2006 | Avery |
| 2006/0264453 A1 | 11/2006 | Mudumba et al. |
| 2006/0270968 A1 | 11/2006 | Greenberg et al. |
| 2006/0276738 A1* | 12/2006 | Becker ................ A61F 9/00772 604/8 |
| 2006/0292222 A1 | 12/2006 | Jonasse |
| 2007/0021653 A1 | 1/2007 | Hattenbach et al. |
| 2007/0026037 A1 | 2/2007 | Kloke et al. |
| 2007/0026048 A1 | 2/2007 | Greeberg |
| 2007/0031472 A1 | 2/2007 | Huang et al. |
| 2007/0031473 A1 | 2/2007 | Peyman |
| 2007/0032734 A1 | 2/2007 | Najafi et al. |
| 2007/0038174 A1 | 2/2007 | Hopkins |
| 2007/0059336 A1 | 3/2007 | Hughes et al. |
| 2007/0088014 A1 | 4/2007 | Edelman et al. |
| 2007/0088432 A1 | 4/2007 | Solovay et al. |
| 2007/0092570 A1 | 4/2007 | Missel et al. |
| 2007/0106199 A1 | 5/2007 | Krivoy et al. |
| 2007/0112318 A1 | 5/2007 | Leahy et al. |
| 2007/0118065 A1 | 5/2007 | Pinchuk et al. |
| 2007/0118066 A1 | 5/2007 | Pinchuk et al. |
| 2007/0190111 A1 | 8/2007 | Robinson et al. |
| 2007/0197957 A1 | 8/2007 | Hunter et al. |
| 2007/0202186 A1 | 8/2007 | Yamamoto et al. |
| 2007/0212395 A1 | 9/2007 | Donello et al. |
| 2007/0212397 A1 | 9/2007 | Roth |
| 2007/0233037 A1 | 10/2007 | Gifford, III et al. |
| 2007/0244442 A1 | 10/2007 | Chowhan |
| 2007/0249984 A1 | 10/2007 | Molteno |
| 2007/0260203 A1 | 11/2007 | Donello et al. |
| 2007/0268340 A1 | 11/2007 | Dacquay et al. |
| 2007/0269487 A1 | 11/2007 | de Juan et al. |
| 2007/0270744 A1 | 11/2007 | Dacquay et al. |
| 2007/0270748 A1 | 11/2007 | Dacquay et al. |
| 2007/0270768 A1 | 11/2007 | Dacquay et al. |
| 2007/0270777 A1 | 11/2007 | Dacquay et al. |
| 2007/0282244 A1 | 12/2007 | Tu et al. |
| 2007/0282245 A1 | 12/2007 | Tu et al. |
| 2007/0292596 A1 | 12/2007 | Chappa et al. |
| 2007/0293807 A1 | 12/2007 | Lynch et al. |
| 2007/0293820 A1 | 12/2007 | Dacquay et al. |
| 2007/0293872 A1 | 12/2007 | Peyman |
| 2007/0293873 A1 | 12/2007 | Chang |
| 2007/0298073 A1 | 12/2007 | Whitcup et al. |
| 2007/0298074 A1 | 12/2007 | Robinson et al. |
| 2007/0299516 A1 | 12/2007 | Cui et al. |
| 2008/0038316 A1 | 2/2008 | Wong, Jr. et al. |
| 2008/0039769 A1 | 2/2008 | Peyman |
| 2008/0039792 A1 | 2/2008 | Meng et al. |
| 2008/0045878 A1 | 2/2008 | Bergheim et al. |
| 2008/0045911 A1 | 2/2008 | Borgia et al. |
| 2008/0051680 A1 | 2/2008 | Luebcke |
| 2008/0057101 A1 | 3/2008 | Roorda |
| 2008/0057102 A1 | 3/2008 | Roorda |
| 2008/0057103 A1 | 3/2008 | Roorda |
| 2008/0057123 A1 | 3/2008 | Grenier et al. |
| 2008/0058704 A1 | 3/2008 | Hee et al. |
| 2008/0058793 A1 | 3/2008 | Pilla et al. |
| 2008/0063687 A1 | 3/2008 | Chou et al. |
| 2008/0063898 A1 | 3/2008 | Lally et al. |
| 2008/0071252 A1 | 3/2008 | Santini, Jr. et al. |
| 2008/0075753 A1 | 3/2008 | Chappa |
| 2008/0081064 A1 | 4/2008 | Jelle et al. |
| 2008/0086101 A1 | 4/2008 | Freilich |
| 2008/0089923 A1 | 4/2008 | Burkstrand et al. |
| 2008/0095822 A1 | 4/2008 | Maquet et al. |
| 2008/0097379 A1 | 4/2008 | Daquay et al. |
| 2008/0097390 A1 | 4/2008 | Daquay et al. |
| 2008/0107694 A1 | 5/2008 | Trogden et al. |
| 2008/0112923 A1 | 5/2008 | Hughes et al. |
| 2008/0113031 A1 | 5/2008 | Moodley et al. |
| 2008/0114076 A1 | 5/2008 | Asgharian et al. |
| 2008/0125712 A1 | 5/2008 | Dacquay et al. |
| 2008/0131372 A1 | 6/2008 | Huang et al. |
| 2008/0131481 A1 | 6/2008 | Hughes |
| 2008/0131482 A1 | 6/2008 | Hughes |
| 2008/0131484 A1 | 6/2008 | Robinson et al. |
| 2008/0131486 A1 | 6/2008 | Huang et al. |
| 2008/0138382 A1 | 6/2008 | Huang et al. |
| 2008/0138408 A1 | 6/2008 | Venkatesh et al. |
| 2008/0140024 A1 | 6/2008 | Yaacobi |
| 2008/0145405 A1 | 6/2008 | Kunzler et al. |
| 2008/0145406 A1 | 6/2008 | Asgharian et al. |
| 2008/0147021 A1 | 6/2008 | Jani |
| 2008/0152694 A1 | 6/2008 | Lobl et al. |
| 2008/0231485 A1 | 6/2008 | Huang et al. |
| 2008/0161741 A1 | 7/2008 | Bene et al. |
| 2008/0161907 A1 | 7/2008 | Chen et al. |
| 2008/0167600 A1 | 7/2008 | Peyman |
| 2008/0172014 A1 | 7/2008 | Whitcup et al. |
| 2008/0177153 A1 | 7/2008 | Bachman et al. |
| 2008/0177220 A1 | 7/2008 | Lindgren et al. |
| 2008/0181928 A1 | 7/2008 | Hokimi-Mehr et al. |
| 2008/0181929 A1 | 7/2008 | Robinson et al. |
| 2008/0183123 A1 | 7/2008 | Behar-Cohen et al. |
| 2008/0208334 A1 | 8/2008 | Jinkerson et al. |
| 2008/0208557 A1 | 8/2008 | Katano |
| 2008/0210322 A1 | 9/2008 | Unger et al. |
| 2008/0228127 A1 | 9/2008 | Burns et al. |
| 2008/0233171 A1 | 9/2008 | Whitcup et al. |
| 2008/0233172 A1 | 9/2008 | Whitcup et al. |
| 2008/0233173 A1 | 9/2008 | Whitcup et al. |
| 2008/0236669 A1 | 10/2008 | Unger et al. |
| 2008/0241222 A1 | 10/2008 | Whitcup et al. |
| 2008/0241223 A1 | 10/2008 | Nivaggio et al. |
| 2008/0260803 A1 | 10/2008 | Hughes et al. |
| 2008/0277007 A1 | 11/2008 | Unger et al. |
| 2008/0286336 A1 | 11/2008 | Shiah et al. |
| 2008/0286338 A1 | 11/2008 | Rosenthal et al. |
| 2008/0289710 A1 | 11/2008 | Unger et al. |
| 2008/0292679 A1 | 11/2008 | Lyons et al. |
| 2008/0306429 A1 | 12/2008 | Shields et al. |
| 2008/0318843 A1 | 12/2008 | Schultz et al. |
| 2009/0003525 A1 | 1/2009 | Gertner et al. |
| 2009/0036768 A1 | 2/2009 | Seehusen et al. |
| 2009/0043250 A1 | 2/2009 | Gonnelli |
| 2009/0043321 A1 | 2/2009 | Conston et al. |
| 2009/0047256 A1 | 2/2009 | Bettinger et al. |
| 2009/0060981 A1 | 3/2009 | Chauhan |
| 2009/0074786 A1 | 3/2009 | Dor et al. |
| 2009/0076436 A2 | 3/2009 | Gharib et al. |
| 2009/0082321 A1 | 3/2009 | Edelman et al. |
| 2009/0092654 A1 | 4/2009 | de Juan, Jr. et al. |
| 2009/0093780 A1 | 4/2009 | Tuitupou et al. |
| 2009/0104248 A1* | 4/2009 | Rapacki ................ A61F 9/0017 424/427 |
| 2009/0112190 A1 | 4/2009 | Boyden et al. |
| 2009/0118702 A1 | 5/2009 | Lazar |
| 2009/0123515 A1 | 5/2009 | Taylor et al. |
| 2009/0123546 A1 | 5/2009 | Ashton et al. |
| 2009/0142413 A1 | 6/2009 | Allen et al. |
| 2009/0143752 A1 | 6/2009 | Higuchi et al. |
| 2009/0148498 A1 | 6/2009 | Libin et al. |
| 2009/0149947 A1 | 6/2009 | Frohwitter |
| 2009/0151422 A1 | 6/2009 | Unger et al. |
| 2009/0155338 A1 | 6/2009 | Conway et al. |
| 2009/0157087 A1 | 6/2009 | Wei et al. |
| 2009/0162417 A1 | 6/2009 | Eellis |
| 2009/0177182 A1 | 7/2009 | Hickingbotham et al. |
| 2009/0196903 A1 | 8/2009 | Kilman |
| 2009/0196906 A1 | 8/2009 | Spada et al. |
| 2009/0209945 A1 | 8/2009 | Lobl et al. |
| 2009/0214619 A1 | 8/2009 | Reiff et al. |
| 2009/0220572 A1 | 9/2009 | Deschatelets et al. |
| 2009/0220573 A1 | 9/2009 | Kaufman |
| 2009/0227933 A1 | 9/2009 | Karageozian |
| 2009/0240215 A1 | 9/2009 | Humayun et al. |
| 2009/0246252 A1 | 10/2009 | Arps et al. |
| 2009/0264861 A1 | 10/2009 | Jain et al. |
| 2009/0270308 A1 | 10/2009 | Libin et al. |
| 2009/0274877 A1 | 11/2009 | Chan et al. |
| 2009/0275924 A1 | 11/2009 | Lattanzio et al. |
| 2009/0280155 A1 | 11/2009 | Chappa et al. |

(56) References Cited

U.S. PATENT DOCUMENTS

| | | | |
|---|---|---|---|
| 2009/0280158 A1* | 11/2009 | Butuner | A61K 9/0051 424/428 |
| 2009/0286773 A1 | 11/2009 | Spada et al. | |
| 2009/0287274 A1 | 11/2009 | De Rodder | |
| 2009/0294345 A1 | 12/2009 | Kelly et al. | |
| 2009/0306585 A1 | 12/2009 | Pang et al. | |
| 2009/0306595 A1 | 12/2009 | Shih et al. | |
| 2009/0306608 A1* | 12/2009 | Li | A61K 9/0051 604/294 |
| 2009/0312742 A1 | 12/2009 | Pang et al. | |
| 2009/0326432 A1 | 12/2009 | Schmidt et al. | |
| 2010/0004581 A1 | 1/2010 | Brigatti et al. | |
| 2010/0004639 A1 | 1/2010 | Pang et al. | |
| 2010/0015195 A1 | 1/2010 | Jain et al. | |
| 2010/0030136 A1 | 2/2010 | Dacquay et al. | |
| 2010/0040670 A1 | 2/2010 | Odrich et al. | |
| 2010/0056979 A1 | 3/2010 | Smedley et al. | |
| 2010/0057003 A1 | 3/2010 | Dos Santos | |
| 2010/0068141 A1 | 3/2010 | Kaushal et al. | |
| 2010/0069842 A1 | 3/2010 | Dos Santos et al. | |
| 2010/0092536 A1 | 4/2010 | Hunter et al. | |
| 2010/0100054 A1 | 4/2010 | Cormier et al. | |
| 2010/0106073 A1 | 4/2010 | Haffner et al. | |
| 2010/0114039 A1 | 5/2010 | Gazzini | |
| 2010/0114309 A1* | 5/2010 | de Juan, Jr. | A61P 27/02 623/6.39 |
| 2010/0119519 A1 | 5/2010 | Peyman | |
| 2010/0119580 A1 | 5/2010 | Guo et al. | |
| 2010/0119694 A1 | 5/2010 | Guo et al. | |
| 2010/0124565 A1 | 5/2010 | Spada et al. | |
| 2010/0129424 A9 | 5/2010 | Byrne et al. | |
| 2010/0137780 A1 | 6/2010 | Singh et al. | |
| 2010/0145180 A1 | 6/2010 | Abreu | |
| 2010/0152676 A1 | 6/2010 | Clements | |
| 2010/0152699 A1 | 6/2010 | Ferrari et al. | |
| 2010/0158980 A1 | 6/2010 | Kopczynski et al. | |
| 2010/0160870 A1 | 6/2010 | Clements et al. | |
| 2010/0173866 A1 | 7/2010 | Hee et al. | |
| 2010/0189765 A1 | 7/2010 | Erickson et al. | |
| 2010/0189766 A1 | 7/2010 | Utkhede et al. | |
| 2010/0189817 A1 | 7/2010 | Kruger et al. | |
| 2010/0191103 A1 | 7/2010 | Stamper et al. | |
| 2010/0203155 A1 | 8/2010 | Wei et al. | |
| 2010/0204325 A1 | 8/2010 | Blanda et al. | |
| 2010/0204699 A1 | 8/2010 | Wei et al. | |
| 2010/0211044 A1 | 8/2010 | Dacquay et al. | |
| 2010/0222752 A1 | 9/2010 | Collins, Jr. et al. | |
| 2010/0225061 A1 | 9/2010 | Bath | |
| 2010/0233241 A1 | 9/2010 | Leahy et al. | |
| 2010/0234817 A1 | 9/2010 | Nazzaro et al. | |
| 2010/0239635 A1 | 9/2010 | McClain et al. | |
| 2010/0239637 A1 | 9/2010 | Ciolino et al. | |
| 2010/0241046 A1 | 9/2010 | Pinchuk et al. | |
| 2010/0241055 A1 | 9/2010 | Dacey, Jr. et al. | |
| 2010/0247606 A1 | 9/2010 | Robinson et al. | |
| 2010/0249692 A1 | 9/2010 | Dacey, Jr. et al. | |
| 2010/0255061 A1 | 10/2010 | De Juan, Jr. et al. | |
| 2010/0256578 A1 | 10/2010 | Lust et al. | |
| 2010/0256597 A1 | 10/2010 | Prausnitz et al. | |
| 2010/0261646 A1 | 10/2010 | Lavik et al. | |
| 2010/0266664 A1 | 10/2010 | Asgharian et al. | |
| 2010/0274204 A1 | 10/2010 | Rapacki et al. | |
| 2010/0274224 A1 | 10/2010 | Jain et al. | |
| 2010/0274258 A1 | 10/2010 | Silvestrini et al. | |
| 2010/0274259 A1 | 10/2010 | Yaron et al. | |
| 2010/0278898 A1 | 11/2010 | Hughes et al. | |
| 2010/0310622 A1 | 12/2010 | Chauhan et al. | |
| 2010/0318034 A1 | 12/2010 | Goncalves | |
| 2010/0331796 A1 | 12/2010 | Leahy et al. | |
| 2011/0022007 A1 | 1/2011 | Li et al. | |
| 2011/0053905 A1 | 3/2011 | Guo et al. | |
| 2011/0054418 A1* | 3/2011 | Pugh | A61F 9/0026 604/285 |
| 2011/0076318 A1 | 3/2011 | Hughes et al. | |
| 2011/0091520 A1 | 4/2011 | Huang et al. | |
| 2011/0092878 A1 | 4/2011 | Tu et al. | |
| 2011/0098632 A1 | 4/2011 | Behar-Cohen et al. | |
| 2011/0098640 A1 | 4/2011 | Horne et al. | |
| 2011/0104155 A1 | 5/2011 | Rekik | |
| 2011/0106006 A1 | 5/2011 | Martin et al. | |
| 2011/0112352 A1 | 5/2011 | Pilla et al. | |
| 2011/0112470 A1 | 5/2011 | Lingenfelder et al. | |
| 2011/0112475 A1 | 5/2011 | Benson | |
| 2011/0125090 A1 | 5/2011 | Peyman | |
| 2011/0129516 A1 | 6/2011 | Jacob et al. | |
| 2011/0129541 A1 | 6/2011 | Chen et al. | |
| 2011/0152767 A1 | 6/2011 | Pinedjian | |
| 2011/0166500 A1 | 7/2011 | Roy | |
| 2011/0172528 A1 | 7/2011 | Gertner | |
| 2011/0172587 A1 | 7/2011 | Santini, Jr. et al. | |
| 2011/0182966 A1 | 7/2011 | Robinson et al. | |
| 2011/0202020 A1 | 8/2011 | Lazar | |
| 2011/0207987 A1 | 8/2011 | DiCarlo et al. | |
| 2011/0238036 A1 | 9/2011 | Ashton | |
| 2011/0238075 A1 | 9/2011 | Clauson et al. | |
| 2011/0244010 A1 | 10/2011 | Doshi | |
| 2011/0251568 A1* | 10/2011 | Beeley | A61P 27/02 604/294 |
| 2011/0288396 A1 | 11/2011 | Iyengar et al. | |
| 2012/0022505 A1 | 1/2012 | Dacquay et al. | |
| 2012/0035146 A1 | 2/2012 | Wong et al. | |
| 2012/0035528 A1 | 2/2012 | Coppeta et al. | |
| 2012/0059338 A1* | 3/2012 | Beeley | A61F 9/00772 604/294 |
| 2012/0059349 A1 | 3/2012 | Kuo et al. | |
| 2012/0078158 A1 | 3/2012 | Haffner et al. | |
| 2012/0078224 A1 | 3/2012 | Lerner et al. | |
| 2012/0078362 A1* | 3/2012 | Haffner | A61F 9/0017 623/6.13 |
| 2012/0083765 A1 | 4/2012 | LaBelle | |
| 2012/0089072 A1 | 4/2012 | Cunningham, Jr. | |
| 2012/0089073 A1 | 4/2012 | Cunningham, Jr. | |
| 2012/0089113 A1 | 4/2012 | Ambati et al. | |
| 2012/0100187 A1 | 4/2012 | Chappa et al. | |
| 2012/0107371 A1 | 5/2012 | Zion et al. | |
| 2012/0109040 A1 | 5/2012 | Smedley et al. | |
| 2012/0136322 A1 | 5/2012 | Alster et al. | |
| 2012/0157487 A1 | 6/2012 | Yuan et al. | |
| 2012/0165933 A1 | 6/2012 | Haffner et al. | |
| 2012/0177717 A1 | 7/2012 | Abe et al. | |
| 2012/0179122 A1 | 7/2012 | Eilat et al. | |
| 2012/0197217 A1* | 8/2012 | Coldren | A61F 9/0017 604/294 |
| 2012/0238994 A1 | 9/2012 | Nazzaro et al. | |
| 2012/0245505 A1 | 9/2012 | Robinson et al. | |
| 2012/0253300 A1 | 10/2012 | Kaufman | |
| 2012/0257167 A1 | 10/2012 | Gille et al. | |
| 2012/0259195 A1 | 10/2012 | Haffner et al. | |
| 2012/0265149 A1 | 10/2012 | Lerner et al. | |
| 2012/0277733 A1 | 11/2012 | Pang et al. | |
| 2012/0321719 A1 | 12/2012 | McDonnell et al. | |
| 2013/0004651 A1 | 1/2013 | Fu-Giles | |
| 2013/0017244 A1 | 1/2013 | Huang et al. | |
| 2013/0017262 A1 | 1/2013 | Mullen et al. | |
| 2013/0018295 A1 | 1/2013 | Haffner et al. | |
| 2013/0018296 A1 | 1/2013 | Bergheim et al. | |
| 2013/0018360 A1 | 1/2013 | Dockendorf et al. | |
| 2013/0023838 A1 | 1/2013 | Leahy et al. | |
| 2013/0053794 A1* | 2/2013 | Cadden | A61K 9/0092 604/290 |
| 2013/0060227 A1 | 3/2013 | Singh et al. | |
| 2013/0062809 A1 | 3/2013 | Ellis | |
| 2013/0071349 A1 | 3/2013 | Robinson et al. | |
| 2013/0071462 A1 | 3/2013 | Jarrett et al. | |
| 2013/0090534 A1 | 4/2013 | Burns et al. | |
| 2013/0090612 A1 | 4/2013 | De Juan, Jr. et al. | |
| 2013/0110125 A1 | 5/2013 | Silvestrini et al. | |
| 2013/0116523 A1 | 5/2013 | Jung et al. | |
| 2013/0142858 A1 | 6/2013 | Kopczynski et al. | |
| 2013/0144128 A1 | 6/2013 | De Juan, Jr. et al. | |
| 2013/0150770 A1 | 6/2013 | Horvath et al. | |
| 2013/0150773 A1 | 6/2013 | Nissan et al. | |
| 2013/0150774 A1 | 6/2013 | Field et al. | |
| 2013/0156840 A1 | 6/2013 | Basinger et al. | |

(56) References Cited

U.S. PATENT DOCUMENTS

| | | |
|---|---|---|
| 2013/0158561 A1 | 6/2013 | Bhagat |
| 2013/0184661 A1 | 7/2013 | Beaton et al. |
| 2013/0253404 A1 | 9/2013 | Tu |
| 2013/0253405 A1 | 9/2013 | Tu |
| 2013/0281910 A1 | 10/2013 | Tu |
| 2013/0289467 A1 | 10/2013 | Haffner et al. |
| 2013/0310930 A1 | 11/2013 | Tu et al. |
| 2014/0035184 A1 | 2/2014 | Nivaggioli et al. |
| 2014/0037746 A1 | 2/2014 | Ashton et al. |
| 2014/0039456 A1 | 2/2014 | Lerner |
| 2014/0135712 A1 | 5/2014 | Horne et al. |
| 2014/0234389 A1 | 8/2014 | Shiah et al. |
| 2014/0294986 A1 | 10/2014 | Liu et al. |
| 2014/0303544 A1 | 10/2014 | Haffner et al. |
| 2015/0118279 A1 | 4/2015 | Ghebremeskel et al. |
| 2015/0223981 A1 | 8/2015 | Smedley et al. |
| 2015/0342875 A1 | 12/2015 | Haffner |
| 2016/0354245 A1 | 8/2016 | Horvath et al. |
| 2016/0354309 A1 | 12/2016 | Heitzman et al. |
| 2017/0135857 A1 | 5/2017 | Hafner et al. |
| 2017/0281409 A1 | 10/2017 | Haffner et al. |
| 2018/0000642 A1 | 1/2018 | Rapacki et al. |
| 2018/0021170 A1 | 1/2018 | Haffner et al. |
| 2018/0028361 A1 | 2/2018 | Haffner et al. |
| 2018/0085065 A1 | 3/2018 | Haffner et al. |
| 2018/0161205 A1 | 6/2018 | Tu et al. |
| 2018/0177633 A1 | 6/2018 | Haffner et al. |
| 2018/0280194 A1 | 10/2018 | Heitzmann et al. |
| 2018/0303665 A1 | 10/2018 | Heitzmann et al. |
| 2018/0303752 A1 | 10/2018 | Haffner |
| 2018/0333296 A1 | 11/2018 | Heitzmann et al. |
| 2019/0000673 A1 | 1/2019 | Fjield et al. |
| 2019/0021991 A9 | 1/2019 | Heitzmann et al. |
| 2019/0053704 A1 | 2/2019 | Burns et al. |
| 2019/0091012 A1 | 3/2019 | Kalina, Jr. |
| 2019/0104936 A1 | 4/2019 | Gunn et al. |
| 2019/0105077 A1 | 4/2019 | Kalina, Jr. et al. |
| 2019/0125581 A1 | 5/2019 | Heitzmann et al. |
| 2019/0224046 A1 | 7/2019 | Heitzmann et al. |
| 2019/0314199 A1 | 10/2019 | Haffner et al. |
| 2019/0321220 A1 | 10/2019 | Rangel-Friedman et al. |
| 2019/0321225 A1 | 10/2019 | Smedley et al. |
| 2019/0321226 A1 | 10/2019 | Haffner et al. |
| 2020/0155349 A1 | 5/2020 | Haffner et al. |
| 2020/0179171 A1 | 6/2020 | Crimaldi et al. |
| 2020/0214560 A1 | 7/2020 | Kalina, Jr. et al. |
| 2020/0214561 A1 | 7/2020 | Kalina, Jr. et al. |
| 2020/0367745 A1 | 11/2020 | Kalina, Jr. et al. |
| 2021/0015662 A1 | 1/2021 | Haffner et al. |
| 2021/0137737 A1 | 5/2021 | Burns et al. |
| 2021/0154449 A1 | 5/2021 | Haffner et al. |
| 2021/0298948 A1 | 9/2021 | Haffner et al. |
| 2021/0315806 A1 | 10/2021 | Haffner |
| 2021/0369447 A1 | 12/2021 | Kalina, Jr. |
| 2022/0000663 A1 | 1/2022 | Haffner et al. |
| 2022/0015628 A1 | 1/2022 | Kalina, Jr. et al. |
| 2022/0233349 A1 | 7/2022 | Haffner et al. |
| 2022/0233354 A1 | 7/2022 | Haffner et al. |

FOREIGN PATENT DOCUMENTS

| | | |
|---|---|---|
| CA | 2830555 | 4/2015 |
| CA | 2762536 | 11/2020 |
| CN | 101396335 A | 4/2009 |
| EP | 0180708 | 5/1986 |
| EP | 0387155 | 9/1990 |
| EP | 0613383 B1 | 8/1997 |
| EP | 1100462 A2 | 5/2001 |
| EP | 1296645 A2 | 4/2003 |
| EP | 1339438 A2 | 9/2003 |
| EP | 1420716 A1 | 5/2004 |
| EP | 1477187 A1 | 11/2004 |
| EP | 1534363 A2 | 6/2005 |
| EP | 1550471 A1 | 7/2005 |
| EP | 1592407 | 11/2005 |
| EP | 1621219 A2 | 2/2006 |
| EP | 1637126 A2 | 3/2006 |
| EP | 1521573 | 1/2008 |
| EP | 2260803 | 12/2010 |
| EP | 2260804 | 12/2010 |
| EP | 2263621 | 12/2010 |
| EP | 2351589 | 8/2011 |
| EP | 2982354 | 2/2016 |
| EP | 2985012 | 2/2016 |
| EP | 2902018 | 11/2016 |
| EP | 2967993 | 4/2019 |
| ES | 2048986 | 4/1994 |
| JP | 2003-520077 | 7/2003 |
| JP | 2003-275327 | 9/2003 |
| JP | 2003-530964 | 10/2003 |
| JP | 2004-500220 | 1/2004 |
| JP | 2005-512607 | 5/2005 |
| JP | 3703721 | 7/2005 |
| JP | 2007-501066 | 1/2007 |
| JP | 2008-500878 | 1/2008 |
| JP | 4031836 | 1/2008 |
| JP | 2009-056324 | 3/2009 |
| JP | 2009-523540 | 6/2009 |
| JP | 2009-532132 | 9/2009 |
| JP | 2010-509003 | 3/2010 |
| JP | 4688444 | 2/2011 |
| JP | 2011-092765 | 5/2011 |
| JP | 2011-520805 | 7/2011 |
| JP | 2011-522575 | 8/2011 |
| JP | 2011-522695 | 8/2011 |
| JP | 2012-516224 | 7/2012 |
| JP | 2012-198134 | 9/2012 |
| JP | 2012-527318 | 11/2012 |
| JP | 2013-063308 | 4/2013 |
| JP | 5323011 | 7/2013 |
| JP | 2013-208434 | 10/2013 |
| JP | 2014-504732 | 2/2014 |
| JP | 2014-193366 | 10/2014 |
| JP | 2014-240022 | 12/2014 |
| JP | 2016-511108 | 4/2016 |
| JP | 2020-075162 | 5/2020 |
| WO | WO 94/02081 | 2/1994 |
| WO | WO 95/013765 A1 | 5/1995 |
| WO | WO 96/20742 A1 | 7/1996 |
| WO | WO 96/038174 A1 | 12/1996 |
| WO | WO 1998/030181 A1 | 7/1998 |
| WO | WO 1998/35639 | 8/1998 |
| WO | WO 1999/11244 | 3/1999 |
| WO | WO 99/26567 A1 | 6/1999 |
| WO | WO 99/56637 | 11/1999 |
| WO | WO 00/007565 A2 | 2/2000 |
| WO | WO 00/037056 A2 | 6/2000 |
| WO | WO 2000/64389 | 11/2000 |
| WO | WO 2000/64390 | 11/2000 |
| WO | WO 2000/64391 | 11/2000 |
| WO | WO 2000/64393 | 11/2000 |
| WO | WO 00/72788 A1 | 12/2000 |
| WO | WO 01/41685 | 6/2001 |
| WO | WO 2001/080825 A2 | 11/2001 |
| WO | WO 2001/97727 | 12/2001 |
| WO | WO 02/002076 A2 | 1/2002 |
| WO | WO 2002/36052 | 5/2002 |
| WO | WO 02/043785 A2 | 6/2002 |
| WO | WO 2002/053129 | 7/2002 |
| WO | WO 2002/080811 | 10/2002 |
| WO | WO 2002/087418 | 11/2002 |
| WO | WO 2002/089699 | 11/2002 |
| WO | WO 03/020172 A1 | 3/2003 |
| WO | WO 2003/073968 | 9/2003 |
| WO | WO 04/006890 A1 | 1/2004 |
| WO | WO 2004/014218 | 2/2004 |
| WO | WO 2004/043231 | 5/2004 |
| WO | WO 2004/043435 | 5/2004 |
| WO | WO 04/066871 | 8/2004 |
| WO | WO 2003/061625 | 9/2004 |
| WO | WO 2004/073552 | 9/2004 |
| WO | WO 04/098565 A2 | 11/2004 |
| WO | WO 2005/016418 | 2/2005 |
| WO | WO 2005/105197 | 11/2005 |

(56) References Cited

FOREIGN PATENT DOCUMENTS

| | | |
|---|---|---|
| WO | WO 2005/110362 | 11/2005 |
| WO | WO 05/117780 | 12/2005 |
| WO | WO 06/014434 A2 | 2/2006 |
| WO | WO 2006/036715 | 4/2006 |
| WO | WO 07/084582 | 7/2007 |
| WO | WO 2007/087061 | 8/2007 |
| WO | WO 2007/115259 A2 | 10/2007 |
| WO | WO 2007/130393 | 11/2007 |
| WO | WO 2008/005873 | 1/2008 |
| WO | WO 2008/060359 | 5/2008 |
| WO | WO 2008/083118 | 7/2008 |
| WO | WO 2008/094989 A2 | 8/2008 |
| WO | WO 2008/157614 A2 | 12/2008 |
| WO | WO 2009/012406 | 1/2009 |
| WO | WO 2009/035562 | 3/2009 |
| WO | WO 2009/035571 A2 | 3/2009 |
| WO | WO-2009035562 A2 * | 3/2009 ........... A61F 9/0017 |
| WO | WO 2009/063222 A2 | 5/2009 |
| WO | WO 2009/097468 A2 | 8/2009 |
| WO | WO 2009/126569 | 10/2009 |
| WO | WO 2009/137085 | 11/2009 |
| WO | WO 2009/151543 | 12/2009 |
| WO | WO 2010/006053 A1 | 1/2010 |
| WO | WO 10/065970 | 6/2010 |
| WO | WO 2010/077987 | 7/2010 |
| WO | WO 2010/078063 A1 | 7/2010 |
| WO | WO 2010/093945 A3 | 8/2010 |
| WO | WO 10/141729 | 12/2010 |
| WO | WO 2011/066479 | 6/2011 |
| WO | WO 2011/127064 A2 | 10/2011 |
| WO | WO 2012/019136 | 2/2012 |
| WO | WO 13/022801 | 2/2013 |
| WO | WO 2013/040079 | 3/2013 |
| WO | WO 2013/119843 A1 | 8/2013 |
| WO | WO 2014/150292 | 9/2014 |
| WO | WO 2014/150292 A1 | 9/2014 |
| WO | WO 2014/151070 | 9/2014 |
| WO | WO 2014/164569 | 10/2014 |
| WO | WO 2015/073571 | 5/2015 |
| WO | WO 2015/184173 | 12/2015 |
| WO | WO 2016/042163 A2 | 3/2016 |
| WO | WO 2016/154066 | 9/2016 |
| WO | WO 2016/187355 | 11/2016 |
| WO | WO 2017/015633 | 1/2017 |
| WO | WO 2017/040853 | 3/2017 |
| WO | WO 2017/040855 | 3/2017 |
| WO | WO 2017/053885 | 3/2017 |
| WO | WO 2017/087713 | 5/2017 |
| WO | WO 2017/184881 | 10/2017 |
| WO | WO 2019/070385 | 4/2019 |
| WO | WO 2020/172615 | 8/2020 |

OTHER PUBLICATIONS

International Search Report and Written Opinion for International Application No. PCT/US2016/053570, dated Mar. 9, 2017, in 17pages.
Bucciarelli, Patrice D., Working Model is Next Step in Team's Long Journey to Commercial Product, Healthfirst, Business First of Louisville, louisville.bizjournals.com, Feb. 27, 2004.
Emi, Kazayuki, et al., Hydrostatic Pressure of the Suprachoroidal Space, Investigative Ophthalmology & Visual Science, vol. 30, No. 2, Feb. 1989 (pp. 233-239).
Jordon, et al., "A Novel Approach to Suprachoroidal Drainage for the Surgical Treatment of Intractable Glaucoma," J Glaucoma 15(3): 200-205 (2006).
Katz, L. Jay, MD, A Call for Innovative Operations for Glaucoma, Arch Ophthalmology, Mar. 2000, vol. 118, pp. 412-413.
Rejection Decision in Chinese Application No. 201610177795.2 dated Jan. 9, 2019.
Examination Report in Australian Application No. 2018229507 dated Oct. 2, 2019.
Examination Report in Australian Application No. 2018229507 dated Mar. 20, 2019.
International Preliminary Report on Patentability in PCT/US2016/053570 dated Mar. 27, 2018.
Examination Report in Australian application No. 2015266850, dated Feb. 12, 2019.
Examination Report in Australian Application No. 2020201236, dated Jul. 8, 2020.
Search Report in European Application No. 10778286.4 dated Dec. 8, 2017.
International Search Report and Written Opinion in PCT/US2014/065283 dated Feb. 18, 2015.
Chen et al., "Implantable Unpowered Parylene MEMS Intraocular Pressure Sensor", Microtechnologies in Medicine and Biology, 2006 International Conference on Publication Date: May 9-12, 2006, 5pp., downloaded from http://ieeezxplore.ieee.org/xpl/freeabs_all.jsp?arnumber=4281361.
https://entokey.com/gonioscopy-2/ Uploaded Oct. 2016.
Jain et al., "Development of polyvinyl alcohol-gelatin membranes for antibiotic delivery in the eye", Drug Development and Industrial Pharmacy, 2011, Informa Healthcare USA, Inc., 12 pages.
Katuri et al., "Intraocular Pressure Monitoring Sensors", IEEE Sensors Journal, vol. 8, No. 1, Jan. 2008, 8 pp.
Online encyclopedia article "Hyaluronan," section on "Medical Applications" accessed Monday, Sep. 27, 2010. http://en.wikipedia.org/wiki/Hyaluronic_acid.
Rizq, et al., "Intraocular Pressure measurement at the Chroid Surface: A Feasibility Study with Implications for Implantable Microsystems", Br J Ophthalmol 2001; 85:868-871, Jul. 2001.
Ianchulev et al., "Minimally Invasive Ab-Interno Suprachoroidal Device (CyPass) for IOP Control in Open-Angle Glaucoma," presented at the Annual Meeting of the American Academy of Ophthalmology Oct. 16-19, 2010, Chicago, IL.
Ianchulev, Chapters: Suprachoroidal Space as a Therapeutic Target, in J.R. Samples & I.I.K. Ahmed (eds.), Surgical Innovations in Glaucoma 33 (Springer Science+Business Media 2014).
Walter et al., "Development of a Completely Encapsulated Intraocular Pressure Sensor", Ophthalmic Res 2000; 32:278-284. Nov. 5, 1999.
Supplementary European Search Report in related European application No. 04779911.9, dated Jul. 18, 2007, 3 pp.
Office Action in related European application No. 04779911.9, dated Apr. 17, 2009, 4 pp.
Office Action in corresponding EP Application No. 04779911.9 dated Sep. 30, 2010, 4 pp.
Second Office Action in Chinese Application No. 201080032278.7 dated Nov. 15, 2014.
Office Action in European Application No. 18153863.8 dated Oct. 19, 2018.
Decision to Grant a Patent in Japanese Application No. JP 2021-024879, dated Jul. 20, 2022, 8 pages.
Canadian Office Action for Application No. 2,901,476, dated Nov. 13, 2020, in 5 pages.
Extended Search Report in European Application No. 18183395.5 dated Nov. 14, 2018.
Extended Search Report in European Application No. 18153863.8 dated Jun. 5, 2018.
International Search Report and Written Opinion in PCT/US2011/061967 dated Jun. 28, 2012.
International Search Report and Written Opinion in PCT/US2016/049996 dated Dec. 16, 2016.
International Search Report and Written Opinion, PCT/US2017/028665, dated Jul. 31, 2017.
International Preliminary Report on Patentability in PCT/US2016/049996 dated Mar. 6, 2018.
International Preliminary Report on Patentability, PCT/US2017/028665, dated Oct. 23, 2018.
International Search Report and Written Opinion for Application No. PCT/US2020/54619, dated Jan. 12, 2021, in 8 pages.
Rejection Decision in Japanese Application No. 2012-511975 dated Jan. 9, 2015.
Examination Report in Japanese Application No. 2016-221183 dated Feb. 8, 2019.

(56) References Cited

OTHER PUBLICATIONS

Office Action in Japanese Application No. 2018-211032 dated Nov. 6, 2019.

* cited by examiner

PUNCTAL IMPLANTS WITH CONTROLLED DRUG DELIVERY FEATURES AND METHODS OF USING SAME

CROSS-REFERENCE TO RELATED APPLICATIONS

This application is a national stage application under 35 U.S.C. § 371 of International Application No. PCT/US2016/053570, filed on Sep. 23, 2016, which the benefit of U.S. Provisional Application No. 62/233,259, filed on Sep. 25, 2015, the entire contents of which are incorporated by reference herein.

BACKGROUND

Field

This disclosure relates to implantable drug delivery devices structured to provide targeted and/or controlled release of a drug to a desired ocular target tissue and methods of using such devices for the treatment of ocular diseases and disorders. In certain embodiments, this disclosure relates to devices for insertion into the punctum and for delivery of a therapeutic agent or agents to the eye in a controlled manner.

Description of the Related Art

The mammalian eye is a specialized sensory organ capable of light reception and is able to receive visual images. The retina of the eye consists of photoreceptors that are sensitive to various levels of light, interneurons that relay signals from the photoreceptors to the retinal ganglion cells, which transmit the light-induced signals to the brain. The iris is an intraocular membrane that is involved in controlling the amount of light reaching the retina. The iris consists of two layers (arranged from anterior to posterior), the pigmented fibrovascular tissue known as a stroma and pigmented epithelial cells. The stroma connects a sphincter muscle (sphincter pupillae), which contracts the pupil, and a set of dilator muscles (dilator pupillae) which open it. The pigmented epithelial cells block light from passing through the iris and thereby restrict light passage to the pupil.

Numerous pathologies can compromise or entirely eliminate an individual's ability to perceive visual images, including trauma to the eye, infection, degeneration, vascular irregularities, and inflammatory problems. The central portion of the retina is known as the macula. The macula, which is responsible for central vision, fine visualization and color differentiation, may be affected by age related macular degeneration (wet or dry), diabetic macular edema, idiopathic choroidal neovascularization, or high myopia macular degeneration, among other pathologies.

Other pathologies, such as abnormalities in intraocular pressure, can affect vision as well. Aqueous humor is a transparent liquid that fills at least the region between the cornea, at the front of the eye, and the lens and is responsible for producing a pressure within the ocular cavity. Normal intraocular pressure is maintained by drainage of aqueous humor from the anterior chamber by way of a trabecular meshwork which is located in an anterior chamber angle, lying between the iris and the cornea or by way of the "uveoscleral outflow pathway." The "uveoscleral outflow pathway" is the space or passageway whereby aqueous exits the eye by passing through the ciliary muscle bundles located in the angle of the anterior chamber and into the tissue planes between the choroid and the sclera, which extend posteriorly to the optic nerve. About two percent of people in the United States have glaucoma, which is a group of eye diseases encompassing a broad spectrum of clinical presentations and etiologies but unified by increased intraocular pressure. Glaucoma causes pathological changes in the optic nerve, visible on the optic disk, and it causes corresponding visual field loss, which can result in blindness if untreated. Increased intraocular pressure is the only risk factor associated with glaucoma that can be treated, thus lowering intraocular pressure is the major treatment goal in all glaucomas, and can be achieved by drug therapy, surgical therapy, or combinations thereof.

Many pathologies of the eye progress due to the difficulty in administering therapeutic agents to the eye in sufficient quantities and/or duration necessary to ameliorate symptoms of the pathology. Often, uptake and processing of the drug component of the therapeutic agent occurs prior to the drug reaching an ocular target site. Due to this metabolism, systemic administration may require undesirably high concentrations of the drug to reach therapeutic levels at an ocular target site. This can not only be impractical or expensive, but may also result in a higher incidence of side effects. Topical administration is potentially limited by limited diffusion across the cornea, or dilution of a topically applied drug by tear-action. Even those drugs that cross the cornea may be unacceptably depleted from the eye by the flow of ocular fluids and transfer into the general circulation. Thus, a means for ocular administration of a therapeutic agent in a controlled and targeted fashion would address the limitations of other delivery routes.

SUMMARY

In several embodiments, the implants disclosed herein operate to provide a therapeutic effect in the eye of a subject based, at least in part, on a physical arrangement of drugs within the implant. In several embodiments, the implants comprise a punctual plug and the physical arrangement of the drugs within the implant provides advantageous timing of delivery of the drugs. The punctal implants disclosed herein are placed into the punctum and reside at least partially in a lacrimal canaliculus of an eye. Such an approach is useful, in several embodiments, such as when steroid and cyclosporine are combined to treat dry eye. Many current therapies for dry eye employ an initial treatment with steroid eye drops for a first time period (e.g., two weeks). After the initial period cyclosporine eye drops are added to the treatment regimen. Thereafter the steroid is then tapered off, ending at day 60 and cyclosporine therapy is continued alone, as long as needed. However, according to one embodiment disclosed herein, a punctal implant can deliver steroid and cyclosporine with appropriate timing to achieve a near constant, zero order administration of drug. Such a dosing profile is generally considered more efficient than bolus delivery, such as occurs with eye drops.

In several embodiments employing multiple drugs, the second (or third, etc.) agent results in synergistic effects when combined with the first agent. In other embodiments, the second agent reduces one or more side effects associated with the first agent. It is understood, however, that any embodiment of implant disclosed herein may contain only one drug.

As such, several embodiments provide for implants for insertion into a punctum of the eye of a subject, comprising an outer shell having a proximal end, a distal end, the outer shell being shaped to define an interior lumen, the outer shell dimensioned for insertion into the punctum of the eye of a subject, at least a first drug positioned within the interior lumen, at least one region of drug release the proximal portion of outer shell, and a distal occlusive member within the inner lumen, the distal occlusive member preventing elution of the first drug from the distal end of the implant.

In several such embodiments, the first drug elutes from the lumen to the tear film of the eye of the subject by passing through the at least one region of drug release. In some embodiments, the implant is dimensioned to be implanted with the distal end of the outer shell positioned in the lacrimal duct. In some embodiments, the implant is dimensioned to be implanted with the distal end of the outer shell positioned in the lacrimal sac. In several embodiments, the implant is dimensioned to be implanted with the distal end of the outer shell positioned in the nasolacrimal duct.

In several embodiments, there is also provided a punctal implant for insertion into a punctum of the eye of a subject and configured to deliver two or more drugs to the eye of the subject, the implant comprising an outer shell comprising (i) proximal end comprising at least one region of drug release and a flange, (ii) a closed distal end, and (iii) an interior lumen comprising at least two drugs positioned within the lumen.

In several embodiments, there is also provided a punctal implant for insertion into a punctum of the eye of a subject and configured to deliver two or more drugs to the eye of the subject, the implant comprising an outer shell comprising (i) a proximal end comprising at least one region of drug release and a flange, (ii) a closed distal end, and (iii) an interior lumen comprising at least two drugs positioned within the lumen, wherein the region of drug release comprises aperture through an annular ring positioned at the proximal-most portion of the interior lumen, wherein said aperture allows elution of the two or more drugs to occur only through the occlusive member, wherein the dimensions of the aperture at least partially defines the elution rate of the two or more drugs, wherein the flange is configured to rest on the surface of the eyelid when the implant is inserted into the punctum, and wherein the first and second drug elute from the lumen to the tear film of the eye of the subject by passing through the at least one region of drug release.

In several embodiments, the at least one region of drug release comprises at least one aperture. Additionally, in some embodiments, the implant further comprises at least one membrane that occludes the at least one aperture, wherein the membrane is permeable to the at least a first drug, wherein the membrane allows elution of the at least a first drug to occur only through the at least one membrane.

In several embodiments, the at least one region of drug release comprises a plurality of apertures through the outer shell and positioned randomly or in a patterned array throughout the proximal portion of the implant. As above, at least a portion of the plurality of apertures is occluded by a membrane permeable to the first drug.

Some embodiments provided for herein result in elution of drug (or drugs) from the implant with zero-order or pseudo zero-order kinetics.

In some embodiments, the intraocular target is the posterior chamber of the eye, the anterior chamber of the eye, both the anterior chamber and posterior of the eye, or the macula, the retina, the optic nerve, the ciliary body, and the intraocular vasculature.

In several embodiments, the drug acts on the intraocular target tissue to generate a therapeutic effect for an extended period. In one embodiment, the drug comprises a steroid. In such embodiments, the implant contains a total load of steroid ranging from about 10 to about 1000 micrograms, steroid is released from the implant at a rate ranging from about 0.05 to about 10 micrograms per day and/or the steroid acts on the diseased or damaged target tissue at a concentration ranging from about 1 to about 100 nanomolar. In some embodiments, the steroid additionally generates side effects associated with accumulation of physiologic fluid, and an optional shunt transports the accumulated fluid from the first location to the remote second location (such as, for example, from the anterior chamber to an existing physiological outflow pathway, such as Schlemm's canal or the naso-lacrimal duct).

In several embodiments, the at least one region of drug release comprises an occlusive member that is permeable to said two or more drugs, and the occlusive member allows elution of the two or more drugs to occur through the occlusive member. In several embodiments, the thickness of the occlusive member at least partially defines the elution rate of the drug (or drugs). In several embodiments, having a flange, the flange is configured to rest on the surface of the eyelid when the implant is inserted into the punctum. In several embodiments, the drug (or drugs) elute from the lumen to the tear film of the eye of the subject by passing through the at least one region of drug release.

In several embodiments, the occlusive member is an occlusive membrane is dimensioned based on the permeability of said occlusive member to said first drug (and second or more) and the desired relative timing and duration of elution of said first and second drugs. In several embodiments, the occlusive member has a thickness of between about 0.0001 and 0.0005 inches. In certain embodiments, occlusive member is integrally formed with the outer shell of the implant. In some embodiments, the occlusive member further comprises randomly or patterned holes through the occlusive membrane.

In some embodiments, a first drug is placed in a more proximal position within the interior lumen relative to the position of a second drug. In some embodiments, a third drug is included, and in certain such embodiments, the first drug and second drug are positioned adjacent to one another and both the first and second drugs are placed in a more proximal position within the interior lumen relative to the position of the third drug.

In several embodiments, the drug (or drugs) is formulated as tablets, as a nanodispersion, or a combination thereof. In some embodiments, a first drug is formed as a discontinuous first phase and a second drug is formulated as dispersion of solid of liquid particles into which the first drug is dispersed.

In several embodiments, the outer shell of the implant comprises a bulge in the distal region in order to anchor the implant in the punctum.

In several embodiments, a first drug elutes from an implant for a period of between 1 and 75 days, and a second drug elutes for a period of time ranging from about 1 to about 24 months after the first drug is eluted.

In several embodiments, the implants disclosed herein have a length of between about 0.5 and about 2.5 mm. Some embodiments of the implants have a length of about 1.4 to about 1.6 mm. Some embodiments of the implant have a diameter of about 0.2 to about 1.5 mm. Some embodiments of the implant have a diameter of about 0.2 to about 0.6 mm.

Depending on the embodiment, the first drug may be a steroid. In some such embodiments, the steroid is selected from the group consisting of loteprednol etabonate, dexamethasone, and triamcinolone acetonide. In some embodiments, a second drug is cyclosporine and is optionally formulated as a nanodispersion. In several embodiments, the first drug is cyclosporine A. In several embodiments, the first drug facilitates tear production.

Several embodiments optionally comprise a retention protrusion configured to anchor the implant in an implantation site (e.g., the punctum). Such retention protrusions optionally comprise one or more of bulges, ridges, claws, threads, flexible ribs, rivet-like shapes, flexible barbs, barbed tips, expanding material (such as a hydrogel), and biocompatible adhesives. In some embodiments, the expanding material is placed on an exterior surface of the outer shell of the implant and expands after contact with a solvent, such as, for example, intraocular fluid or tear film.

BRIEF DESCRIPTION OF THE DRAWINGS

These and other features, aspects, and advantages of the present disclosure will now be described with reference to the drawings of embodiments, which embodiments are intended to illustrate and not to limit the disclosure. One of ordinary skill in the art would readily appreciated that the features depicted in the illustrative embodiments are capable of combination in manners that are not explicitly depicted, but are both envisioned and disclosed herein.

DETAILED DESCRIPTION

Figure 1A:
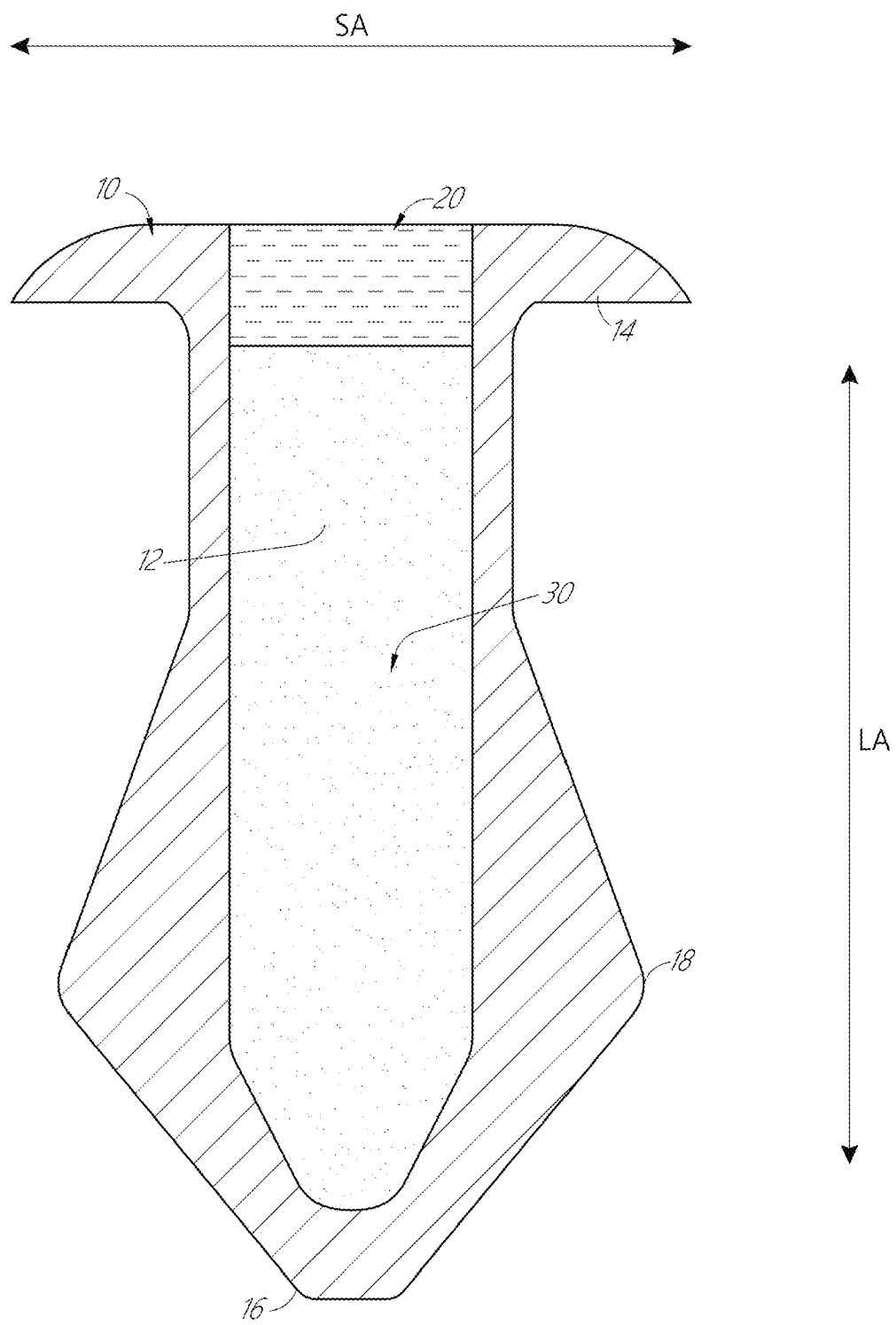
FIG. 1A illustrates a schematic cross section of an implant in accordance with embodiments disclosed herein.

Achieving local ocular administration of a drug may require direct injection or application, but could also include the use of a drug eluting implant, a portion of which, could be positioned in close proximity to the target site of action within the eye or within the chamber of the eye where the target site is located (e.g., anterior chamber, posterior chamber, or both simultaneously). Use of a drug eluting implant could also allow the targeted delivery of a drug to a specific ocular tissue, such as, for example, the macula, the retina, the ciliary body, the optic nerve, or the vascular supply to certain regions of the eye. Use of a drug eluting implant could also provide the opportunity to administer a controlled amount of drug for a desired amount of time, depending on the pathology. For instance, some pathologies may require drugs to be released at a constant rate for just a few days, others may require drug release at a constant rate for up to several months, still others may need periodic or varied release rates over time, and even others may require periods of no release (e.g., a "drug holiday"). Further, implants may serve additional functions once the delivery of the drug is complete. Implants may maintain the patency of a fluid flow passageway within an ocular cavity, they may function as a reservoir for future administration of the same or a different therapeutic agent, or may also function to maintain the patency of a fluid flow pathway or passageway from a first location to a second location, e.g. function as a stent. Conversely, should a drug be required only acutely, an implant may also be made completely biodegradable.

In several embodiments, the implants are configured specifically for use (e.g., implantation) in the punctum of the eye of a subject (e.g., the upper and/or lower punctum of the upper and/or lower canaliculus, respectively). The puncta function to collect tears that are released onto the surface of the eye by the lacrimal glands. However, in some individuals tear production is reduced, blocked, decreased, or otherwise insufficient to maintain an adequate level of moisture on the eye (or eyes). Damage to the corneal surface of the eye can result if the moisture on the eye remains reduced. When functioning normally (e.g., in a patient with normal tear production), the puncta convey the tear fluid to the lacrimal sac, which then allows it to drain through the nasolacrimal duct to the inner nose. One treatment for dry eye or similar syndromes is implantation of punctual plugs. Once implanted the plugs function to block the drainage of tear fluid, thereby increasing the retention of tear fluid on the eye. However, several of the implant embodiments disclosed herein advantageously allow the supplementation of the physical blockage of tear drainage with the delivery of one or more therapeutic agents to the eye in order to treat one or more aspects of reduced tear production. Thus, in several embodiments, one or more therapeutic agents are positioned in the implant in order to increase tear production and/or treat a symptom of dry eye, including, but not limited to, reduction in swelling, irritation of the eye and surrounding tissues and/or inflammation. Additional symptoms that are reduced, ameliorated, and in some cases eliminated include stinging or burning of the eye, a sandy or gritty feeling as if something is in the eye, episodes of excess tears following very dry eye periods, a stringy discharge from the eye, pain and redness of the eye, temporary or extended episodes of blurred vision, heavy eyelids, reduced ability to cry, discomfort when wearing contact lenses, decreased tolerance of reading, working on the computer, or any activity that requires sustained visual attention, and eye fatigue.

In several embodiments, the implants advantageously obviate the need for additional topical agents (e.g., ointments, artificial tears, etc.). In several embodiments, however, the implants are configured have a particular drug release profile) to work synergistically with one or more of such agents. For example, in several embodiments, the implant is configured to deliver a constant dosage of a therapeutic agent over time to treat a damaged or diseased eye, and a subject with them implants in place can also use artificial tears, for example, to further enhance the efficacy of the agent delivered from the implant.

In several embodiments, the agents delivered from the implant are used for treatment of another ocular disorder, such as glaucoma, ocular hypertension, and/or elevated intraocular pressure.

Advantageously, as discussed herein, several embodiments of the implants configured for punctual placement allows metered delivery of one or more therapeutic agents; that is, delivery at a constant rate, thereby reducing the peaks and valleys of therapeutic agent concentration as occurs with topical administration (e.g., via eye drop).

Any of the relevant features disclosed herein can be applied to the embodiments configured for use in the punctum. For example, the dimensions of the implants, their shape, their drug release characteristics, and the like can be configured for use in the punctum. In several embodiments, the plugs can be tailored to the punctal dimensions of a particular subject. Moreover, the plugs can be configured to be removable or, in several embodiments, permanent (e.g., capable of being recharged). In several embodiments, the punctal implants comprise at least a first active agent that is loaded, at least in part, preferentially in the proximal region of the implant (e.g., such that the agent is released to the tear film of the subject) with the distal region of the implant positioned within the within the lacrimal ducts. In several such embodiments, the implant is specifically adapted to prevent unintended release of the active agent (or agents) from the distal portion of the implant. In some such embodiments, a plug (e.g., an impermeable occlusive member), a membrane (e.g., a membrane with little to no permeability to the active agent/agents), and/or a valve (e.g., a one-way valve) prevent elution in a distal region of the device.

In several embodiments, the use of a valve or plug enables flushing of the implant. For example, if there is a need to replace the therapeutic agent (e.g., with a different agent or a different dose of the same agent) it may be beneficial to substantially remove any remaining agent within the implant. In such instances, the plug can be removed and the implant flushed from a proximal to distal direction, allowing the therapeutic agent remaining in the implant to be flushed down the nasolacrimal duct. Thereafter the implant can be reloaded with another dose, another agent, and the like. Similarly, flushing the implant can be performed when a valve is positioned in the distal region of the implant, the valve being opened by pressure exerted on it from the flushing procedure and preventing backflow of the flushed agent into the implant.

In several embodiments, an implant and method for treating an eye with latanoprost or other therapeutic agent(s) is provided, the method comprising inserting a distal end of an implant into at least one punctum of the eye and positioning the implant such that the proximal portion of the implant delivers latanoprost or other therapeutic agents) to the tear fluid adjacent the eye. In several embodiments, delivery of the latanoprost or other therapeutic agent(s) is inhibited distally of the proximal end.

Implants according to the embodiments disclosed herein preferably do not require an osmotic or ionic gradient to release the drug(s), are implanted with a device that minimizes trauma to the healthy tissues of the eye which thereby reduces ocular morbidity, and/or may be used to deliver one or more drugs in a targeted and controlled release fashion to treat multiple ocular pathologies or a single pathology and its symptoms. However, in certain embodiments, an osmotic or ionic gradient is used to initiate, control (in whole or in part), or adjust the release of a drug (or drugs) from an implant. In some embodiments, osmotic pressure is balanced between the interior portion(s) of the implant and the ocular fluid, resulting in no appreciable gradient (either osmotic or ionic). In such embodiments, variable amounts of solute are added to the drug within the device in order to balance the pressures.

As used herein, "drug" refers generally to one or more drugs that may be administered alone, in combination and/or compounded with one or more pharmaceutically acceptable excipients (e.g. binders, disintegrants, fillers, diluents, lubricants, drug release control polymers or other agents, etc.), auxiliary agents or compounds as may be housed within the implants as described herein. The term "drug" is a broad term that may be used interchangeably with "therapeutic agent" and "pharmaceutical" or "pharmacological agent" and includes not only so-called small molecule drugs, but also macromolecular drugs, and biologics, including but not limited to proteins, nucleic acids, antibodies and the like, regardless of whether such drug is natural, synthetic, or recombinant. Drug may refer to the drug alone or in combination with the excipients described above. "Drug" may also refer to an active drug itself or a prodrug or salt of an active drug.

In some embodiments, the drug diffuses through the implant itself and into the intraocular environment. In several embodiments, the outer material of the implant is permeable or semi-permeable to the drug (or drugs) positioned within an interior lumen, and therefore, at least some portion of the total elution of the drug occurs through the shell itself. In other embodiments, however, the shell of the implant is impermeable to the drug (or drugs) in the interior lumen, and the implant comprises one or more specific regions of drug release. The term "permeable" and related terms (e.g. "impermeable" or "semi permeable") are used herein to refer to a material being permeable to some degree (or not permeable) to one or more drugs or therapeutic agents and/or ocular fluids. The term "impermeable" does not necessarily mean that there is no elution or transmission of a drug through a material, instead such elution or other transmission is negligible or very slight, e.g. less than about 3% of the total amount, including less than about 2% and less than about 1%. However, in sonic embodiments, an impermeable outer shell permits no elution of drug through the shell.

As used herein, "patient" shall be given its ordinary meaning and shall also refer to mammals generally. The term "mammal", in turn, includes, but is not limited to, humans, dogs, cats, rabbits, rodents, swine, ovine, and primates, among others. Additionally, throughout the specification ranges of values are given along with lists of values for a particular parameter. In these instances, it should be noted that such disclosure includes not only the values listed, but also ranges of values that include whole and fractional values between any two of the listed values.

In several embodiments, the drug delivery implants disclosed herein are configured to delivery drug to the eye via a topical delivery route. In some embodiments, the implant is configured to deliver one or more drugs to anterior region of the eye in a controlled fashion while in other embodiments the implant is configured to deliver one or more drugs to the posterior region of the eye in a controlled fashion. In still other embodiments, the implant is configured to simultaneously deliver drugs to both the anterior and posterior region of the eye in a controlled fashion. In yet other embodiments, the configuration of the implant is such that drug is released in a targeted fashion to a particular intraocular tissue, for example, the macula or the ciliary body. It will be appreciated that each of the embodiments described herein may target one or more of these regions and, optionally, reaches the site and achieves a therapeutic effect after being administered topically. Following implantation at the desired site within the eye, such as the punctum, drug is released from the implant in a targeted and controlled fashion, based on the design of the various aspects of the implant, preferably for an extended period of time. The implant and associated methods disclosed herein may be used in the treatment of pathologies requiring drug administration to the surface of the eye (e.g., topical), the posterior chamber of the eye, the anterior chamber of the eye, or to specific tissues within the eye.

The present disclosure relates to ophthalmic drug delivery implants which, following implantation at an implantation site, such as the punctum, provide controlled release of one or more drugs to a desired target region within the eye, the controlled release optionally being for an extended, period of time. Various embodiments of the implants are shown in the accompanying figures and will be referred to herein.

In several embodiments, a biocompatible drug delivery ocular implant is provided that comprises an outer shell that is shaped to define at least one interior lumen that houses a drug for release into an ocular space.

As shown in FIG. 1, which is a cross-section of a punctal plug drug delivery system according to several embodiments, disclosed herein, the implant comprises a body 10 having an interior lumen 12. In several embodiments, the shell is formed to have at least two interior lumens. The upper portion of the implant, in several embodiments, comprises a flange 14 that extends radially and sits on the surface of the eyelid after the plug is implanted into the punctum. Opposite the flange 14 is a closed end 16. However, in some embodiments, an open end (or open lateral portion) may also be used, for example to provide drainage to the nasolacrimal duct. In several embodiments, the implant comprises a radial bulge 18 from a long axis LA of the body in order to provide an anchor within the punctum. In several embodiments, the bulge is parallel (or substantially parallel to a short axis SA of the implant). In additional embodiments, the bulge (or other pattern) need not be uniform. For example, in several embodiments, the bulge can comprise a raised ridge (or series of ridges encircling the body). In one embodiment, the bulge is similar to threads on a screw. Other surface irregularities may be used in place of, or in combination with a bulge, for example, a ridge, groove, relief, hole, or annular groove, barbs, barbs with holes, screw-like elements, knurled elements, suture, friction or wedge fit, and/or expandable materials.

Figure 1B:
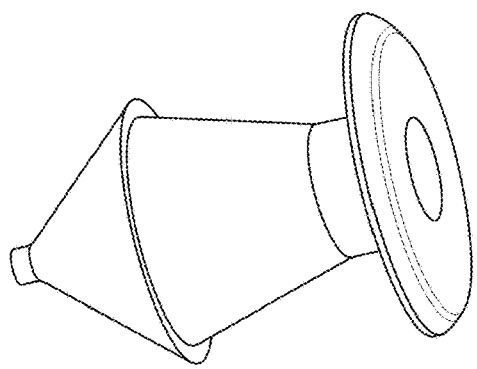
FIGS. 1B-1D illustrate additional embodiments of an implant in accordance with embodiments disclosed herein.
Figure 1C:
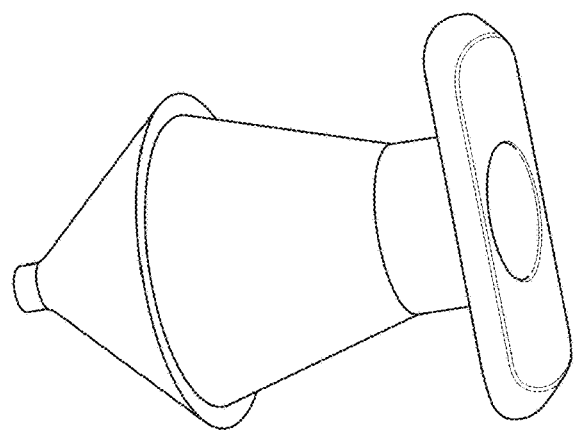
Figure 1D:
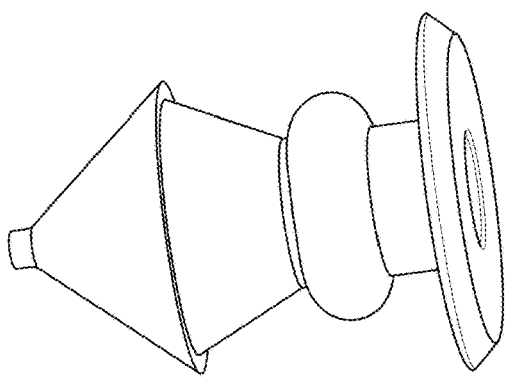

In several embodiments, the upper portion of the implant comprises a flange with a diameter configured to ensure reduced, limited, or in some embodiments, no corneal or scleral contact. The flange preferably has a generally flattened lower surface to allow it to rest upon the lower eyelid immediately adjacent to the punctum. FIG. 1B illustrates a flange 14 that is circular in shape, while FIG. 1C illustrates an asymmetrical flange, and FIG. 1D illustrates an ovoid flange. Attributes of the flange, such as area, shape, and thickness may be varied as desired such as to aid in positioning of the uppermost end of the implant at the surface of the punctum. The flange may be round, ovoid, or any geometric or asymmetric shape. In several embodiments, the flange is asymmetrical to provide reduced, limited, or in some embodiments, no corneal or scleral contact. Illustrations of non-limiting embodiments of an asymmetric flange can also be seen in FIGS. 15A and 18A.

Figure 14A:
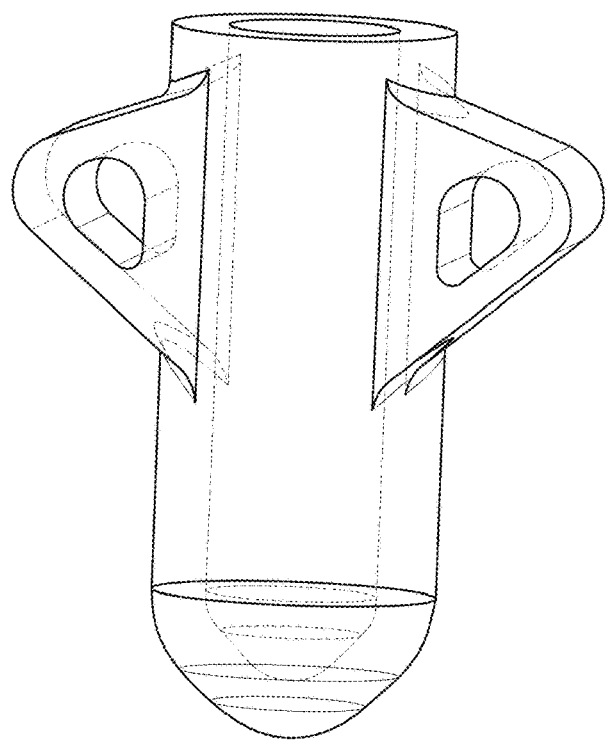
FIGS. 14A-14B illustrate schematic cross sections of additional embodiments of implants in accordance with disclosure herein.
Figure 14B:
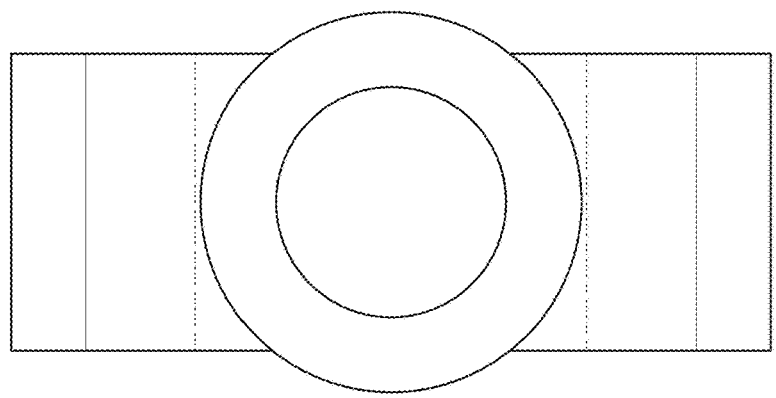
Figure 15A:
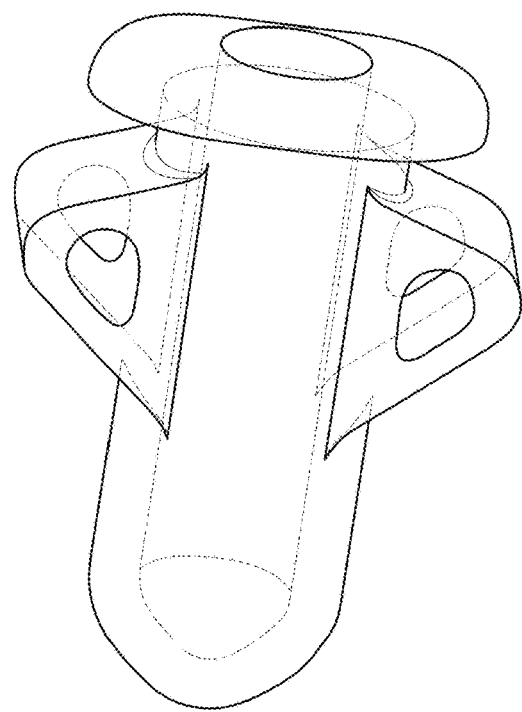
FIGS. 15A-15B illustrate schematic cross sections of additional embodiments of implants in accordance with disclosure herein.
Figure 15B:
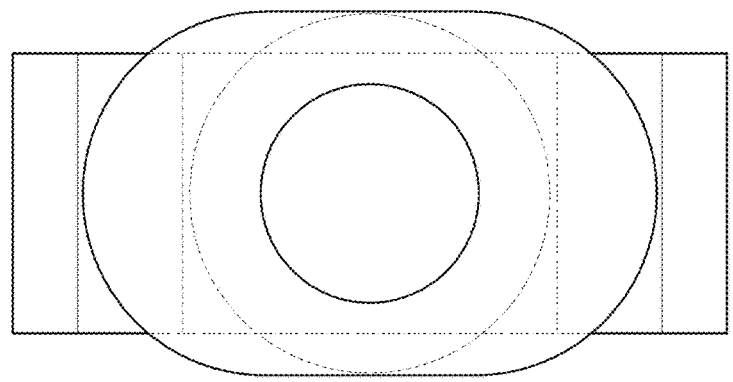
Figure 16A:
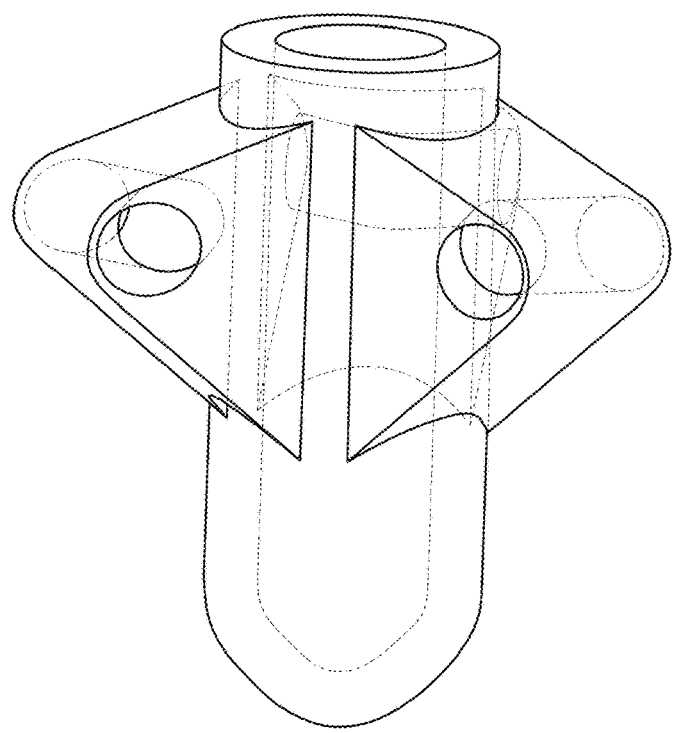
FIGS. 16A-16B illustrate schematic cross sections of additional embodiments of implants in accordance with disclosure herein.
Figure 16B:
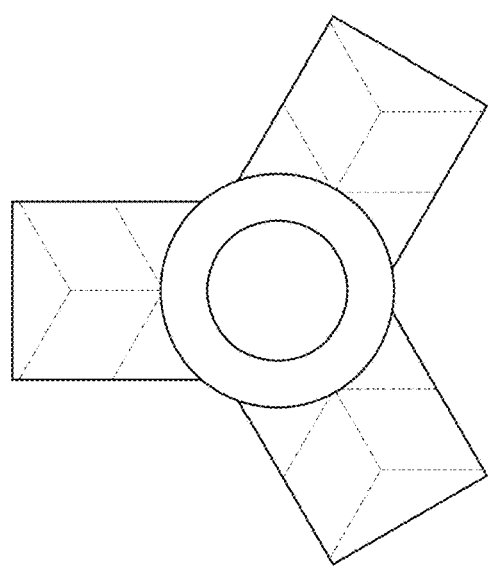
Figure 17A:
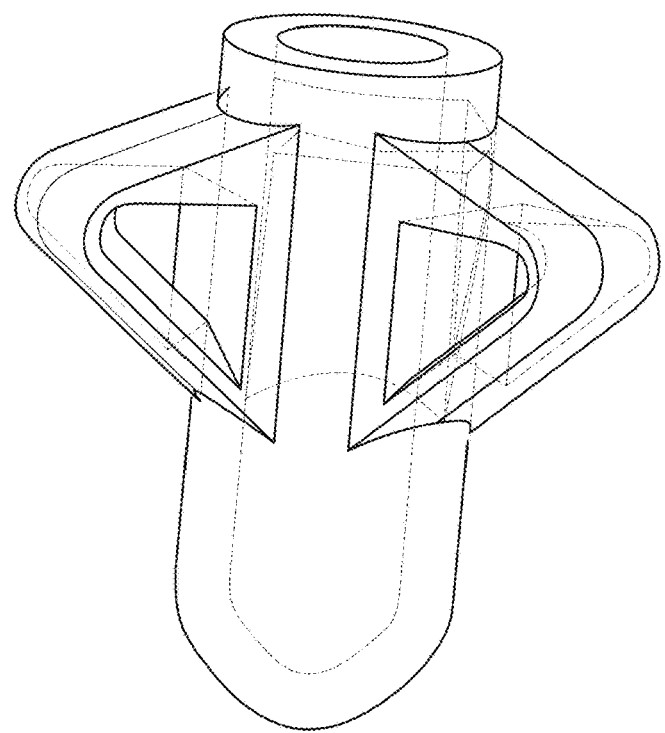
FIGS. 17A-17B illustrate schematic cross sections of additional embodiments of implants in accordance with disclosure herein.
Figure 17B:
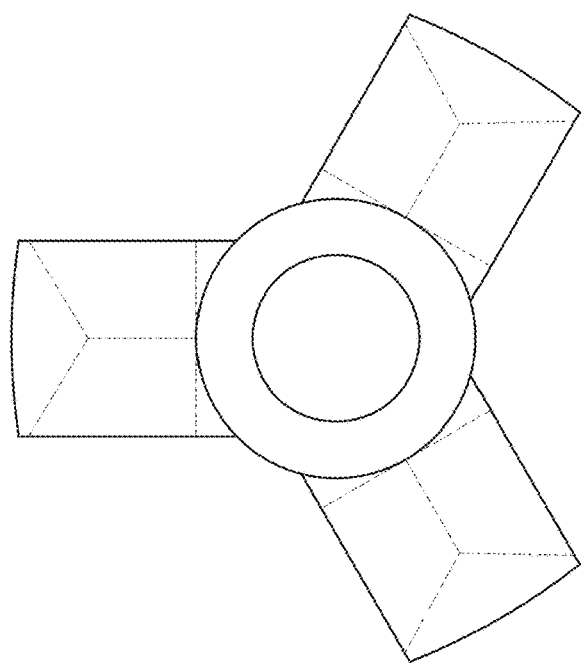
Figure 18A:
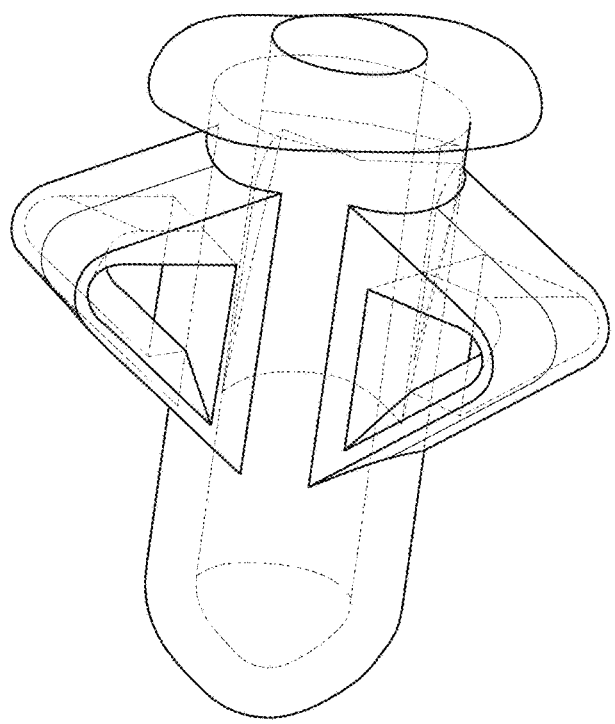
FIGS. 18A-18B illustrate schematic cross sections of additional embodiments of implants in accordance with disclosure herein.
Figure 18B:
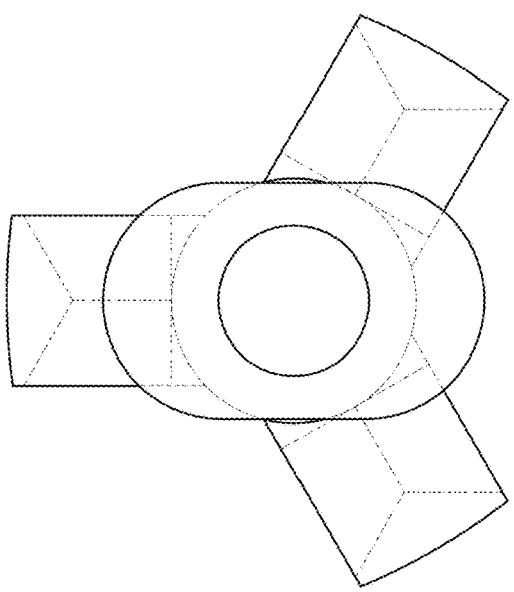
Figure 19A:
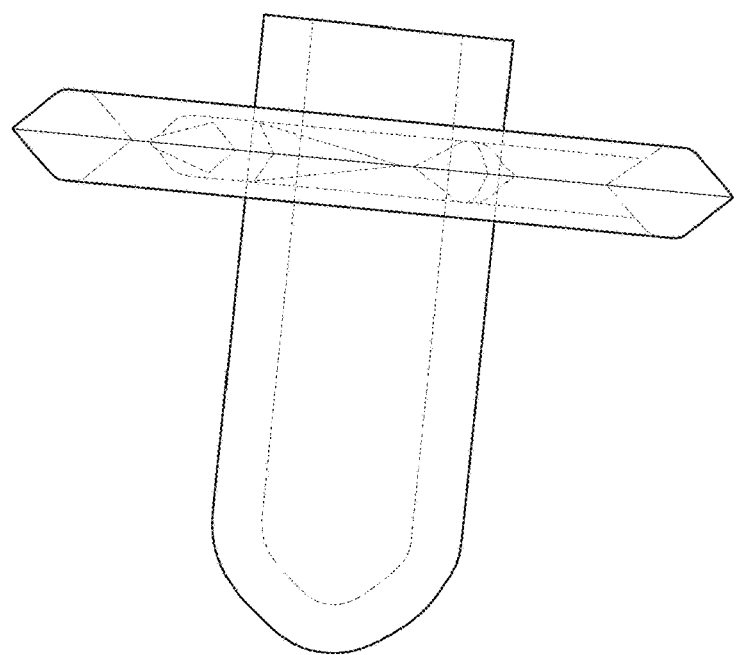
FIGS. 19A-19B illustrate schematic cross sections of additional embodiments of implants in accordance with disclosure herein.
Figure 19B:
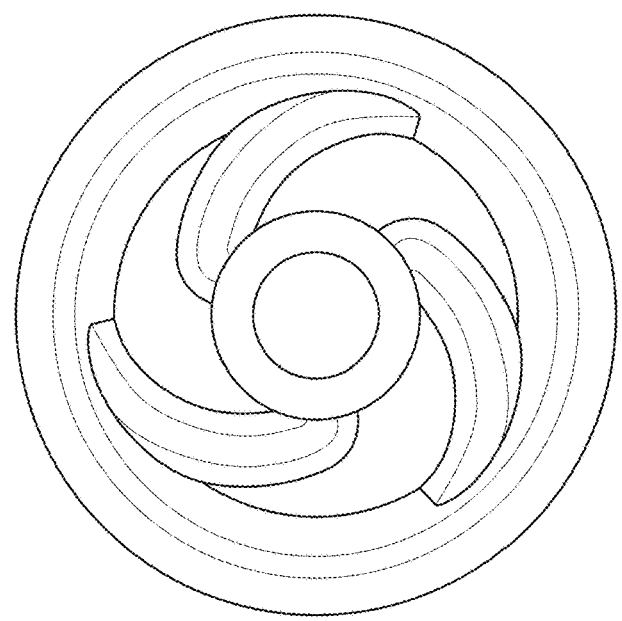

Several embodiments optionally comprise at least one retention protrusion configured to anchor the implant in an implantation site. In several embodiments, these retention features are non-occlusive, for example, they allow tear or other fluid flow through the canaliculus toward the nasolacrimal duct while holding the tissue of the canaliculus away from the implant body. In several embodiments, the at least one retention feature optionally comprises a bulge, protuberance, or other change in shape (relative to the long axis of the implant body) that extends axially from the body and that holds the implant in position. In several embodiments, the implant further comprises an inner tubular passageway of any size and shape. For example, FIGS. 14A and 14B illustrate a non-limiting embodiment comprising two retention features extending axially from the body of the implant, each further comprising a straight tubular passageway that passes through the feature. FIGS. 15A and 15B depict an additional embodiment, further comprising an asymmetric flange. FIGS. 16A and 16B illustrates another embodiment of an implant comprising three retention features, each further comprising an elbow-shaped inner tubular passageway. In several embodiments, the at least one retention feature optionally comprises a bulge that extends axially from the body of the implant and comprises an inner relief, as illustrated in FIGS. 17A, 17B. FIGS. 18A and 18B illustrate another embodiment of an implant comprising three retention features, each further comprising an inner relief, and an asymmetric flange. In such embodiments, the inner relief can be of any shape and size, advantageously facilitating an optionally greater tear or other fluid flow as compared to retention features comprising a tubular passageway. In several embodiments, the relief features may also provide a point through which a securing suture can be fastened to secure the implant into position. Additonally, some such embodiments are used in conjunction with therapeutic agents having a side effect of increased tear production. In several embodiments, the retention features optionally comprise an erodible material. In several embodiments, the retention protrusions extend from the proximal end of the implant to a position approximately or more than halfway down the (long axis of the) implant towards the distal end. In some embodiments, the retention protrusions extend from the proximal end of the implant to less than halfway to the distal end of the implant. In some embodiments, the retention protrusion comprises a ring positioned at any point along the body of the implant, as shown, for example, in FIG. 19A. In such embodiments, the ring optionally contains spoke features, occluding some, but not all, fluid flow, as shown, for example, in FIG. 19B. Again, these retention features and flange shapes may be incorporated into any of the embodiments of FIGS. 1-7.

In several embodiments, the dimension of the at least one retention feature ranges from about 0.01 mm to about 0.15 mm as measured from the outer surface of the implant body to an edge of retention feature. The thickness of the retention feature, in some embodiments, ranges from about 0.01 mm to about 0.02 mm about 0.02 mm to about 0.03 mm, about 0.03 mm to about 0.04 mm, about 0.04 mm to about 0.05 mm , about 0.05 mm to about 0.06 mm, about 0.06 mm to about 0.07 mm, about 0.07 mm to about 0.08 mm, about 0.08 mm to about 0.09 mm, about 0.09 mm to about 0.10 mm, about 0.10 mm to about 0.11 mm, about 0.11 mm to about 0.12 mm, about 0.12 mm to about 0.13 mm, about 0.13 mm to about 0.14 mm, about 0.14 mm to about 0.15 mm, and overlapping ranges therebetween and/or any other dimensions sufficient to secure the implant in the punctum of a particular patient.

In several embodiments, the long axis of the implant is greater than the short axis of the implant. In several embodiments, the ratio of the long axis to the short axis ranges from about 1:1 to about 2:1, about 2:1 to about 3:1, about 3:1 to about 4:1, about 4:1 to about 5:1, about 5:1 to about 6:1, about 6:1 to about 7:1, about 7:1 to about 8:1, about 8:1 to about 9:1, about 9:1 to about 10:1, about 10:1 to about 20:1, or ratios between (or greater) than those listed.

In several embodiments, the punctal implant ranges between about 0.5 and about 2.5 mm long (e.g., from the proximal end to the distal end). The length of the implant, in some embodiments, ranges from about 0.5 mm to about 0.7 mm, about 0.7 mm to about 0.9 mm, about 0.9 mm to about 1.0 mm, about 1.0 mm to about 1.1 mm, about 1 1 mm to about 1.2 mm, about 1.2 mm to about 1.3 mm, about 1.3 mm to about 1.35 mm, about 1.35 mm to about 1.4 mm, about 1.4 mm to about 1.45 mm, about 1.45 mm to about 1.5 mm, about 1.5 mm to about 1.55 mm, about 1.55 mm to about 1.6 mm, about 1.6 mm to about 1.65 mm, about 1.65 mm to about 1.7 mm, about 1.7 mm to about 1.9 mm, about 1.9 mm to about 2.1 mm, about 2.1 mm to about 2.3 mm, about 2.3 mm to about 2.5 mm, or lengths in between these ranges. In several embodiments, implants configured for implantation into the punctum have a diameter between about 0.2 mm and 2.0 mm, including about 0.2 mm to about 0.3 mm, about 0.3 mm to about 0.4 mm, about 0.4 mm to about 0.5 mm, about 0.5 mm to about 0.6 mm about 0.5 mm to about 0.6 mm, about 0.6 mm to about 0.7 mm, about 0.7 mm to about 0.8 mm, about 0.8 mm to about 0.9 mm, about 0.9 mm to about 1.0 mm, about 1.0 mm to about 1.1 mm, about 1.1 mm to about 1.2 mm, about 1.2 mm to about 1.3 mm, about 1.3 mm to about 1.4 mm, about 1.4 mm to about 1.5 mm, about 1.5 mm to about 1.6 mm, about 1.6 mm to about 1.7 mm, about 1.7 mm to about 1.8 mm, about 1.8 mm to about 1.9 mm, about 1.9 mm to about 2.0 mm and diameters in between these ranges.

The characteristics of the implant shown in FIG. 1 are carried through FIGS. 1-7, however it shall be appreciated that any of the features of the implants disclosed herein can be used in combination with any other features disclosed herein (unless otherwise expressly noted). For example, all Figures are presently shown with a bulge 18 as a retention feature; the bulge may be replaced with any retention feature such as those disclosed herein. Furthermore, any type of drug arrangement may be used with any type of drug elution element. For example, the two phase drug of FIG. 5 may be included in a device having elution elements between the drug and the exterior such as in FIG. 2A or 2C. A region of a first therapeutic drug 20 is shown near the flange and a region of a second therapeutic drug 30 is shown in the lumen 12. One or both regions of drug may comprise pure drug, or drug plus excipients, or drug within a bioerodible or non-bioerodible matrix, as discussed in more detail below. Additionally, one or both regions may comprise packed powder formulation or pure drug, or tableted formulation or pure drug, or microspheres, nanospheres, liposomes, or the like of pure drug. Depending on the embodiment, the drug (or drugs) comprises drug-containing pellets, while in other embodiments, the drug is a liquid, a slurry, micro-pellets (e.g., micro-tablets) or powder. The drug (or drugs) may also be in the form of nanodispersions, depending on the embodiment. Combinations of any of these forms can also be used.

In several embodiments, one region can be of one form while the other region can be in another form (e.g., the drug of the first region is pure drug and the drug of the second region is drug plus excipient). Thus, any combinations of form, composition, etc. may be used in any of the drug regions, as is needed to tailor the drug elution to a desired profile.

The drug elution is controlled, depending on the embodiment, to allow drug release over a desired time frame. For example, in several embodiments, the duration drug release, depending on the embodiment, ranges from several months to several years, e.g., about 6 to about 12 months, about 12 to about 18 months, about 18 to about 24 months, about 24 to about 30 months, about 30 to about 36 months, etc.

Figure 8:
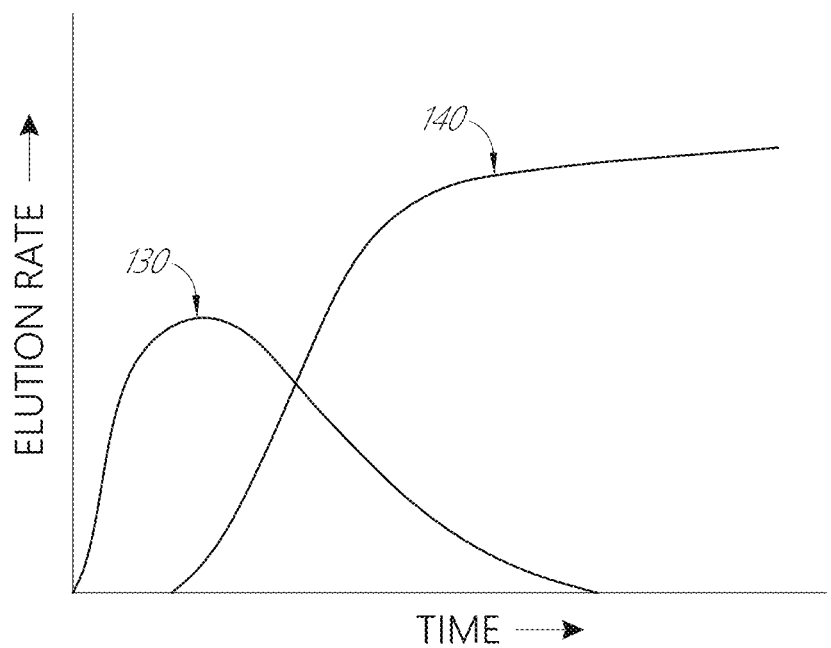
FIG. 8 is a schematic graph showing the elution profile of two therapeutic agents eluted from an implant according to an embodiment disclosed herein.

As a non-limiting example, in one embodiment, the first therapeutic drug 20 is steroid, such as loteprednol etabonate, dexamethasone, or triamcinolone acetonide (or a combination of any of these); and the second therapeutic drug 30 is cyclosporine. In some embodiments, because of the physical location and volume of the drugs, the first therapeutic drug (e.g., the steroid(s)) will tend to dissolve first, and thus, may be exhausted first (though in some embodiments the first drug is not exhausted at the time the release of the second drug is initiated). In several embodiments, the second drug (e.g., cyclosporine) will end to dissolve at or near the conclusion of the dissolution of the first drug, and thus, will have a more prolonged time course. In several embodiments, this "tail-to-nose" overlapping elution (or in some embodiments, serial elution) results in an advantageously therapeutic elution profile that provides a therapeutic level of the first and second drugs, but reduces the peaks and valleys in drug concentration that can be result from current therapies (such as eye drops). FIG. 8 shows a sample non-limiting schematic of a time course of drug elution that may result from implants configured similar to the embodiment shown in FIG. 1. Element 130 is the time course of the first drug, and element 140 is the time course of the second drug. While FIG. 1 depicts one lumen that is exposed to the ocular environment through which drug(s) is released, it shall also be understood that, depending on the embodiment, one, two, or more drug regions may be utilized in a punctal plug delivery device as disclosed herein.

The in vivo environment into which several embodiments of the implants disclosed herein are positioned may be comprised of a water-based solution (such as aqueous humor or tear film) or gel (such as vitreous humor). Water from the surrounding in vivo environment may, in some embodiments, diffuse into one or more of the interior lumens, depending on the embodiment, and begin dissolving a small amount of the tablet or drug-excipient powder. The dissolution process continues until a solution is formed within the lumen that is in osmotic equilibrium with the in vivo environment.

In additional embodiments, osmotic agents such as saccharides or salts are added to the drug to facilitate ingress of water and formation of the isosmotic solution. With relatively insoluble drugs, for example corticosteroids, the isosmotic solution may become saturated with respect to the drug in certain embodiments. In certain such embodiments, saturation can be maintained until the drug supply is almost exhausted. In several embodiments, maintaining a saturated condition is particularly advantageous because the elution rate will tend to be essentially constant, according to Fick's Law.

In some embodiments, the outer shell comprises one or more orifices to allow ocular fluid to contact the drug within the lumen (or lumens) of the implant and result in drug release. In some embodiments, as discussed in more detail below, a layer or layers of a permeable or semi-permeable material is used to cover the implant (wholly or partially) and the orifice(s) (wholly or partially), thereby allowing control of the rate of drug release from the implant. Additionally, in some embodiments, combinations of one or more orifices, a layer or layers covering the one or more orifices are used to tailor the rate of drug release from the implant.

Figure 2A:
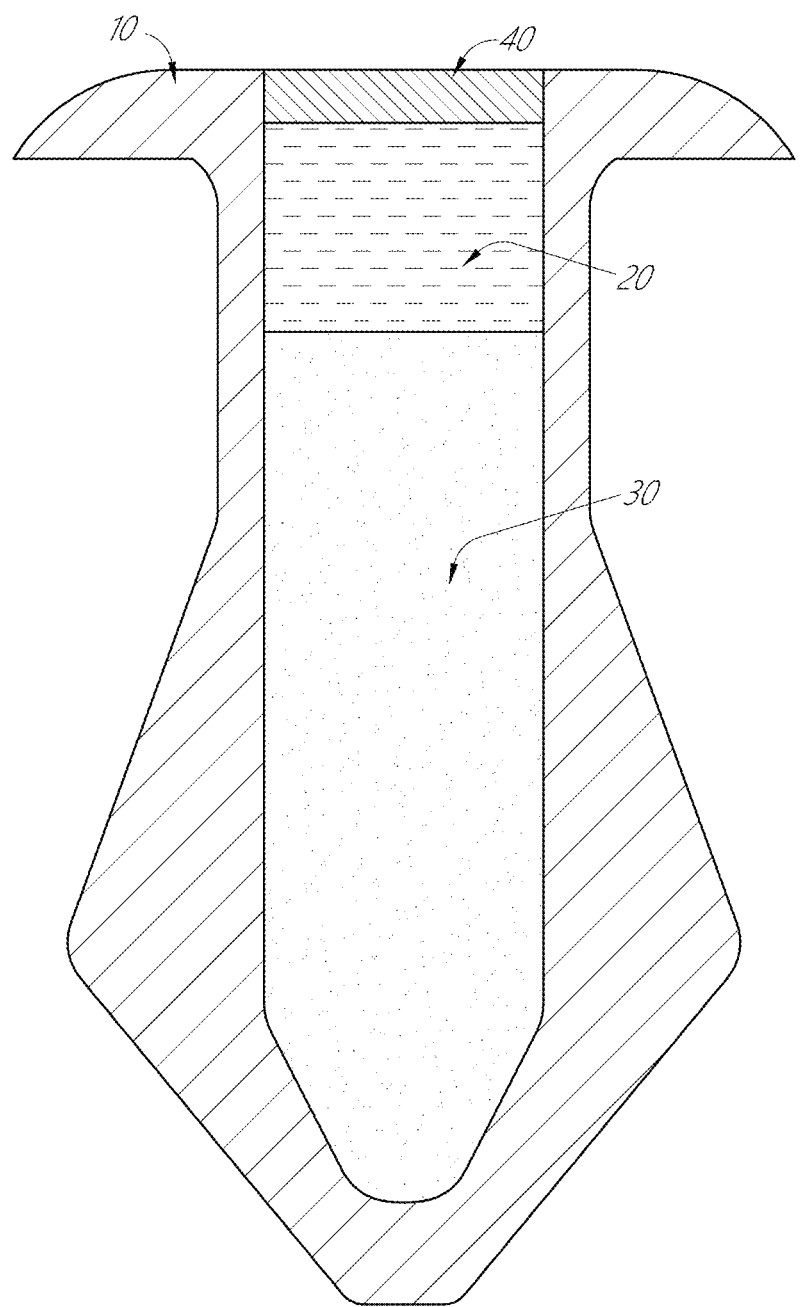
FIGS. 2A-2D illustrate schematic cross sections of additional embodiments of implants in accordance with embodiment disclosed herein.

FIG. 2A shows an embodiment wherein an additional component 40, representing a semi-permeable membrane or layer is included in the implant and obstructs (wholly or partially) the opening from the lumen of the implant to the ocular space external to the implant. Depending on the embodiment, component 40 may comprise a bioerodible or non-bioerodible hydrogel or a semi-permeable polymer, or a polymeric, metallic, or ceramic screen or filter. In any of such embodiments, the elution rate of the therapeutic drug (or drugs) within the implant is regulated according to the drug's permeability through component 40. As discussed in more detail below, the regulation of permeability can be altered by changing one or more characteristics of the component 40 (e.g., thickness, chemical makeup, porosity, etc.). It shall also be appreciated that elution regulation component 40 (or its equivalents) may be incorporated into any subsequent example, including those shown in any of the additional figure or any embodiment described herein.

Figure 2B:
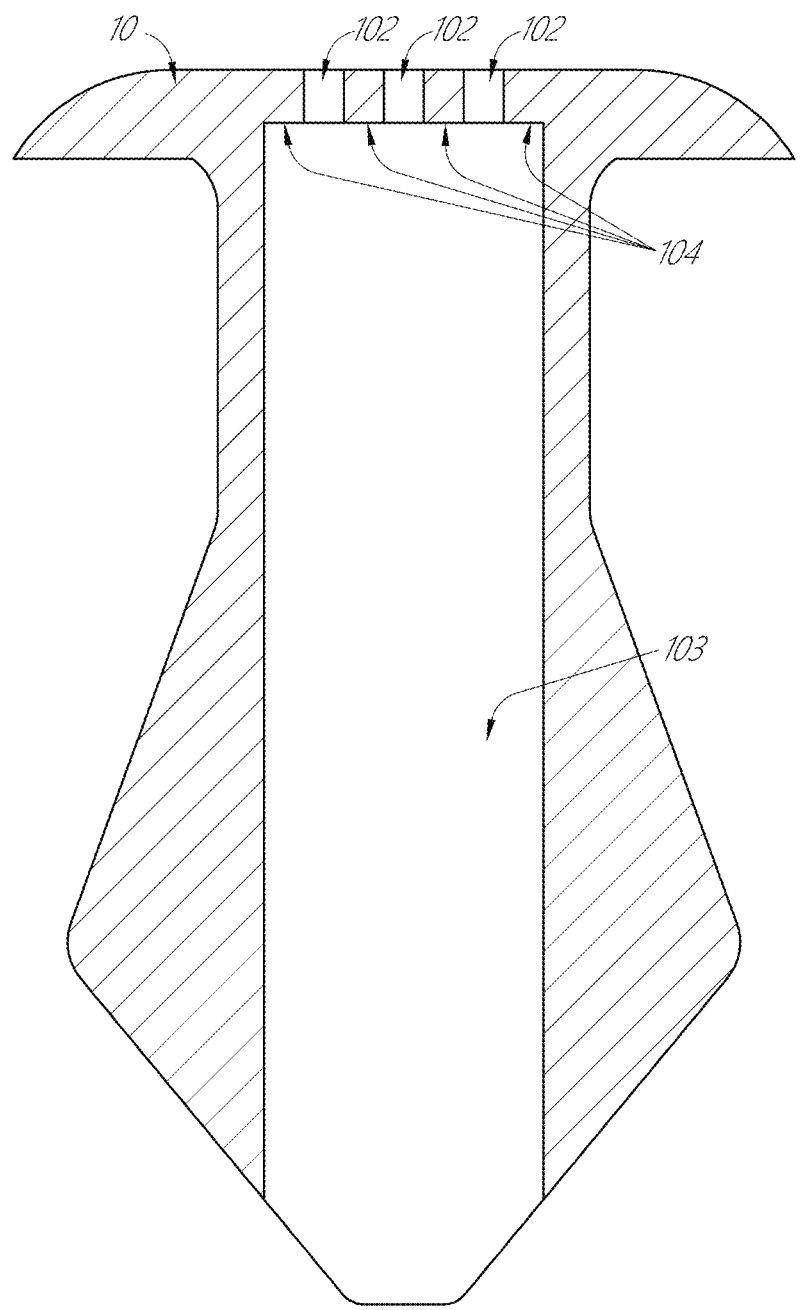

FIG. 2B depicts another embodiment of an implant that provides an advantageous drug elution profile. Item 10 is the body of the punctal plug, as discussed above, with a flange that rests in apposition to the surface of the eyelid after the plug is implanted into the punctum. In several embodiments, the punctal plug 10 is molded of a soft elastomeric material, such as silicone, polyurethane or a copolymer (such as PurSil®). In several embodiments, these materials (or combinations) allow the plug to conform to the punctum of a specific patient, thereby increasing the comfort of the implant over the life of implantation. In several embodiments, these materials (or combinations thereof) also facilitate the consistent manufacture of the implants. In several embodiments in which the punctual plug is molded of silicone, the size of the implant may optionally vary depending on the patient. In other words, sonic embodiments of silicone (or other similar material) implants are personalized to an individual patient or a segment of possible patients and their anatomical characteristics. In some embodiments in which the punctual plug is comprised of hydrogel, the implants are designed as a "one size fits all patients" implant. In alternative embodiments, however other materials disclosed herein may be used to construct the implant (either in whole or in part). In certain embodiments, the outer shell is not biodegradable, while in others, the shell is optionally biodegradable.

In some embodiments, the implant is made of a flexible material. In other embodiments, a portion of the implant is made from flexible material (e.g., the body) while another portion of the implant is made from rigid or semi-rigid material (e.g., the body or the bulge). In some embodiments, the implant comprises one or more flexures (e.g., hinges). In some embodiments, the drug delivery implant is pre-flexed, yet flexible enough to be contained within the straight lumen of a delivery device.

In other embodiments, at least a portion of the implant (e.g., an internal spine or an anchor) is made of a material capable of shape memory. A material capable of shape memory may be compressed and, upon release, may expand axially or radially, or both axially and radially, to assume a particular shape. In some embodiments, at least a portion of the implant has a preformed shape. In other embodiments, at least a portion of the implant is made of a superelastic material. In some embodiments, at least a portion of the implant is made up of nitinol. In other embodiments, at least a portion of the implant is made of a deformable material.

Figure 2C:
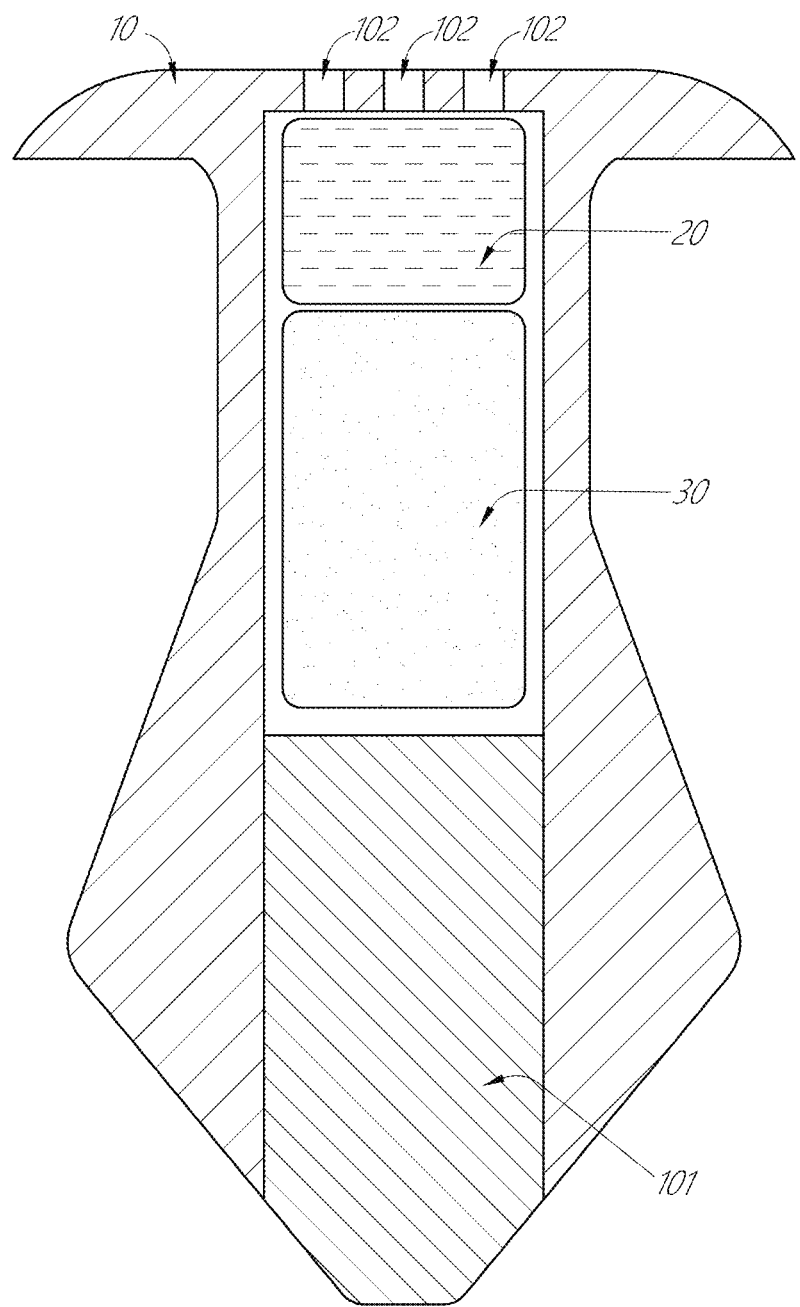

As shown in FIG. 2B, several embodiments of the punctal plug comprise a lumen 103 that is molded with an opening at the bottom of the plug. At the top of the plug is a thin-walled region (or plurality of regions) 104, extending across the upper end of lumen 103. In several embodiments, the thin-walled regions 104 function to retain solid or dissolved drug housed within plug 10 as shown in FIG. 2C (e.g., they function as a large scale sieve), while also providing a diffusion path between the drug and the tear film external to plug 10. Depending on the embodiment, region 104 comprises the same material as the rest of plug 10, or alternatively, comprises a different material (for example, manufactured as an insert molded with the rest of the plug). Region 104 allows diffusion of drug into the tear film according to the drug permeability of the region 104 material, the cross-sectional dimension of region 104, and the optional addition of holes or fenestrations 102. Control of drug elution rates is discussed in more detail below. Depending on the embodiment, region 104 ranges in thickness between about 0.0005 inches to about 0.05 inches. For example, region 104 ranges in thickness from about 0.0005 inches to about 0.00075 inches, about 0.00075 inches to about 0.001 inches, about 0.001 inches to about 0.00125 inches, about 0.00125 inches to about 0.0015 inches, about 0.0015 inches to about 0.00175 inches, about 0.00175 inches to about 0.002 inches, about 0,002 inches to about 0.00225 inches, about 0.00225 inches to about 0.0025 inches, about 0.0025 inches to about 0.00275 inches, about 0.00275 inches to about 0.003 inches, about 0.003 inches to about 0.00325 inches, about 0.00325 inches to about 0.0035 inches, about 0.0035 inches to about 0.00375 inches, about 0.00375 inches to about 0.004 inches, about 0.004 inches to about 0.0045 inches, about 0.0045 inches to about 0.005 inches, about 0.005 inches to about 0.006 inches, about 0.006 inches to about 0.006 inches, about 0.006 inches to about 0.007 inches, about 0.007 inches to about 0.008 inches, about 0.008 inches to about 0.009 inches, about 0.009 inches to about 0.01 inches and any thickness between those listed.

In those embodiments comprising holes or fenestrations 102, the holes or fenestrations may be of any shape, including but not limited to square, round, irregular-shaped. In each case, an individual fenestration or hole has a diameter less than that of lumen 103. Depending on the embodiment, the holes or fenestrations are located in any geometrical pattern (or randomly positioned) within region 104. In those embodiments having more than one region 104, the holes or fenestrations may be positioned differentially between each region (e.g., patterned positioning in a first region and random positioning in a second region). Holes or fenestrations 102 may be formed during molding of plug 10, or may be laser machined after molding, such as by ablation, stretching, etching, grinding, molding, femtosecond laser exposure, particle blasting, machining, or other methods.

In certain embodiments comprising holes or fenestrations 102, the implant allows for drug elution proximally toward the tear film, as well as distally toward the nasolacrimal duct. In these embodiments, the active agent is released into the tear film, the nasolacrimal duct, or both the tear film and the nasolacrimal duct. Distal drug elution is useful, in several embodiments, for intranasal and/or systemic drug delivery. Embodiments comprising holes or fenestrations 102 also optionally comprise at least one non-occlusive retention feature, as discussed above, rendering the implant non-occlusive and comprising a design solution for overall distal drug delivery, in these non-occlusive embodiments, for example, a therapeutic agent eluted from either a proximal end or distal end of the implant will ultimately drain distally toward the nasolacrimal duct. In contrast, in occlusive embodiments, for example, agents eluted from a proximal end of the implant results in only proximal drug delivery as delivery of the therapeutic agent is inhibited distally of the proximal end.

In one embodiment, the implant shown in FIG. 2C, is assembled key first obtaining tablets or powder (or other form) of at least a first and second drug. In reverse order of release from the implant, the drugs are loaded through the open end of lumen 103 shown in FIG. 2B. FIG. 2C shows the assembled delivery device, where item 20 is a region of a first therapeutic drug, and item 30 is a region of a second therapeutic drug. As discussed above, one or both regions may comprise pure drug, or drug plus excipients, or drug within a bioerodible or non-bioerodible matrix. One or both regions may comprise packed powder formulation or pure drug, or tabletted formulation or pure drug, or microspheres, nanospheres, liposomes, or the like of pure drug. Upon completion of drug loading into the lumen, the open end of lumen 103 is sealed with a plug 101. Depending on the embodiments, the plug comprises a flowable material that acts as a sealant by filling the remaining space in the lumen 103. For example, in one embodiment, the plug 101 comprises, RTV silicone injected into the open end of lumen 103. In other embodiments, the plug 101 is preformed of silicone elastomer, another polymer (or polymers), or another biocompatible material, and press fit into lumen 103. In still additional embodiments, plug 101 comprises a thermoplastic material such as PurSil®, which is then thermoformed in place to seal the end of the implant.

Figure 2D:
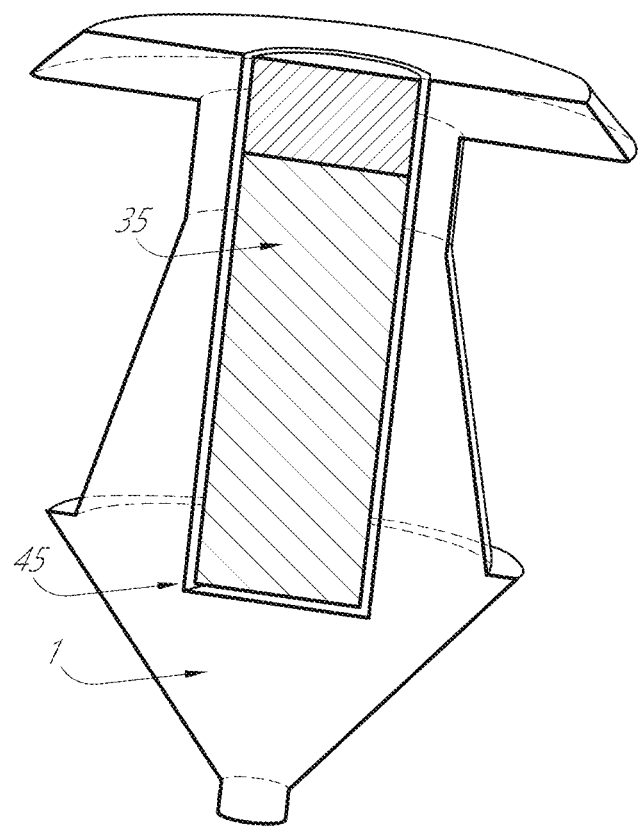

In several embodiments, as shown in FIG. 2D, the drug load is isolated from the plug material with a drug sleeve (e.g., a sleeve body). FIG. 2D shows a cross-sectional view of an implant 1 comprising a drug core 35 and surrounding drug sleeve 45, according to several embodiments. In several such embodiments, the sleeve body comprises appropriate shapes, dimensions, and/or materials to regulate, adjust, or otherwise control elution of the therapeutic agent from the drug core. In several embodiments, the drug sleeve comprises a material that is substantially impermeable (e.g., less than 50% permeable) to the therapeutic agent so that the rate of migration of the therapeutic agent is primarily (or at least in part) controlled by the exposed surface area of the drug core that is not covered by the drug sleeve. Illustrative and non-limiting examples of suitable materials for the drug sleeve include, but are not limited to, polypropylene, polyimide, glass, nitinol, polyvinyl alcohol, polyvinyl pyrolidone, collagen, chemically-treated collagen, polyethersulfone (PES), poly(styrene-isobutyl-styrene), polyurethane, ethyl vinyl acetate (EVA), polyetherether ketone (PEEK), Kynar (Polyvinylidene Fluoride; PVDF), Polytetrafluoromethylene (PTFE), Polymethylmethacrylate (PMMA), Pebax, acrylic, polyolefin, polydimethylsiloxane and other silicone elastomers, polypropylene, hydroxyapetite, titanium, gold, silver, platinum, other metals and alloys, ceramics, plastics and mixtures or combinations thereof.

In several such embodiments, the drug sleeve allows for an exchangeable drug core if the therapeutic agent needs to be replenished, replaced, or supplemented by the same or different agent. Accordingly, the implant body can remain implanted in the patient. In some embodiments, the drug sleeve remains in the implant while only the drug core is replaced. In these embodiments, the drug sleeve may be provided, for example, with external protrusions that apply force, to the drug sleeve when squeezed and eject the core from the drug sleeve. In some embodiments, the drug sleeve is removed with the drug core.

In many embodiments, the drug sleeve ranges between about 0.5 and 2.4 mm long (e.g., from the proximal end to the distal end). The length of the drug sleeve, in sonic embodiments, ranges from about 0.5 mm to about 0.7 mm, about 0.7 mm to about 0.9 mm, about 0.9 mm to about 1.0 mm, about 1.0 mm to about 1.1 mm, about 1.1 mm to about 1.2 mm, about 1.2 mm to about 1.3 mm, about 1.3 mm to about 1.35 mm, about 1.35 mm to about 1.4 mm, about 1.4 mm to about 1.45 mm, about 1.45 mm to about 1.5 mm, about 1.5 mm to about 1.55 mm, about 1.55 mm to about 1.6 mm, about 1.6 mm to about 1.65 mm, about 1.65 mm to about 1.7 mm, about 1.7 mm to about 1.9 mm, about 1.9 mm to about 2.1 mm, about 2.1 mm to about 2.3 mm, about 2.3 mm to about 2.5 mm, or lengths in between these ranges. In several embodiments, drug sleeves have an inner diameter between about 0.2 mm and 1.9 mm, including about 0.2 mm to about 0.3 mm, about 0.3 mm to about 0.4 mm, about 0.4 mm to about 0.5 mm, about 0.5 mm to about 0.6 mm, about 0.5 mm to about 0.6 mm, about 0.6 mm to about 0.7 mm, about 0.7 mm to about 0.8 mm, about 0.8 mm to about 0.9 mm, about 0.9 mm to about 1.0 mm, about 1.0 mm to about 1.1 mm, about 1.1 mm to about 1.2 mm, about 1.2 mm to about 1.3 mm, about 1.3 mm to about 1.4 mm, about 1.4 mm to about 1.5 mm, about 1.5 mm to about 1.6 mm, about 1.6 mm to about 1.7 mm, about 1.7 mm to about 1.8 mm, about 1.8 mm to about 1.9 mm and any diameters in between or overlapping with these ranges.

Figure 3:
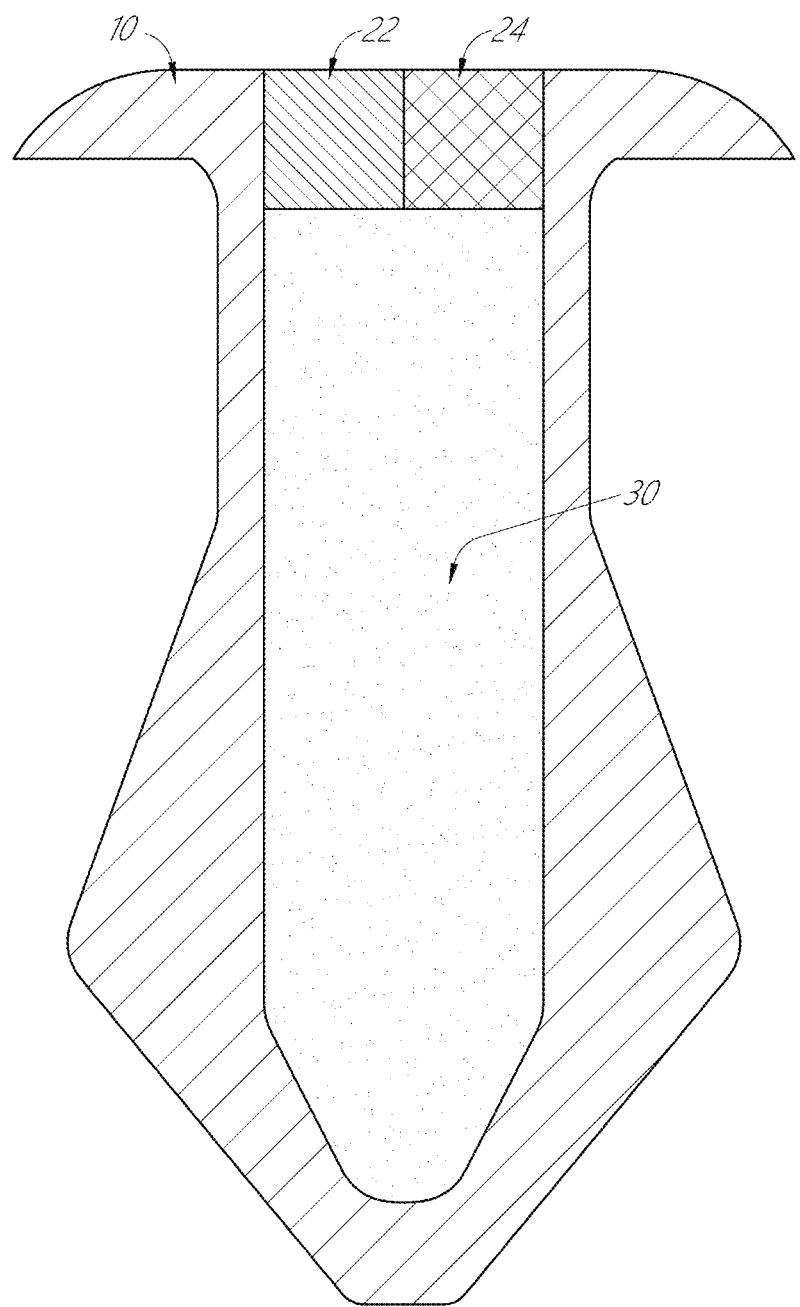
FIG. 3 illustrates a schematic cross section of an additional embodiment of an implant in accordance with disclosure herein.

FIG. 3 shows an embodiment where two drug regions, depicted as 22 and 24, respectively are loaded in parallel within the punctual plug. In such embodiments, both drug regions 22 and 24 begin eluting at the same time. In some embodiments, the elution profiles of 22 and 24 are substantially similar, for example when drug 24 reduces the potential for side effects of administration of drug 22. In additional embodiments, the elution profiles of drug 22 and drug 24 are offset. In some embodiments, drug 22 and 24 are completely or substantially eluted at such time as a third drug region 30 begins elution. While shown effectively as equal proportions, it shall be appreciated that drug 22 and drug 24 can be placed in the punctal plug in any ratio with respect to one another that produces a desired therapeutic effect. For example, drug 22 may make up about 10%, about 20%, about 25%, about 30% or more of the total amount of drugs 22 and 24 present in the implant. Alternatively, drug 22 may make up about 60%, about 70%, about 80%, about 90% or more of the total amount of drugs 22 and 24 present in the implant. Any combination of drug 22 and 24 can be used, depending on the embodiment. Moreover, while shown in FIG. 3 as parallel to one another, different physical configurations of drug 22 and 24 are used in other embodiments. For example, the drugs may be loaded at an angle with respect to one another, in order to control the surface area of the drug that is exposed to tear file at a given time post implantation. For example, an angular gradient could be used to start with a high percentage of release of drug 22 as compared to release of drug 24, with an inverse elution profile being generated as the drugs are eluted (e.g., as elution of the drugs proceeds, the proportion of drug 22 being released, versus the total, decreases, while the proportion of drug 24 increases.

Figure 4:
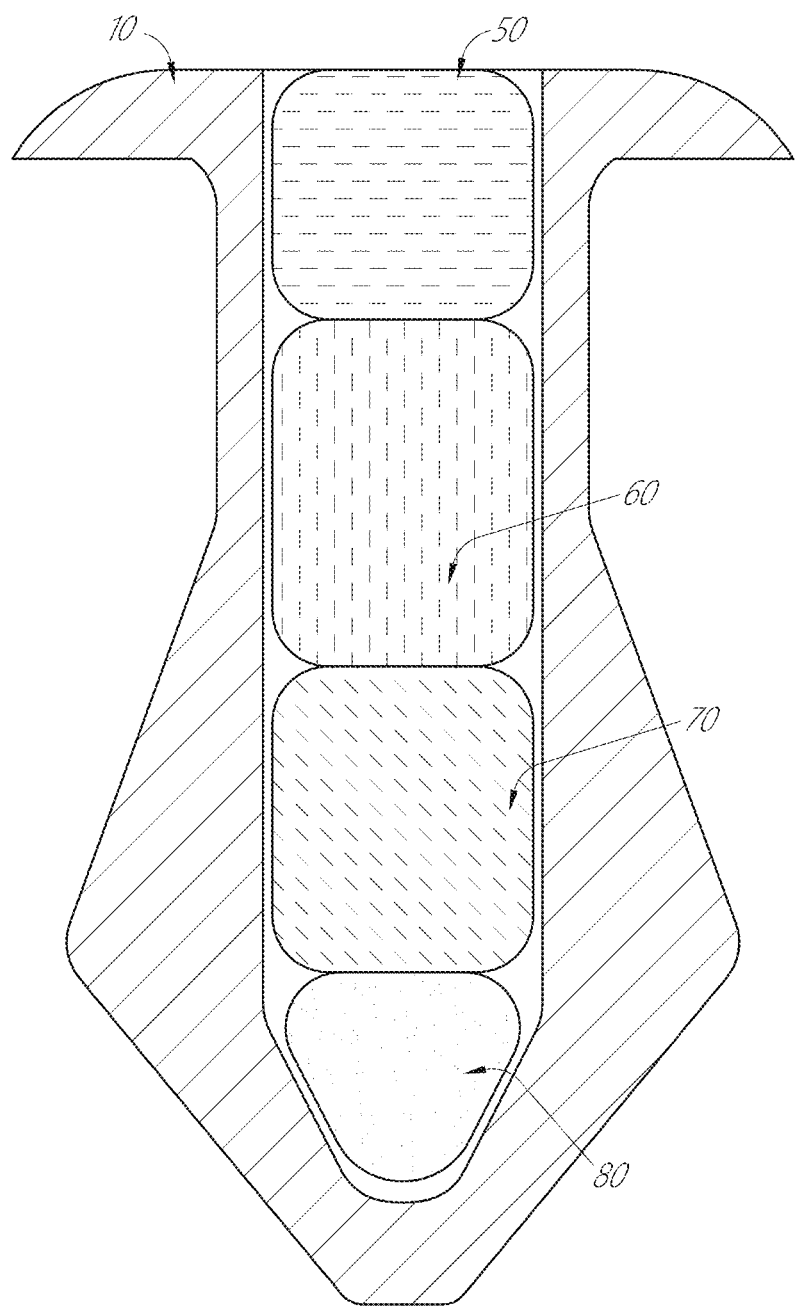
FIG. 4 illustrates a schematic cross section of an additional embodiment of an implant in accordance with disclosure herein.

FIG. 4 shows an embodiment in which multiple drug regions 50, 60, 70, and 80 are preformed into tablets (or micropellets) to facilitate control of drug formulation, and to facilitate manufacturing assembly of the punctal plug delivery device. For example, the preformation of the drugs into tablets (or pellets, or some other solid or semi-solid form) advantageously enables the placement of the drugs sequentially into the implant with reduced complications during assembly (e.g., mis-ordering of the drugs, damage to the implant, etc.). Also, in several embodiments, pre-formation allows the specific tailoring of a drug profile for a particular patient. For example, if a patient had previously had an implant with drug regions 50, 60, 70, and 80, and experienced adverse effects, an option may be to reformulate the drugs within the implant (e.g., drug regions 50, 80, 60, and 70, or 50, 50, 60, 70). This advantageously allows customization of a drug treatment regime for the therapeutic needs of a specific patient. Alternative methods for loading an implant as disclosed herein are provided in U.S. Pat. No. 7,117,870, the entire contents of which are incorporated by reference herein.

Figure 5:
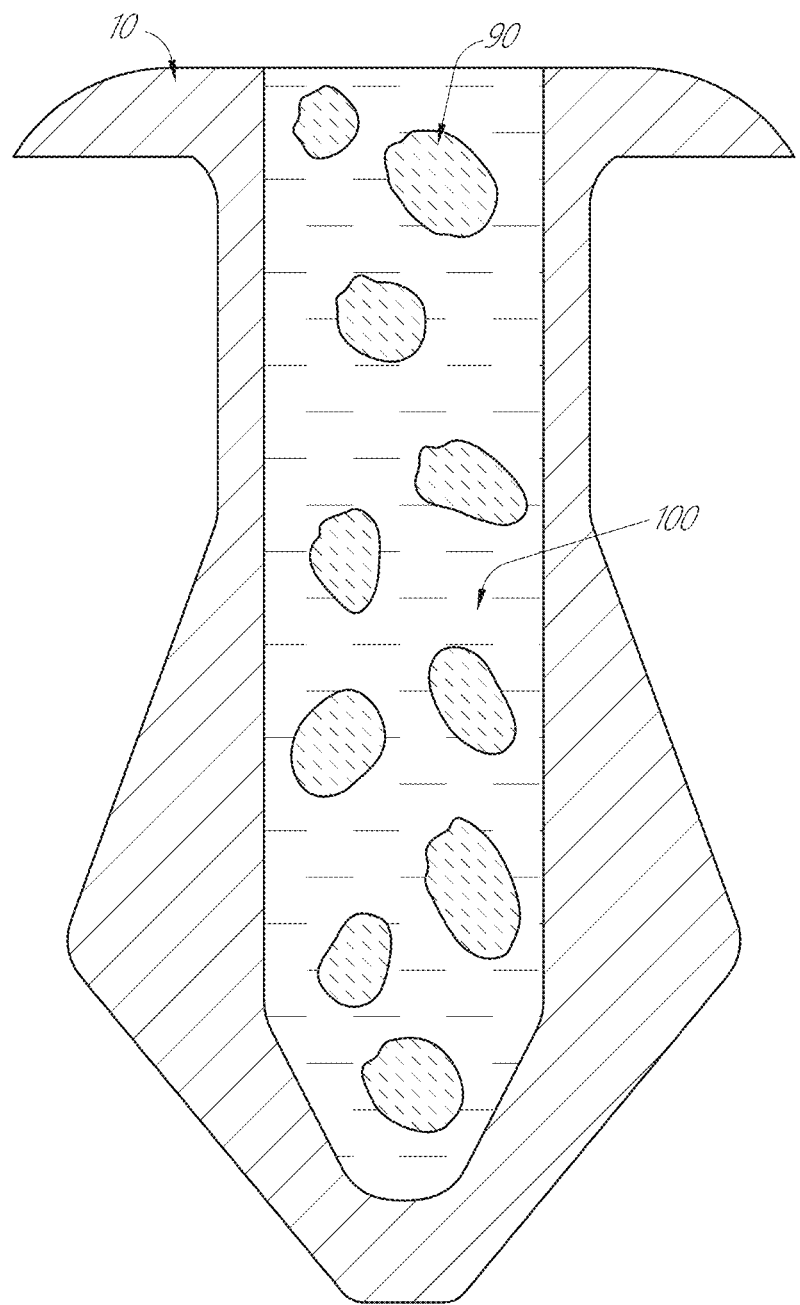
FIG. 5 illustrates a schematic cross section of an additional embodiment of an implant in accordance with disclosure herein.

FIG. 5 shows an arrangement used in several embodiments, wherein drug region 90 comprises a discontinuous first phase which is distributed within drug region 100, which forms a second phase. For example, drug region 90 may comprise microparticles, nanoparticles, liposomes, or the like, any or all of which may carry a first therapeutic drug. Drug region 100, depending on the embodiment, comprises a dispersion of solid or liquid particles or droplets of a second therapeutic drug dispersed within a hydrogel matrix, or some other semi-permeable polymer matrix. Such embodiments, are advantageous in that small and predictable boluses of drug 90 can be intermixed with a second (or more) drug in different phases. This allows a further degree of tailoring the release profiles of the drug or drugs. Moreover, in several embodiments, the second region of drug 100 can complement the first region 90, for example in providing an environment that improves the stability of drug 90, which may otherwise be relatively volatile.

Figure 6:
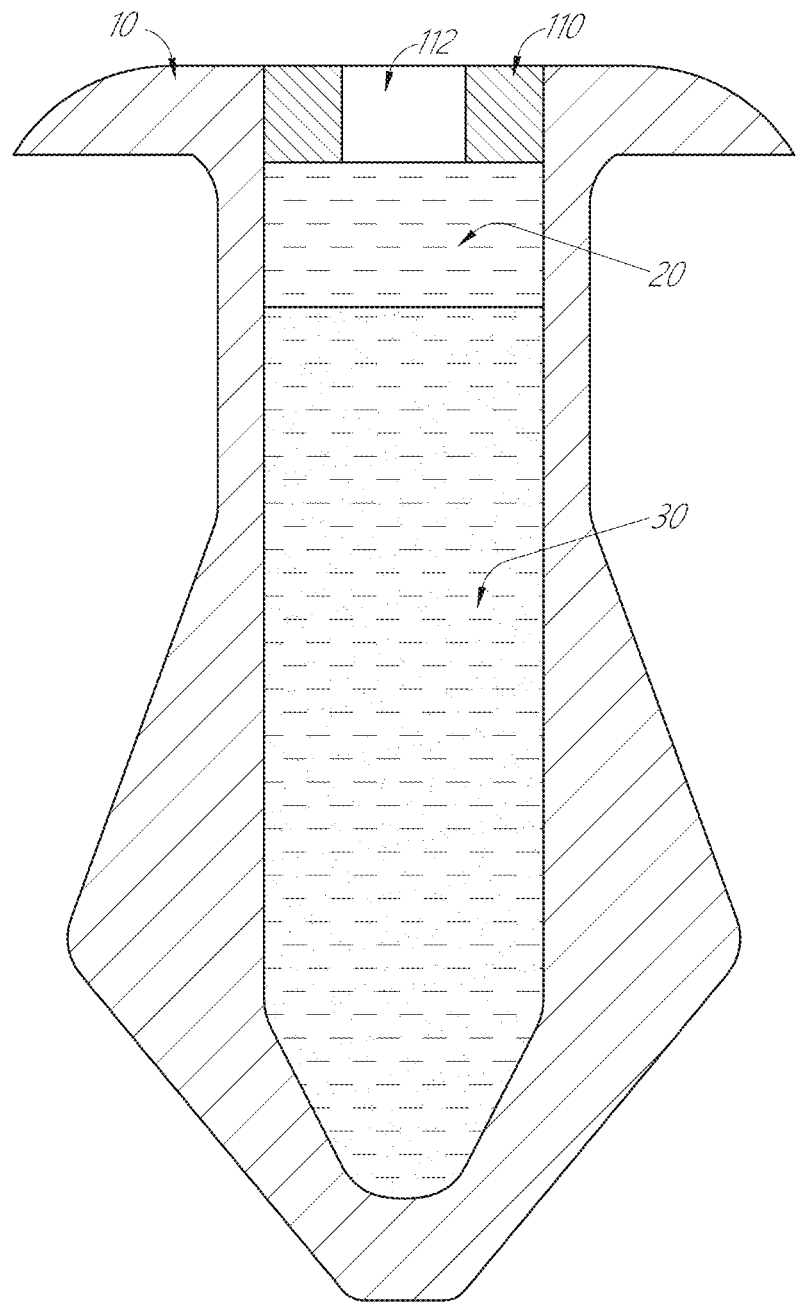
FIG. 6 illustrates a schematic cross section of an additional embodiment of an implant in accordance with disclosure herein.

FIG. 6 shows an additional embodiment of a punctal plug comprising a ring-shaped component 110 comprising an aperture 112, the aperture being sized in diameter and thickness to regulate elution rate according to Fick's Law of diffusion (discussed in more detail below). Such embodiments are advantageous at least in that the ring-shaped component can be used to further refine and tailor the release of a drug (or drugs) from the implant, while having the implant be "off the shelf". For example, the implant shell can be one of several stock sizes (e.g., small, medium, large, etc.), each size having a particular size lumen. The ring-shaped component 110 can thus be used to adjust the rate of elution of the drug (or drugs) from the implant by re-sizing the opening of the lumen according to the needs of a particular patient. The ring-shaped component 110, in several embodiments, is made of a material that is generally impermeable to the drug (or drugs) in the lumen. Control of drug release is then calculated by the dimensions of aperture 112, and any membrane or other controlling material (e.g., component 40 of FIG. 2) placed within, or over, the aperture. Alternatively, or in combination, the ring-shaped component 110 can comprise a material that is semi-permeable material to one or more of the drugs within the lumen of the implant. In such embodiments, the combination of the ring-shaped component 110, its dimensions, and its interaction with the aperture and/or component 40 work in concert to define the release rates of the drugs from the implant.

Figure 9:
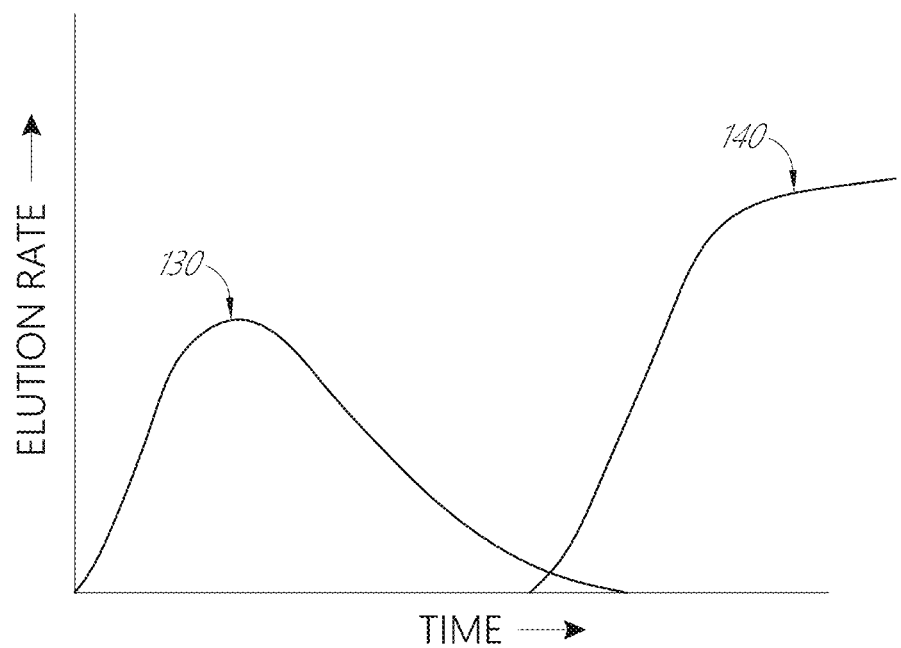
FIG. 9 is a schematic graph showing an alternative elution profile of two therapeutic agents eluted from an additional implant according to an embodiment disclosed herein.

As discussed above, the various implant embodiments result in characteristic elution profiles. Such elution profiles are shown in FIGS. 8 and 9. These profiles can advantageously be modified to meet the needs of a particular patient, not only in terms of the drugs that are administered and at what time, but in what amount compared with one another, so as to reduce (or treat) side effects.

Figure 7:
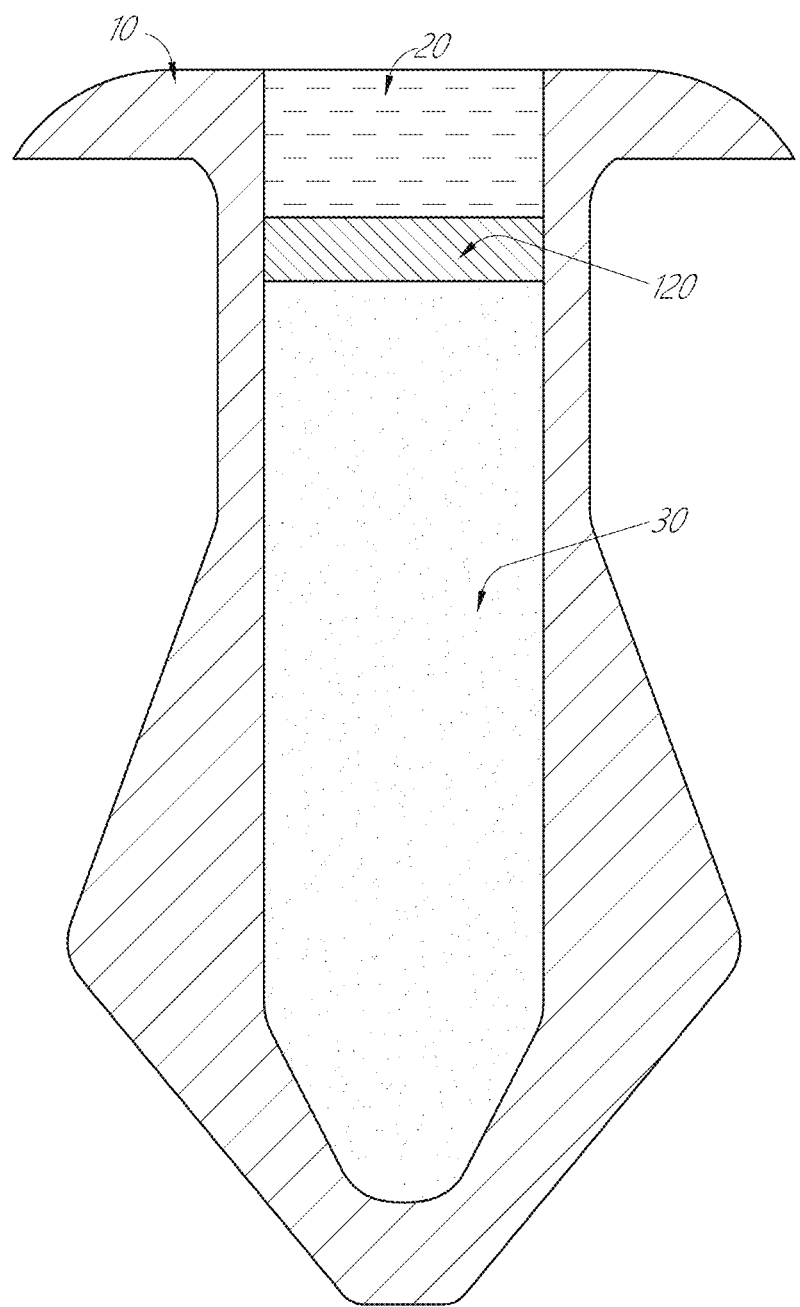
FIG. 7 illustrates a schematic cross section of an additional embodiment of an implant in accordance with disclosure herein.

FIG. 7 shows an additional component 120, which is a separator placed between the first drug region 20 and the second drug region 30. Separator 120, depending on the embodiment, comprises a bioerodible, non-bioerodible; hydrogel; semi-permeable polymer; or a porous element comprising ceramic or metal. Separator 120 serves to create a separation in time between the elution of the drug in region 20 and the drug in region 30. FIG. 9 depicts a schematic elution profile resulting from an embodiment such as the implant of FIG. 7, In FIG. 9, 130 is the time course of drug elution from the first region 20, and 140 is the time course of elution from the second drug region 30. In some cases, the two drug regions may contain the same drug, and the purpose of separator 120 is to create a "drug holiday", a time interval during which little or no drug is being eluted (compare the elution profile of FIG. 8 with that of FIG. 9).

Thus, the implants according to the embodiments disclosed herein allow a highly flexible approach for drug delivery to the eye as well as the ability to customize the drugs used, release timing and concentration (vis-à-vis other drugs in the implant) and thereby create a personalized overall therapeutic regime. Because in certain embodiments, the drug delivery implant may contain one or more drugs which may or may not be compounded with a bioerodible polymer or a bioerodible polymer and at least one additional agent, the release profiles of each can be managed independently, further adding to the flexibility of the overall treatment plant. In still other embodiments, the drug delivery implant is used to sequentially deliver multiple drugs. Some embodiments elute one or more drugs at a constant rate, with other embodiments release one or more drugs with a zero-order release profile. Yet other embodiments yield variable elution profiles. Still other embodiments are designed to stop elution completely or nearly completely for a predetermined period of time (e.g., a "drug holiday") and later resume elution at the same or a different elution rate or elution concentration. Some such embodiments elute the same therapeutic agent before and after the drug holiday while other embodiments elute different therapeutic agents before and after the drug holiday.

Figure 10:
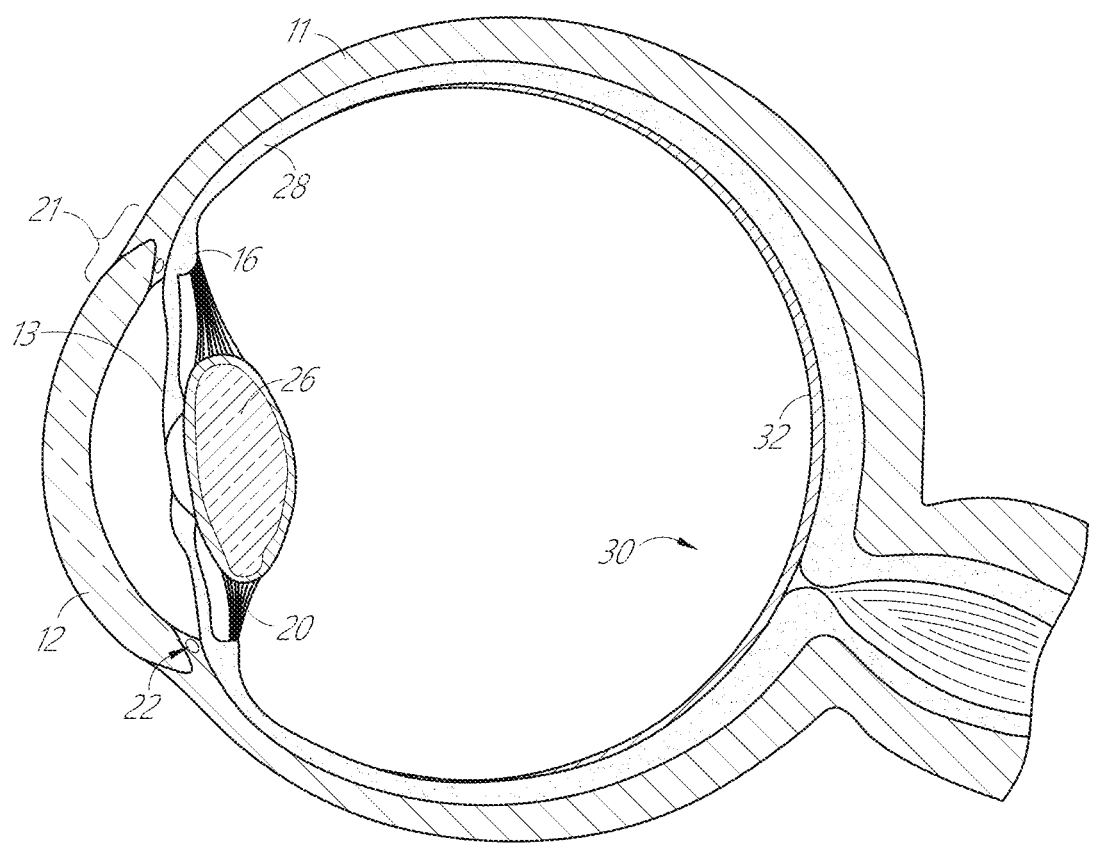
FIG. 10 illustrates the anatomy of an eye.

FIG. 10 illustrates the anatomy of an eye, which includes the sclera 11, which joins the cornea 12 at the limbus 21, the iris 13 and the anterior chamber 20 between the iris 13 and the cornea 12. The eye also includes the lens 26 disposed behind the iris 13, the ciliary body 16 and Schlemm's canal 22. The eye also includes a uveoscleral outflow pathway, which functions to remove a portion of fluid from the anterior chamber, and a suprachoroidal space positioned between the choroid 28 and the sclera 11. The eye also includes the posterior region 30 of the eye which includes the macula 32.

Controlled Drug Release

The drug delivery implants as described herein, function to house a drug and provide drug elution from the implant in a controlled fashion, based on the design of the various components of the implant, for an extended period of time. Various elements of the implant composition, implant physical characteristics, and the composition of the drug work in combination to produce the desired drug release profile.

As described above the drug delivery implant may be made from any biological inert and biocompatible materials having desired characteristics. Desirable characteristics, in some embodiments, include permeability to liquid water or water vapor, allowing for an implant to be manufactured, loaded with drug, and sterilized in a dry state, with subsequent rehydration of the drug upon implantation. Also desirable for certain portions of the implant, depending on the embodiment, is use of a material comprising microscopic porosities between polymer chains. These porosities may interconnect, which forms channels of water through the implant material. In several embodiments, the resultant channels are convoluted and thereby form a tortuous path which solublized drug travels during the elution process. Implant materials advantageously also possess sufficient permeability to a drug such that the implant may be a practical size for implantation. Thus, in several embodiments, portions of the implant (e.g., the membrane material) are sufficiently permeable to the drug to be delivered that the implant is dimensioned to reside wholly contained within the eye of a subject. Implant material also ideally possesses sufficient elasticity, flexibility and potential elongation to not only conform to the target anatomy during and after implantation, but also remain unkinked, untorn, unpunctured, and with a patent lumen during and after implantation. In several embodiments, implant material would advantageously processable in a practical manner, such as, for example, by molding, extrusion, thermoforming, and the like. In particular, in some embodiments, implants are manufactured via injection molding.

Illustrative, examples of suitable materials for the outer shell include, but are not limited to, polypropylene, polyimide, glass, nitinol, polyvinyl alcohol, polyvinyl pyrolidone, collagen, chemically-treated collagen, polyethersulfone (PES), poly(styrene-isobutyl-styrene), polyurethane, ethyl vinyl acetate (EVA), polyetherether ketone (PEEK), Kynar (Polyvinylidene Fluoride; PVDF), Polytetrafluoroethylene (PTFE), Polymethylmethacrylate (PMMA), Pebax, acrylic, polyolefin, polydimethylsiloxane and other silicone elastomers, polypropylene, hydroxyapetite, titanium, gold, silver, platinum, other metals and alloys, ceramics, plastics and mixtures or combinations thereof. Additional suitable materials used to construct certain embodiments of the implant include, but are not limited to, poly(lactic acid), poly(tyrosine carbonate), polyethylene-vinyl acetate, poly(L-lactic acid), poly(D,L-lactic-co-glycolic acid), poly(D,L-lactide), poly(D,L-lactide-co-trimethylene carbonate), collagen, heparinized collagen, poly (caprolactone), poly(glycolic acid), and/or other polymer, copolymers, or block co-polymers, polyester urethanes, polyester amides, polyester ureas, polythioesters, thermoplastic polyurethanes, silicone-modified polyether urethanes, polycarbonate urethane), or polyimide. Thermoplastic polyurethanes are polymers or copolymers which may comprise aliphatic polyurethanes, aromatic polyurethanes, polyurethane hydrogel-forming materials, hydrophilic polyurethanes (such as those described in U.S. Pat. No. 5,428,123, which is incorporated in its entirety by reference herein), or combinations thereof. Non-limiting examples include elasthane (poly(ether urethane)) such as Elasthane™ 80A, Lubrizol, Tecophilic™, Pellethane™, carbothane™, Tecothane™, Tecoplast™, and Estane™. In some embodiments, polysiloxane-containing polyurethane elastomers are used, which include Carbosil™ 20 or Pursil™ 20 80A, Elast-Eon™, and the like. Hydrophilic and/or hydrophobic materials may be used. Non-limiting examples of such elastomers are provided in U.S. Pat. No. 6,627,724, which is incorporated in its entirety by reference herein. Poly(carbonate urethane) may include Bionate™ 80A or similar polymers. In several embodiments, such silicone modified polyether urethanes are particularly advantageous based on improved biostability of the polymer imparted by the inclusion of silicone. In addition, in some embodiments, oxidative stability and thrombo-resistance is also improved as compared to non-modified polyurethanes. In some embodiments, there is a reduction in angiogenesis, cellular adhesion, inflammation, and/or protein adsorption with silicone-modified polyether urethanes. In other embodiments, should angiogenesis, cellular adhesion or protein adsorption (e.g., for assistance in anchoring an implant) is preferable, the degree of silicone (or other modifier) may be adjusted accordingly. Moreover, in some embodiments, silicone modification reduces the coefficient of friction of the polymer, which reduces trauma during implantation of devices described herein. In sonic embodiments, silicone modification, in addition to the other mechanisms described herein, is another variable that can be used to tailor the permeability of the polymer. Further, in some embodiments, silicone modification of a polymer is accomplished through the addition of silicone-containing surface modifying endgroups to the base polymer. In other embodiments, flurorocarbon or polyethylene oxide surface modifying endgroups are added to a based polymer. In several embodiments, one or more biodegradable materials are used to construct all or a portion of the implant, or any other device disclosed herein. Such materials include any suitable material that degrades or erodes over time when placed in the human or animal body, whether due to a particular chemical reaction or enzymatic process or in the absence of such a reaction or process. Accordingly, as the term is used herein, biodegradable material includes bioerodible materials. Such materials can optionally biodegrade or bioerode at a predictable rate so that the plugs expire after the treatment time is over or are easily flushed out for replacement. In such biodegradable embodiments, the degradation rate of the biodegradable outer shell is another variable (of many) that may be used to tailor the drug elution rate from an implant.

In some embodiments, such as where the drug is sensitive to moisture (e.g. liquid water, water vapor, humidity) or where the drug's long term stability may be adversely affected by exposure to moisture, it may be desirable to utilize a material for the implant or at least a portion of the implant, which is water resistant, water impermeable or waterproof such that it presents a significant barrier to the intrusion of liquid water and/or water vapor, especially at or around human body temperature (e.g. about 35-40° C. or 37° C.). This may be accomplished by using a material that is, itself, water resistant, water impermeable or waterproof.

In some circumstances, however, even materials that are generally considered water impermeable may still allow in enough water to adversely affect the drug within an implant. For example, it may be desirable to have 5% by weight of the drug or less water intrusion over the course of a year. In one embodiment of implant, this would equate to a water vapor transmission rate for a material of about $1\times10^{-3}$ g/m²/day or less. This may be as much as one-tenth of the water transmission rate of some polymers generally considered to be water resistant or water impermeable. Therefore, it may be desirable to increase the water resistance or water impermeability of a material.

The water resistance or water impermeability of a material may be increased by any suitable method. Such methods of treatment include providing a coating for a material (including by lamination) or by compounding a material with a component that adds water resistance or increases impermeability. For example, such treatment may be performed on the implant (or portion of the implant) itself, it may be done on the material prior to fabrication (e.g. coating a polymeric tube), or it may be done in the formation of the material itself (e.g. by compounding a resin with a material prior to forming the resin into a tube or sheet). Such treatment may include, without limitation, one or more of the following: coating or laminating the material with a hydrophobic polymer or other material to increase water resistance or impermeability; compounding the material with hydrophobic or other material to increase water resistance or impermeability; compounding or treating the material with a substance that fills microscopic gaps or pores within the material that allow for ingress of water or water vapor; coating and/or compounding the material with a water scavenger or hygroscopic material that can absorb, adsorb or react with water so as to increase the water resistance or impermeability of the material.

One type of material that may be employed as a coating to increase water resistance and/or water impermeability is an inorganic material. Inorganic materials include, but are not limited to, metals, metal oxides and other metal compounds (e.g. metal sulfides, metal hydrides), ceramics, and main group materials and their compounds (e.g. carbon (e.g. carbon nanotubes), silicon, silicon oxides). Examples of suitable materials include aluminum oxides (e.g. $Al_2O_3$) and silicon oxides (e.g. $SiO_2$). Inorganic materials may be advantageously coated onto a material (at any stage of manufacture of the material or implant) using techniques such as are known in the art to create extremely thin coatings on a substrate, including by vapor deposition, atomic layer deposition, plasma deposition, and the like. Such techniques can provide for the deposition of very thin coatings (e.g. about 20 nm-40 nm thick, including about 25 nm thick, about 30 nm thick, and about 35 nm thick) on substrates, including polymeric substrates, and can provide a coating on the exterior and/or interior luminal surfaces of small tubing, including that of the size suitable for use in implants disclosed herein. Such coatings can provide excellent resistance to the permeation of water or water vapor while still being at least moderately flexible so as not to undesirably compromise the performance of an implant in which flexibility is desired.

The drugs carried by the drug delivery implant may be in any form that can be reasonably retained within the device and results in controlled elution of the resident drug or drugs over a period of time lasting at least several days and in some embodiments up to several weeks, and in certain preferred embodiments, up to several years. Certain embodiments utilize drugs that are readily soluble in ocular fluid, while other embodiments utilize drugs that are partially soluble in ocular fluid.

For example, the therapeutic agent may be in any form, including but not limited to a compressed pellet, a solid, a capsule, multiple particles, a liquid, a gel, a suspension, slurry, emulsion, and the like. In certain embodiments, drug particles are in the form of micro-pellets (e.g., micro-tablets), fine powders, or slurries, each of which has fluid-like properties, allowing for recharging by injection into the inner lumen(s).

Figure 11:
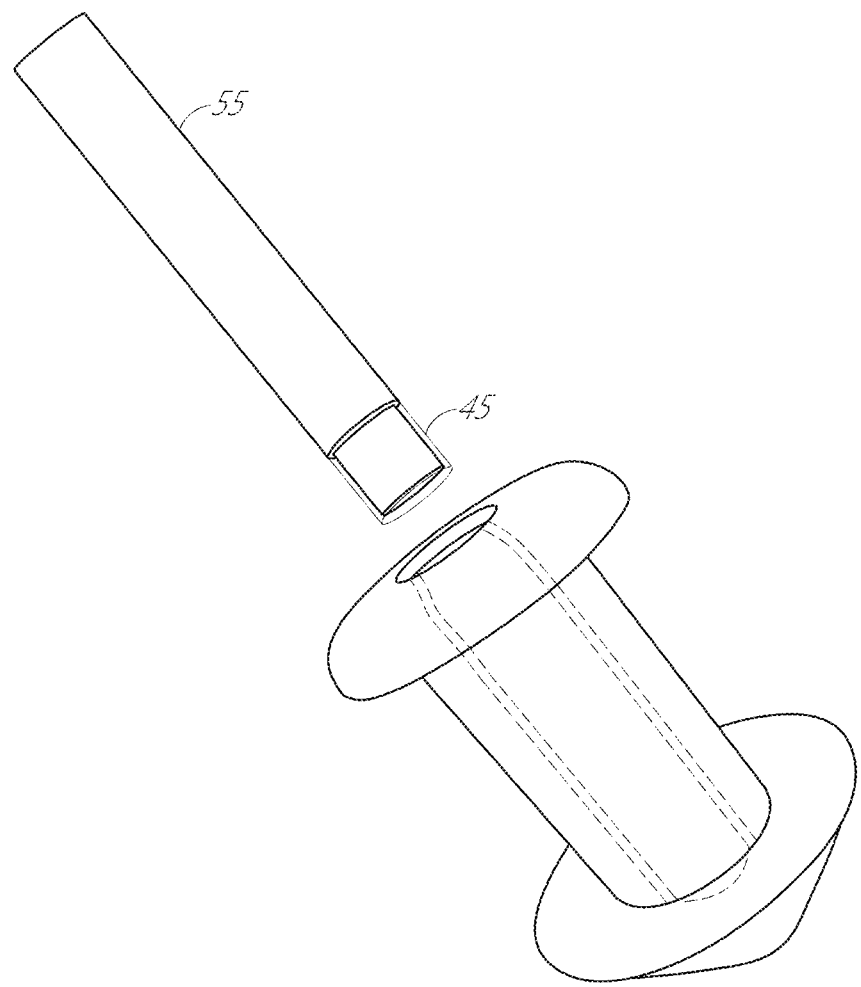
FIG. 11 illustrates an embodiment of an implant in which the implant is rechargeable in that an additional, or substitute, drug payload can be added to implant without requiring removal of the implant.

As discussed above, in some embodiments, the implants can be recharged, which in several embodiments, is accomplished with a syringe/needle, through which a therapeutic agent is delivered. In some embodiments, micro-tablets are delivered through a needle of about 23 gauge to about 32 gauge, including 23-25 gauge, 25 to 27 gauge, 27-29 gauge, 29-30 gauge, 30-32 gauge, and overlapping ranges thereof. In some embodiments, the needle is 23, 24, 25, 26, 27, 28, 29, 30, 31, or 32 gauge. In some embodiments, as described above, a drug sleeve surrounding a drug core is used to recharge an implant, as shown, for example, in FIG. 11. As shown in FIG. 11, for example, the drug core and drug sleeve can be removed together by drawing drug core proximally, and then a replacement core within a replacement drug sleeve can be inserted together by advancing the replacement core and sleeve 45 attached to an inserter tool 55 into the lumen or cavity of the implant. In some embodiments, implants comprised of hydrogel utilize the drug load inserter with the exchangeable drug core and drug sleeve. In some embodiments, one size of a hydrogel plug will fit all patients.

Figure 12:
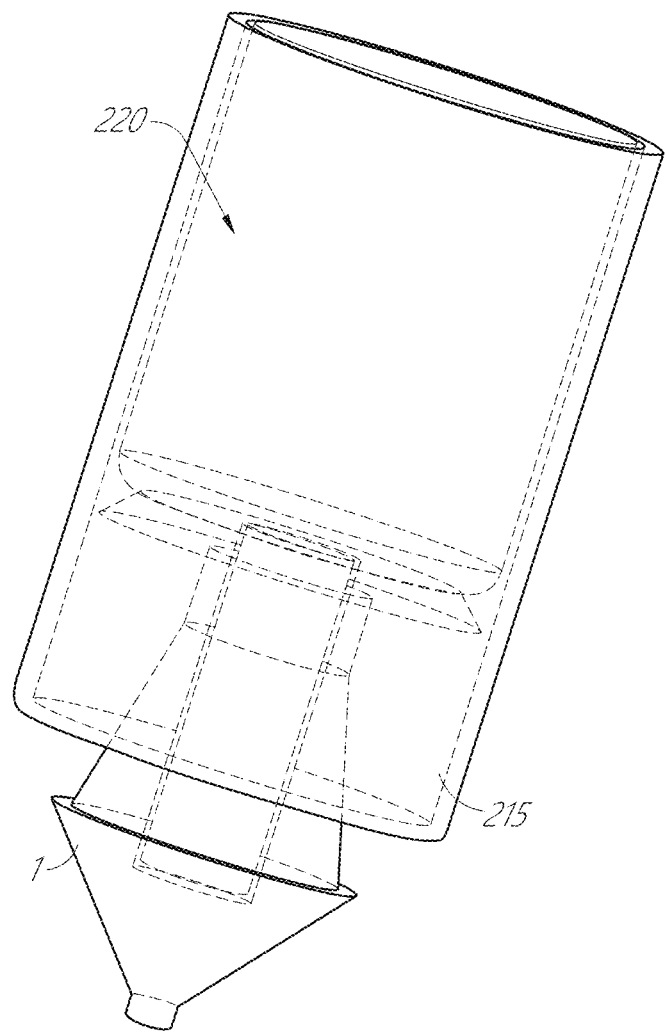
FIG. 12 illustrates an embodiment of an implant delivery system comprising a plunger for use with a preloaded drug implant.
Figure 13A:
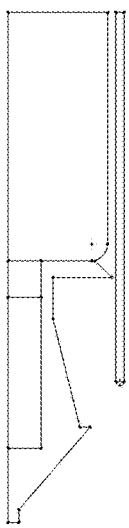
FIGS. 13A-13C illustrate schematic cross sections of embodiments of inserter tools in accordance with disclosure provided herein.
Figure 13B:
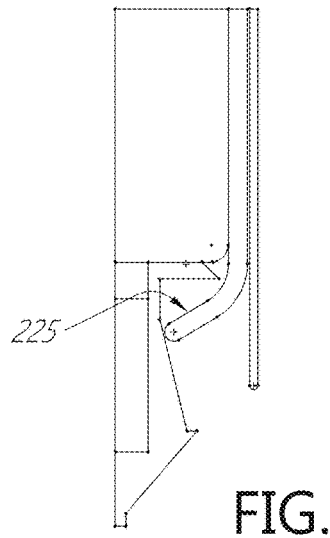
Figure 13C:
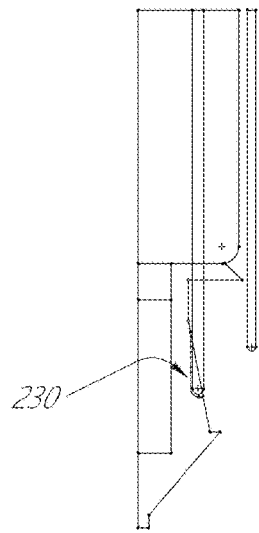

In several embodiments, however, recharging of the implant is not performed, in favor of replacing the implant with a new, drug-preloaded implant, based at least in part on the ease of access to the implant site (e.g., the punctum). In these embodiments, an inserter tool is used to insert the implant into the implant site. FIG. 12 shows the terminal aspect of an inserter tool 215 used to insert an implant into an implant site, the inserter comprising a plunger 220 that can be depressed and a preloaded drug implant 1 held within the terminus of the inserter prior to insertion, according to some embodiments. It is to be understood that the forceps and other insertion tools may be used to place an implant in the punctum and into the lacrimal canaliculus. In some embodiments, the distal edge of the inserter tool is parallel with the implant, as illustrated in FIG. 13A. In other words, as illustrated in FIG. 13A, the inserter tool can optionally have a straight cut tip. In some embodiments, the inserter tool contains at least one additional gripping component 225 that guides and supports the implant into the implant site, as shown, for example, in FIG. 13B. Such a gripper may be movably connected to a handpiece that allows for engagement and disengagement of the gripper. In some embodiments, the distal edge of the inserter tool is asymmetric in relation to the implant, as shown in FIG. 13C. In other words, in some embodiments, the distal end of the inserter tool 230 may optionally have a beveled or angled cut tip, which can act as a lead-in. Testing has shown beveled cut tip allowed easier entry of the inserter into the punctum over the straight cut tip. In sonic embodiments, the lead-in may also be used as a dilator to pre-dilate the area prior to insertion of an implant.

In one embodiment, a portion of the insertion tool may be made of clear material, for example, such as an acrylic material, so that the physician can visualize the tissue through the insertion tool and see the punctum. The optionally clear material may also allow viewing of an implant while it is being implanted, and may also confirm that the implant is implanted properly. In another embodiment, the clear material may be a magnifying material and/or have a magnifying geometry, such as a spherical lens or angled lens, so that the punctum is more easily visualized.

When more than one drug is desired for treatment of a particular pathology or when a second drug is administered such as to counteract a side effect of the first drug, some embodiments may utilize two agents of the same form. In other embodiments, agents in different form may be used. Likewise, should one or more drugs utilize an adjuvant, excipient, or auxiliary compound, for example to enhance stability or tailor the elution profile, that compound or compounds may also be in any form that is compatible with the drug and can be reasonably retained with the implant.

In some embodiments, treatment of particular pathology with a drug released from the implant may not only treat the pathology, but also induce certain undesirable side effects.

It will be understood that embodiments as described herein may include a drug mixed or compounded with a biodegradable material, excipient, or other agent modifying the release characteristics of the drug. In several embodiments, such biodegradable materials include copolymers of lactic acid and glycolic acid, also known as poly (lactic-co-glycolic acid) or PLGA. It will be understood by one skilled in the art that although some disclosure herein specifically describes use of PLGA, other suitable biodegradable materials may be substituted for PLGA or used in combination with PLGA in such embodiments. It will also be understood that in certain embodiments as described herein, the drug positioned within the lumen of the implant is not compounded or mixed with any other compound or material, thereby maximizing the volume of drug that is positioned within the lumen.

It may be desirable, in some embodiments, to provide for a particular rate of release of drug from a PLGA copolymer, other polymeric material, or other excipient. As the release rate of a drug from a polymer correlates with the degradation rate of that polymer, control of the degradation rate provides a means for control of the delivery rate of the drug contained within the therapeutic agent. Variation of the average molecular weight of the polymer or copolymer chains which make up the PLGA copolymer or other polymer may be used to control the degradation rate of the copolymer, thereby achieving a desired duration or other release profile of therapeutic agent delivery to the eye.

In certain other embodiments employing PLGA copolymers, rate of biodegradation of the PLGA copolymer may be controlled by varying the ratio of lactic acid to glycolic acid units in a copolymer.

Still other embodiments may utilize combinations of varying the average molecular weights of the constituents of the copolymer and varying the ratio of lactic acid to glycolic acid in the copolymer to achieve a desired biodegradation rate.

As described above, the outer shell of the implant comprises a polymer in some embodiments. Additionally, the shell may further comprise one or more polymeric coatings in various locations on or within the implant. The outer shell and any polymeric coatings are optionally biodegradable. The biodegradable outer shell and biodegradable polymer coating may be any suitable material including, but not limited to, poly(lactic acid), polyethylene-vinyl acetate, polylactic-co-glycolic acid), poly(D,L-lactide), poly(D,L-lactide-co-trimethylene carbonate), collagen, heparinized collagen, poly(caprolactone), poly(glycolic acid), and/or other polymer or copolymer.

As described above, some embodiments of the implants comprise a release material that is permeable to the drug (or drugs) and allows passage of the drug (or drugs) through the material in a controlled fashion. Control of the release of the drug can further be controlled by coatings in or on the implant (e.g., a coating over the release material that slows the rate of release of a drug).

For example, a given combination of drug and release material will yield a characteristic diffusion coefficient D, such that:

$$\text{Elution rate} = \frac{[D \times A \times (C_i - C_o)]}{d}$$

where D=diffusion coefficient (cm²/sec)
A=area of the region of drug release material
($C_i$–$C_o$)=difference in drug concentration between the inside and outside of the device.
d=thickness of the region of release material Thus, the area and thickness of the region of drug release are variables that determine, in part, the rate of elution of the drug from the implant, and are also variables that can be controlled during the process of manufacturing the implant. In some embodiments using a highly insoluble drug, the release material could be manufactured to be thin (d is small) or with a large overall area (A is large) or a combination of the two (as dictated by the structural sufficiency of the outer shell). In either case, the end result is that the elution rate of the drug can be increased to compensate for the low solubility of the drug based on the structure and design of the implant.

In contrast, in some embodiments using a highly soluble drug, the drug release material can be made thicker, more dense, or more concentrated, thereby adjusting the rate of release of the drug from the implant.

Additionally, certain embodiments use additional polymer coatings to either (i) increase the effective thickness (d) of the drug release material or (ii) decrease the overall permeability of the drug release material, resulting in a reduction in drug elution. In still other embodiments, multiple additional polymer coatings are used. By covering either distinct or overlapping portions of the implant and the drug release material, a controlled pattern of drug release from the implant overall can be achieved.

In several embodiments as described herein, there are no direct through holes or penetrating apertures needed or utilized to specifically facilitate or control drug elution. As such, in those embodiments, there is no direct contact between the drug core (which may be of very high concentration) and the ocular tissue where adjacent to the site where the implant is positioned. In some cases, direct contact of ocular tissue with high concentrations of drug residing within the implant could lead to local cell toxicity and possible local cell death. Thus, in several embodiments, the drug release material also serves a safety function.

As described above, duration of drug release is desired over an extended period of time. In some embodiments, an implant in accordance with embodiments described herein is capable of delivering a drug at a controlled rate to a target tissue for a period of several (i.e. at least three) months. In certain embodiments, implants can deliver drugs at a controlled rate to target tissues for about 6 months or longer, including 3, 4, 5, 6, 7, 8, 9, 12, 15, 18, and 24 months, without requiring recharging. In still other embodiments, the duration of controlled drug release (without recharging of the implant) exceeds 2 years (e.g., 3, 4, 5, or more years). It shall be appreciated that additional time frames including ranges bordering, overlapping or inclusive of two or more of the values listed above are also used in certain embodiments.

In conjunction with the controlled release of a drug to a target tissue, certain doses of a drug (or drugs) are desirable over time, in certain embodiments. As such, in some embodiments, the total drug load, for example the total load of a steroid, delivered to a target tissue over the lifetime of an implant ranges from about 10 to about 1000 µg. In certain embodiments the total drug load ranges from about 100 to about 900 µg, from about 200 to about 800 µg, from about 300 to about 700 µg, or from about 400 to about 600 µg. In some embodiments, the total drug load ranges from about 10 to about 300 µg, from about 10 to about 500 µg, or about 10 to about 700 µg. In other embodiments, total drug load ranges from about 200 to about 500 µg, from 400 to about 700 µg or from about 600 to about 1000 µg. In still other embodiments, total drug load ranges from about 200 to about 1000 µg, from about 400 to about 1000 µg, or from about 700 to about 1000 µg. In some embodiments total drug load ranges from about 500 to about 700 µg, about 550 to about 700 µg, or about 550 to about 650 µg, including 575, 590, 600, 610, and 625 µg. It shall be appreciated that additional ranges of drugs bordering, overlapping or inclusive of the ranges listed above are also used in certain embodiments.

Similarly, in other embodiments, controlled drug delivery is calculated based on the elution rate of the drug from the implant. In certain such embodiments, an elution rate of a drug, for example, a steroid, is about 0.05 µg/day to about 10 µg/day is achieved. In other embodiments an elution rate of about 0.05 µg/day to about 5 µg/day, about 0.05 µg/day to about 3 µg/day, or about 0.05 µg/day to about 2 µg/day is achieved. In other embodiment, an elution rate of about 2 µg/day to about 5 µg/day, about 4 µg/day to about 7 µg/day, or about 6 µg/day to about 10 µg/day is achieved. In other embodiments, an elution rate of about 1 µg/day to about 4 µg/day, about 3 µg/day to about 6 µg/day, or about 7 µg/day to about 10 µg/day is achieved. In still other embodiments, an elution rate of about 0.05 µg/day to about 1 µg/day, including 0.06, 0.07, 0.08, 0.09, 0.1, 0.2, 0.3, 0.4, 0.5, 0.6, 0.7, 0.8, or 0.9 µg/day is achieved. It shall be appreciated that additional ranges of drugs bordering, overlapping or inclusive of the ranges listed above are also used in certain embodiments.

Alternatively, or in addition to one or more of the parameters above, the release of drug from an implant may be controlled based on the desired concentration of the drug at target tissues. In some embodiments, the desired concentration of a drug, for example, a steroid, at the target tissue, ranges from about 1 nM to about 100 nM. In other embodiments the desired concentration of a drug at the site of action ranges from about 10 nM to about 90 nM, from about 20 nM to about 80 nM, from about 30 nM to about 70 nM, or from about 40 nM to about 60 nM. In still other embodiments the desired concentration of a drug at the site of action ranges from about 1 nM to about 40 nM, from about 20 nM to about 60 nM, from about 50 nM to about 70 nM, or from about 60 nM to about 90 nM. In yet other embodiments the desired concentration of a drug at the site of action ranges from about 1 nM to about 30 nM, from about 10 nM to about 50 nM, from about 30 nM to about 70 nM, or from about 60 nM to about 100 nM. In some embodiments, the desired concentration of a drug at the site of action ranges from about 45 nM to about 55 nM, including 46, 47, 48, 49, 50, 51, 52, 53, and 54 nM. It shall be appreciated that additional ranges of drugs bordering, overlapping or inclusive of the ranges listed above are also used in certain embodiments.

Drugs

In some embodiments, as discussed above, the drug or drugs employed may take one or more forms. For example, multiple pellets of single or multiple drug(s) are placed within an interior lumen of the implant (see, e.g., FIG. 4).

In some embodiments, the therapeutic agent (or agents) is formulated as micro-pellets or micro-tablets. Additionally, in some embodiments, micro-tablets allow a greater amount of the therapeutic agent to be used in an implant. This is because, in some embodiments, tabletting achieves a greater density in a pellet than can be achieved by packing a device. Greater amounts of drug in a given volume may also be achieved by decreasing the amount of excipient used as a percentage by weight of the whole tablet, which has been found by the inventors to be possible when creating tablets of a very small size while retaining the integrity of the tablet. In some embodiments, the percentage of active therapeutic (by weight) is about 70% or higher. As discussed herein, the therapeutic agent can be combined with excipients or binders that are known in the art. In some embodiments, the percentage of therapeutic agent ranges from about 70% to about 95%, from about 75 to 85%, from about 75 to 90%, from about 70 to 75%, from about 75% to about 80% from about 80% to about 85%, from about 85% to about 90%, from about 90% to about 95%, from about 95% to about 99%, from about 99% to about 99.9%, and overlapping ranges thereof. In some embodiments, the percentage of therapeutic agent ranges from about 80% to about 85%, including 81, 82, 83, and 84% by weight.

In several embodiments, micro-tablets provide an advantage with respect to the amount of an agent that can be packed, tamped, or otherwise placed into an implant disclosed herein. The resultant implant comprising micro-tablets, in some embodiments, thus comprises therapeutic agent at a higher density than can be achieved with non-micro-tablet forms. For example, in some embodiments, the density of the micro-pellet form of an agent within an implant ranges from about 0.7 g/cc to about 1.6 g/cc. In some embodiments, the density used in an implant ranges from about 0.7 glee to about 0.9 g/cc, from about 0.9 g/cc to about 1.1 g/cc, from about 1.1 g/cc to about 1.3 g/cc, from about 1.1 g/cc to about 1.5 g/cc, from about 1.3 g/cc to about 1.5 g/cc, from about 1.5 g/cc to about 1.6 g/cc, and overlapping ranges thereof. In some embodiments, densities of therapeutic agent that are greater than 1.6 g/cc are used.

In one embodiment, micro-tablets with the above properties, or any combination thereof, are made using known techniques in the art including tableting, lyophilization, granulation (wet or dry), flaking, direct compression, molding, extrusion, and the like. Moreover, as discussed below, alterations in the above-discussed characteristics can be used to tailor the release profile of the micro-tableted therapeutic agent from an implant.

In several embodiments, lyophilization of a therapeutic agent is used prior to the micro-pelleting process. In some embodiments, lyophilization improves the stability of the therapeutic agent once incorporated into a micro-tablet. In some embodiments, lyophilization allows for a greater concentration of therapeutic to be obtained prior to micro-pelleting, thereby enhancing the ability to achieve the high percentages of active therapeutic agents that are desirable in some embodiments. For example, many commercially available therapeutic agents useful to treat ocular diseases are developed as first-line agents for other diseases. As such, their original formulation may not be suitable or ideal for micro-pelleting or for administration to an ocular target via an ocular implant such as those disclosed herein. For example, several anti-VEGF compounds are supplied as sterile liquid in single use vials meant to be administered intravenously (e.g., bevacizumab). As a result, such a liquid formulation is less preferred for formation of micro-pellets as compared to a solid, though a liquid therapeutic agent may optionally be used in some embodiments. To achieve micro-pelleting at high percentages of therapeutic agent, such liquid formulations may be frozen (e.g., stored at temperatures between −20° C. and −80° C. for 16 to 24 hours or longer) and then subject to lyophilization until dry. Alternatively, air spraying, crystallization, or other means may optionally be used to dry the therapeutic agent.

Once dry, the lyophilized (or otherwise dried) therapeutic agent is optionally tested for purity. In some embodiments, solvents may be added to a liquid (or solid) formulation in order to dissolve and remove (via evaporation) non-therapeutic components (e.g., excipients or inert binding agents). In some embodiments, a therapeutic agent is purified by conventional methods (e.g., antibody-based chromatography, HPLC, etc.) prior to lyophilization. In such embodiments, lyophilization often functions to increase the concentration of the therapeutic agent in the recovered purified sample.

In some embodiments, the dried therapeutic agent (which, for efficiency purposes is optionally dried in bulk) is ground, sieved, macerated, freeze-fractured, or subdivided into known quantities by other means, and then micro-pelleted.

After lyophilization and or subdivision, the therapeutic agent is fed into a micro-pelleting process. In some embodiments, standard techniques (e.g., compression, extrusion, molding, or other means) are used. However, in several embodiments employing high percentages of active therapeutic agent, more specialized techniques are used.

In several embodiments, the therapeutic agent is a protein, and in such embodiments, drying and/or tabletization should be completed under conditions (e.g., temperature, acid/base, etc.) that do not adversely affect the biological activity of the therapeutic agent. To assist in maintenance of biological activity of micro-pelleted therapeutic agents, in some embodiments, protein therapeutics are formulated with a. stabilizing agent (e.g., mannitol, trehalose, starch, or other poly-hydroxy polymer) to maintain the structure (and therefore activity) of the therapeutic protein.

As mentioned above, depending on the embodiment, the drug or drugs to be administered via the drug delivery implant may be in the form of a nanodispersion. Nanodispersions are pariticularly advantageogus when the drug (or drugs) to be administered is poorly soluble or insoluble in aqueous solutions, which can lead to instability and/or reduced bioavailability.

As used herein, the term "nanodispersion" shall be given its ordinary meaning and shall refer to a composition comprising nanoparticles comprising a drug and/or an aqueous vehicle. In several embodiments, the aqueous vehicle comprises a water miscible solvent and water. In several embodiments, the nanoparticles may comprise a drug, a polymer and a surfactant comprising a mixture of fatty acids or its salts and sterol or its derivatives or its salts, in some embodiments.

The term "nanoparticle" as used herein shall be given its ordinary meaning and shall also refer to particles having controlled dimensions of the order of nanometers. For example the nanoparticles, in several embodiments, are a polymeric nanoparticle (matrix of polymer entrapping the drug) and/or a polymeric nanovesicle (polymer stabilized nano sized vesicle encapsulating the drug.) and/or a polymeric nanocapsule (polymeric membrane surrounding drug in core) and/or nano sized particles of the drug stabilized by surfactants, and the like the nanoparitcles having mean size less than about 300 nm (e.g., ranging from about 10 nm to about 275 nm, or in the range of about 10 nm to about 200 nm.

In several embodiments, the water miscible solvent used in the nanodispersion comprises one or more of alcohols, glycols and its derivatives, polyalkylene glycols and its derivatives, glycerol, glycofurol and combinations thereof. Additonal non-limiting examples include, but are not limited to, alcohols such as ethanol, n-propanol, isopropanol; glycols such as ethylene glycol, propylene glycol, butylene glycol and its derivatives; polyethylene glycols like PEG 400 or PEG 3350; polypropylene glycol and its derivatives such as PPG-10 butanediol, PPG-10 methyl glucose ether, PPG-20 methyl glucose ether, PPG-15 stearyl ether; glycerol; glycofurol and the like and mixtures thereof. In still additional embodiments, the non-aqueous solvent is selected from the group consisting of alcohols, polyethylene glycols and/or mixtures thereof, such as, for example, a mixture of ethanol and PEG (polyethylene glycol). In some embodiments, in which ethanol is used in the nanodispersion, ethanol is present in an amount ranging from about 0.001% w/v to about 5% w/v, more preferably from about 0.05% w/v to about 0.5% w/v and most preferably from about 0.1% w/v to about 0.25% w/v. Polyethylene glycols which are used preferably, include PEG-400 and PEG-3350. PEG-400 is used, depending on the embodiment, in an amount ranging from about 0.01% w/v to about 20.0% w/v, more preferably from about 0.05% w/v to about 5.0% w/v and most preferably from about 1.0% w/v to about 2.5% w/v. PEG-3350 is used, depending on the embodiment, in an amount ranging from about 0.001% w/v to about 10.0% w/v, more preferably from about 0.05% w/v to about 5.0% w/v and most preferably from about 0.1% w/v to about 3% w/v.

In some embodiments, the nanoparticles comprise one or more polymers. The polymer(s) used in several embodiments are preferably, water soluble. Polyvinylpyrrolidone, one such water soluble polymer used in several embodiments, is a tertiary amide polymer having linearly arranged monomer units of 1-vinyl-2-pyrrolidone. It has mean molecular weights ranging from about 10,000 to about 700,000. Other grades of polyvinylpyrrolidone are used in some embodiments, with molecular weights ranging from about 2000 to about 3000, about 7000 to about 11,000, about 28,000 to about 34,000, or about 1,000,000 to about 1,5000, 000. In still additional embodiments, polyvinylpyrrolidone use for the polymer have molecular weight in the range from about 1,000 to about 45,000, preferably, from about 4,000 to about 30,000. According several embodiments, the amount of polymer used in the nanodispersion ranges from about 0.001% w/v to about 20% w/v, including preferably about 0.01% w/v to about 5.0% w/v and also about 0.01% w/v to about 1.0% w/v.

Polyethylene glycol is used in several embodiments, either in addition or in place of polyvinylpyrrolidone. In several embodiments, the amount of polymer used in the nanodispersion ranges from about 0.001% w/v to about 20% w/v, including about 0.01% w/v to about 5.0% w/v, and in some embodiments, about 0.01% v/v to about 1.0% w/v.

Surfactants are used in some embodiments of the nanodispersions for drug(s). In several embodiments, the surfactants comprise a mixture of fatty acid or its salts and sterol or its derivatives or its salts.

As used herein, the term "fatty acids" shall be given its ordinary meaning and shall also include aliphatic (saturated or unsaturated) monocarboxylic acids derived from or contained in esterified form, in an animal or vegetable fat, oil or wax. Non-limiting examples of fatty acids (or its salts) that may be used in in several embodiments include, but are not limited to, fatty acids or its salts having 'n' number of carbon atoms wherein 'n' ranges from about 4 to about 28. The fatty acid may be a saturated fatty acid or an unsaturated fatty acid, and their salt and combinations thereof. Depending on the embodiment, the saturated fatty acid and its salts may be selected from butyric acid, caproic acid, caprylic acid, capric acid, lauric acid, myristic acid, palmitic acid, stearic acid, arachidic acid, behenic acid, sodium caprylate, sodium laurate, sodium myristate, sodium palmitate and the like and/or mixtures thereof. The unsaturated fatty acid and its salts may be selected from myristoleic acid, palmitoleic acid, oleic acid, linoleic acid, alpha linolenic acid, arachidonic acid, cicosapentaenoic acid, erucic acid, docosahexaenoic acid, sodium oleate, sodium arachidonate and the like and/or mixtures thereof.

Additonally, non-limiting examples, of sterol or its derivative or its salts that may be used in the nanodispersion or nanoparticles may be acid esters of sterols. The sterols that may be suitable, but are not limited to, cholesterol, phytosterols, ergosterol, bile acids salts and mixtures thereof. Acid salts of cholesterol that may be used include, but are not limited to, cholesteryl sulfate, cholesterol acetate, cholesterol chloroacetate, cholesterol benzoate, cholesterol myristate, cholesterol hemisuccinate, cholesterol phosphate, cholesterol phosphate, phosphonate, borate, nitrate, cholesterol cinnamate, cholesterol crotanoate, cholesterol butyrate, cholesterol heptanoate, cholesterol hexanoate, cholesterol octanoate, cholesterol nonanoate, cholesterol decanoate, cholesterol oleate, cholesterol propionate, cholesterol valerate, dicholestervl carbonate and the like and mixtures thereof. Phytosterols that may be used in the compositions include sitosterol, campesterol, stigmasterol, brassicasterol and its derivatives, salts and mixture thereof. For example, Phytosterols marketed by Sigma, U.S.A. containing bsitosterol, campesterol and dihydrobrassicasterol. Bile acids include cholic acid, chenodeoxycholic acid, deoxycholic acid, glycocholic acid, taurocholic acid, ursodeoxycholic acid and its derivatives, salts and mixture thereof. The sterols can also be esters of cholesterol including cholesterol hemi-succinate, salts of cholesterol including cholesterol hydrogen sulfate and cholesterol sulfate, ergosterol, esters of ergosterol including ergosterol hemi-succinate, salts of ergosterol including ergosterol hydrogen sulfate and ergosterol sulfate, lanosterol, esters of lanosterol including lanosterol hemi-succinate, salts of lanosterol including lanosterol hydrogen sulfate and lanosterol sulfate.

According to one embodiment, the nanoparticles comprise a surfactant which is a mixture of sterol or its derivatives or its salts and fatty acids or its salts. In an additional embodiment, the nanoparticles comprise of cholesterol ester of polar acids. In still further embodiments, the surfactant used in the nanodispersion is a mixture of caprylic acid and cholesteryl sulfate. Caprylic acid, also known as octanoic acid may be used in such embodiments in an amount ranging from about 0.001% w/v to about 5.0% w/v, more preferably from about 0.01% w/v to about 1.0% w/v and most preferably from about 0.01% w/v to about 0.5% w/v. Cholesteryl sulfate is used in certain embodiments in an amount ranging from about 0.001% w/v to about 5.0% w/v, more preferably from about 0.01% w/v to about 1.0% w/v and most preferably from about 0.01% w/v to about 0.5% w/v. In one embodiment, the surfactant used is selected from oleic acid and cholesteryl sulphate and/or mixtures thereof. In some embodiments, the surfactant used is selected from saturated fatty acid and bile acid or bile salt and/or mixtures thereof. Bile salts, when used according to some embodiments, are present in an amount ranging from about 0.001% w/v to about 5.0% w/v, more preferably from about 0.01% w/v to about 1.0% w/v and most preferably from about 0.01% w/v to about 0.75% w/v. Other amounts may be used in conjunction with other embodiments disclosed herein. Nanodispersions can be generated by methods appreciated in the art, such as those methods (and the resulting nanodispersions) disclosed in U.S. Pat. No. 8,778,364, which is incorporated by reference in its entirety herein.

In addition, one or more of the therapeutic drug regions may comprise drug-cyclodextrin inclusion complexes; liposome encapsulation; micelles based on polymers such as polysaccharide, poly (ethylene glycol)-poly(lactide), methoxy polyethylene glycol)-poly(hexyl-lactide), or hydrophobically-modified hydroxypropylcellulose; nanoparticles of amorphous drug formed by antisolvent precipitation and stabilized with surfactant such as poysorbate 80 or polyoxyl 15 hydroxystearate; nanoparticles having a mean size less than 500 nm containing one or more drugs, a polymer, and a surfactant, where the surfactant may include a mixture of fatty acids or its salts and sterol or its derivitatives or its salts; drug co-processed or granulated with excipients such as microcrystalline cellulose, lactose, hydroxypropyl methyl cellulose, or povidone; added polyethylene glycol chains to the drug, polymer, or surfactant (PEGylation); solid dispersions in polymeric carriers such as hypromellose acetate succinate, copolymers based on dimethylaminoethyl methacrylate, butyl methacrylate, and methyl methacrylate, polyvinylpyrrolidone-vinyl acetate), or lauroyl macrogolglycerides; or microspheres (for example, based on PLGA or chitosan).

The therapeutic agents utilized with the drug delivery implant, may include one or more drugs provided below, either alone or in combination. The drugs utilized may also be the equivalent of, derivatives of, or analogs of one or more of the drugs provided below. The drugs may include but are not limited to pharmaceutical agents including anti-glaucoma medications, ocular agents, antimicrobial agents (e.g., antibiotic, antiviral, antiparasitic, antifungal agents), anti-inflammatory agents (including steroids or non-steroidal anti-inflammatory), biological agents including hormones, enzymes or enzyme-related components, antibodies or antibody-related components, oligonucleotides (including DNA, RNA, short-interfering RNA, antisense oligonucleotides, and the like), DNA/RNA vectors, viruses (either wild type or genetically modified) or viral vectors, peptides, proteins, enzymes, extracellular matrix components, and live cells configured to produce one or more biological components. The use of any particular drug is not limited to its primary effect or regulatory body-approved treatment indication or manner of use. Drugs also include compounds or other materials that reduce or treat one or more side effects of another drug or therapeutic agent. As many drugs have more than a single mode of action, the listing of any particular drug within any one therapeutic class below is only representative of one possible use of the drug and is not intended to limit the scope of its use with the ophthalmic implant system.

As discussed above, the therapeutic agents may be combined with any number of excipients as is known in the art. In addition to the biodegradable polymeric excipients discussed above, other excipients may be used, including, but not limited to, benzyl alcohol, ethylcellulose, methylcellulose, hydroxymethylcellulose, cetyl alcohol, croscarmellose sodium, dextrans, dextrose, fructose, gelatin, glycerin, monoglycerides, diglycerides, kaolin, calcium chloride, lactose, lactose monohydrate, maltodextrins, polysorbates, pregelatinized starch, calcium stearate, magnesium stearate, silicon dioxide, cornstarch, talc, and the like. The one or more excipients may be included in total amounts as low as about 1%, 5%, or 10% and in other embodiments may be included in total amounts as high as 50%, 70% or 90%.

Examples of drugs may include various anti-secretory agents; antimitotics and other anti-proliferative agents, including among others, anti-angiogenesis agents such as angiostatin, anecortave acetate, thrombospondin, VEGF receptor tyrosine kinase inhibitors and anti-vascular endothelial growth factor (anti-VEGF) drugs such as ranihizumab (LUCENTIS®) and bevacizumab (AVASTIN®), pegaptanib (MACUGEN®), aflihercept (EYLEA®), sunitinib and sorafenib and any of a variety of known small-molecule and transcription inhibitors having anti-angiogenesis effect; classes of known ophthalmic drugs, including: glaucoma agents, such as adrenergic antagonists, including for example, beta-blocker agents such as atenolol propranolol, metipranolol, betaxolol, carteolol, levobetaxolol, levobunolol and timolol; adrenergic agonists or sympathomimetic agents such as epinephrine, dipivefrin, clonidine, aparclonidine, and brimonidine; parasympathomimetics or cholingeric agonists such as pilocarpine, carbachol, phospholine iodine, and physostigmine, salicylate, acetylcholine chloride, eserine, diisopropyl fluorophosphate, demecarium bromide); muscarinics; carbonic anhydrase inhibitor agents, including topical and/or systemic agents, for example acetozolamide, brinzolamide, dorzolamide and methazolamide, ethoxzolamide, diamox, and dichlorphenamide; mydriatic-cycloplegic agents such as atropine, cyclopentolate, succinylcholine, homatropine, phenylephrine, scopolamine and tropicamide; prostaglandins such as prostaglandin F2 alpha, antiprostaglandins, prostaglandin precursors, or prostaglandin analog agents such as bimatoprost, latanoprost, travoprost and unoprostone.

Other examples of drugs may also include anti-inflammatory agents including for example glucocorticoids and corticosteroids such as betamethasone, cortisone, dexamethasone, dexamethasone 21-phosphate, methylprednisolone, prednisolone 21-phosphate, prednisolone acetate, prednisolone, fluoromethalone, loteprednol, medrysone, fluocinolone acetonide, triamcinolone acetonide, triamcinolone, triamcinolone acetonide, beclomethasone, budesonide, flunisolide, fluorometholone, fluticasone, hydrocortisone, hydrocortisone acetate, loteprednol, rimexolone and non-steroidal anti-inflammatory agents including, for example, diclofenac, flurbiprofen, ibuprofen, bromfenac; nepafenac, and ketorolac, salicylate, indomethacin, ibuprofen, naxopren, piroxicam and nabum.etone; anti-infective or antimicrobial agents such as antibiotics including, for example, tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, aminoglycosides such as gentamicin and tobramycin; fluoroquinolones such as ciprofloxacin, gatifloxacin, levofloxacin, moxifloxacin, norfloxacin, ofloxacin; bacitracin, erythromycin, fusidic acid, neomycin, polymyxin B, gramicidin, trimethoprim and sulfacetamide; antifungals such as amphotericin B and miconazole; antivirals such as idoxuridine trifluorothymidine, acyclovir, gancyclovir, interferon; antimicotics; immune-modulating agents such as antiallergenics, including, for example, sodium chmnoglycate, antazoline, methapyriline, chlorpheniramine, cetrizine, pyrilamine, prophenpyridamine; anti-histamine agents such as azelastine, emedastine and levocabastine; immunological drugs (such as vaccines, immune stimulants, and/or immunosuppressants); MAST cell stabilizer agents such as cromolyn sodium, ketotifen, lodoxamide, nedocrimil, olopatadine and pemirolastciliary body ablative agents, such as gentimicin and cidofovir; and other ophthalmic agents such as verteporfin, proparacaine, tetracaine, cyclosporine and pilocarpine; inhibitors of cell-surface glycoprotein receptors; decongestants such as phenylephrine, naphazoline, tetrahydrazoline; lipids or hypotensive lipids; dopaminergic agonists and/or antagonists such as quinpirole, fenoldopam, and ibopamine; vasospasm inhibitors; vasodilators; antihypertensive agents; angiotensin converting enzyme (ACE) inhibitors; angiotensin-1 receptor antagonists such as olmesartan; microtubule inhibitors; molecular motor (dynein and/or kinesin) inhibitors; actin cytoskeleton regulatory agents such as cyctchalasin, latnmculin, swinholide A, ethacrynic acid, H-7, and Rho-kinase (ROCK) inhibitors; remodeling inhibitors; modulators of the extracellular matrix such as tert-butylhydro-quinolone and AL-3037A; adenosine receptor agonists and/or antagonists such as N-6-cylclophexyladenosine and (R)-phenylisopropyladenosine; serotonin agonists; hormonal agents such as estrogens, estradiol, progestational hormones, progesterone, insulin, calcitonin, parathyroid hormone, peptide and vasopressin hypothalamus releasing factor; growth factor antagonists or growth factors, including, for example, epidermal growth factor, fibroblast growth factor, platelet derived growth factor or antagonists thereof (such as those disclosed in U.S. Pat. No. 7,759,472 or U.S. patent application Ser. Nos. 12/465,051, 12/564,863, or 12/641,270, each of which is incorporated in its entirety by reference herein), transforming growth factor beta, somatotrapin, fibronectin, connective tissue growth factor, bone morphogenic proteins (BMPs); cytokines such as interleukins, CD44, cochlin, and serum amyloids, such as serum amyloid A.

Other therapeutic agents may include neuroprotective agents such as lubezole, nimodipine and related compounds, and including blood flow enhancers such as dorzolamide or betaxolol; compounds that promote blood oxygenation such as erythropoeitin; sodium channels blockers; calcium channel blockers such as nilvadipine or lomerizinc; glutamate inhibitors such as memantine nitromemantine, riluzole, dextromethorphan or agmatine; acetylcholinsterase inhibitors such as galantamine; hydroxylamines or derivatives thereof, such as the water soluble hydroxylamine derivative OT-440; synaptic modulators such as hydrogen sulfide compounds containing flavonoid glycosides and/or terpenoids, such as ginkgo biloba; neurotrophic factors such as glial cell-line derived neutrophic factor, brain derived neurotrophic factor; cytokines of the IL-6 family of proteins such as ciliary neurotrophic factor or leukemia inhibitory factor; compounds or factors that affect nitric oxide levels, such as nitric oxide, nitroglycerin, or nitric oxide synthase inhibitors; cannabinoid receptor agonists such as WIN55-212-2; free radical scavengers such as methoxypolyethylene glycol thioester (MPDTE) or methoxypolyethylene glycol thiol coupled with EDTA methyl triester (MPSEDE); anti-oxidants such as astaxathin, dithiolethione, vitamin E, or metallocorroles (e.g., iron, manganese or gallium corroles); compounds or factors involved in oxygen homeostasis such as neuroglobin or cytoglobin; inhibitors or factors that impact mitochondrial division or fission, such as Mdivi-1 (a selective inhibitor of dynamin related protein 1 (Drp1)); kinase inhibitors or modulators such as the Rho-kinase inhibitor H-1152 or the tyrosine kinase inhibitor AG1478; compounds or factors that affect integrin function, such as the Beta 1-integrin activating antibody HUTS-21; N-acyl-thanaolamines and their precursors. N-acyl-ethanolamine phospholipids; stimulators of glucagon-like peptide 1 receptors (e.g., glucagon-like peptide 1); polyphenol containing compounds such as resveratrol; chelating compounds; apoptosis-related protease inhibitors; compounds that reduce new protein synthesis; radiotherapeutic agents; photodynamic therapy agents; gene therapy agents; genetic modulators; auto-immune modulators that prevent damage to nerves or portions of nerves (e.g., demyelination) such as glatimir; myelin inhibitors such as anti-NgR Blocking Protein, NgR (310)ecto-Fc; other immune modulators such as FK506 binding proteins (e.g., FKBP51); and dry eye medications such as cyclosporine, cyclosporine A, delmulcents, and sodium hyaluronate.

Other therapeutic agents that may be used include: other beta-blocker agents such as acebutolol, atenolol, bisoprolol, carvedilol, asmolol, labetalol, nadolol, penbutolol, and pindolol; other corticosteroidal and non-steroidal anti-inflammatory agents such aspirin, betamethasone, cortisone, diflunisal, etodolac, fenoprofen, fludrocortisone, flurbiprofen, hydrocortisone, ibuprofen, indomethacine, ketoprofen, meclofenamate, mefenamic acid, meloxicam, methylprednisolone, nabumetone, naproxen, oxaprozin, prednisolone, prioxicam, salsalate, sulindac and tolmetin; COX-2 inhibitors like celecoxib, rofecoxib and Valdecoxib; other immune-modulating agents such as aldesleukin, dalimumab (HUMIRA®), azathioprine, basiliximab, daclizumab, etanercept (ENBREL®), hydroxychloroquine, infliximah (REMICADE®), leflunomide, methotrexate, mycophenolate mofetil, and sulfasalazine; other anti-histamine agents such as loratadine, desloratadine, cetirizine, diphenhydramine, chlorpheniramine, dexchlorpheniramine, clemastine, cyproheptadine, fexofenadine, hydroxyzine and promethazine; other anti-infective agents such as aminoglycosides such as amikacin and streptomycin; anti-fungal agents such as amphotericin B, caspofungin, clotrimazole, fluconazole, itraconazole, ketoconazole, voriconazole, terbinafine and nystatin; anti-malarial agents such as chloroquine, atovaquone, mefloquine, primaquine, quinidine and quinine; anti-mycobacterium agents such as ethambutol, isoniazid, pyrazinamide, rifampin and rifabutin; anti-parasitic agents such as albendazole, mebendazole, thiobendazole, metronidazole, pyrantel, atovaquone, iodoquinaol, ivermectin, paromycin, praziquantel, and trimatrexate; other anti-viral agents, including anti-CMV or anti-hetpetic agents such as acyclovir, cidofovir, famciclovir, gangciclovir, valacyclovir, valganciclovir, vidarabine, trifluridine and foscarnet; protease inhibitors such as ritonavir, saquinavir, lopinavir, indinavir, atazanavir, amprenavir and nelfinavir; nucleotide/nucleoside/non-nucleoside reverse transcriptase inhibitors such as abacavir, ddI, 3TC, d4T, ddC, tenofovir and emtricitabine, delavirdine, efavirenz and nevirapine; other anti-viral agents such as interferons, ribavirin and trifluridiene; other anti-bacterial agents, including cabapenems like ertapenem, imipenem and meropenem; cephalosporins such as cefadroxil, cefazolin, cefdinir, cefditoren, cephalexin, cefaclor, cefepime, cefoperazone, cefotaxime, cefotetan, cefoxitin, cefpodoxime, cefprozil, ceftaxidime, ceftibuten, ceftizoxime, ceftriaxone, cefuroxime and loracarbef; other macrolides and ketolides such as azithromycin, clarithromycin, dirithromycin and telithromycin; penicillins (with and without clavulanate) including amoxicillin, ampicillin, pivampicillin, oxacillin, piperacillin, and ticarcillin; tetracyclines such as doxycycline, minocycline and tetracycline; other anti-bacterials such as aztreonam, chloramphenicol, clindamycin, linezolid, nitrofurantoin and vancomycin; alpha blocker agents such as doxazosin, prazosin and terazosin; calcium-channel blockers such as amlodipine, bepridil, diltiazem, felodipine, isradipine, nicardipine, nifedipine, nisoldipine and verapamil; other anti-hypertensive agents such as clonidine, diazoxide, fenoldopan, hydralazine, minoxidil, nitroprusside, phenoxybenzamine, epoprostenol, tolazoline, treprostinil and nitrate-based agents; anti-coagulant agents, including heparins and heparinoids such as heparin, dalteparin, enoxaparin, tinzaparin and thndaparinux; other anti-coagulant agents such as hirudin, aprotinin, argatroban, bivalirudin, desirudin, lepirudin, warfarin and ximelagatmn; anti-platelet agents such as abciximab, clopidogrel, dipyridamole, optifibatide, ticlopidine and tirofiban; prostaglandin PDE-5 inhibitors and other prostaglandin agents such as alprostadil, carboprost, sildenafil, tadalafil and vardenafil; thrombin inhibitors; antithrombogenic agents; anti-platelet aggregating agents; thrombolytic agents and/or fibrinolytic agents such as alteplase, anistreplase, reteplase, streptokinase, tenecteplase and urokinase; anti-proliferative agents such as sirolimus, tacroliinus, everolimus, zotarolimus, paclitaxel and mycophenolic acid; hormonal-related agents including levothymxine, fluoxymestrone, methyltestosterone, nandrolone, oxandrolone, testosterone, estradiol, estrone, estropipate, clomiphene, gonadotropins, hydroxyprogesterone, levonorgestrel, medroxyprogesterone, megestrol, mifepristone, norethindrone, oxytocin, progesterone, raloxifene and tamoxifen; anti-neoplastic agents, including alkylating agents such as carmustine lomustine, melphalan, cisplatin, fluorouracil3, and procarbazine antibiotic-like agents such as bleomycin, daunorubicin, doxorubicin, idarubicin, mitomycin and plicamycin; anti proliferative agents (such as 1,3-cis retinoic acid, 5-fluorouracil, taxol, rapamycin, mitomycin C and cisplatin); antimetabolite agents such as cytarabine, fludarabine, hydroxyurea, mercaptopurine and 5-fluorouracil (5-FU); immune modulating agents such as aldesleukin, imatinib, rituximab and tositumoinab; mitotic inhibitors docetaxel, etoposide, vinblastine and vincristine; radioactive agents such as strontium-89; and other anti-neoplastic agents such as irinotecan, topotecan and mitotane.

While certain embodiments of the disclosure have been described, these embodiments have been presented by way of example only, and are not intended to limit the scope of the disclosure. Indeed, the novel methods, systems, and devices described herein may be embodied in a variety of other forms. For example, embodiments of one illustrated or described implant may be combined with embodiments of another illustrated or described shunt. Moreover, the implants described above may be utilized for other purposes. For example, the implants may be used to drain fluid from the anterior chamber to other locations of the eye or outside the eye. Furthermore, various omissions, substitutions and changes in the form of the methods, systems, and devices described herein may be made without departing from the spirit of the disclosure.

What is claimed is:
1. A punctal implant for insertion into a punctum of the eye of a subject and configured to deliver two or more drugs to the eye of the subject, the implant comprising:
an outer shell comprising (i) a proximal end comprising at least one region of drug release and an asymmetrical flange, (ii) a closed distal end, and (iii) an interior lumen comprising at least two drugs positioned within the lumen, wherein the region of drug release comprises an occlusive member that is permeable to said two or more drugs, the occlusive member positioned at least partially within the interior lumen, wherein said occlusive member allows elution of the two or more drugs to occur only through the occlusive member, wherein the thickness of the occlusive member at least partially defines the elution rate of the two or more drugs, wherein the asymmetrical flange has a length extending in a first direction that exceeds a width extending in a second direction and is configured to rest on the surface of the eyelid when the implant is inserted into the punctum, wherein the first and second drug elute from the lumen to the tear film of the eye of the subject by passing through the at least one region of drug release, and wherein the first drug is a discontinuous first phase dispersed within the second drug.

2. The implant of claim 1, wherein the occlusive member is dimensioned based on the permeability of said occlusive member to said first and second drugs and the desired relative timing and duration of elution of said first and second drugs.

3. The implant of claim 1, wherein the occlusive member is integrally formed with the outer shell of the implant.

4. The implant of claim 1, wherein the occlusive member further comprises randomly or patterned holes through the occlusive member.

5. The implant of claim 1, wherein the first drug is placed in a more proximal position within the interior lumen relative to the position of the second drug.

6. The implant of claim 1, wherein the second drug provides an environment that improves the stability of the first drug.

7. A punctal implant for insertion into a punctum of the eye of a subject and configured to deliver two or more drugs to the eye of the subject, the implant comprising:

an outer shell comprising (i) a proximal end comprising at least one region of drug release and an asymmetrical flange, (ii) a closed distal end, (iii) an interior lumen comprising at least two drugs positioned within the lumen, wherein the region of drug release comprises an annular ring component comprising a material that is permeable or semi-permeable to at least one of the two or more drugs, the annular ring component defining an aperture, wherein the annular ring component is positioned at the proximal-most portion of the interior lumen and entirely within the interior lumen, wherein said aperture allows elution of the two or more drugs to occur through the annular ring component, wherein the dimensions of the aperture at least partially define the elution rate of the two or more drugs, wherein the diameter of the aperture is smaller than a diameter of the interior lumen, wherein the asymmetrical flange has a length extending in a first direction that exceeds a width extending in a second direction and is configured to rest on the surface of the eyelid when the implant is inserted into the punctum, and wherein the first and second drug elute from the lumen to the tear film of the eye of the subject by passing through the at least one region of drug release.

8. The implant of claim 7, wherein the outer shell comprises a radial bulge in a distal region in order to anchor the implant in the punctum.

9. An implant according to claim 7, wherein the first drug elutes for a period of between 1 and 75 days, and second drug elutes for a period of time ranging from about 1 to about 24 months after the first drug is eluted.

10. An implant according to claim 7, wherein the implant has a length of between about 0.5 and about 2.5 mm.

11. An implant according to claim 7, wherein the implant has a diameter of about 0.2 to about 1.5 mm.

12. An implant according to claim 7, wherein the first drug is a steroid.

13. The implant of claim 12, wherein the steroid is selected from the group consisting of loteprednol etabonate, dexamethasone, and triamcinolone acetonide.

14. An implant according to claim 7, wherein the second drug is cyclosporine and is optionally formulated as a nanodispersion.

15. An implant according to claim 7, wherein the first drug facilitates tear production.

16. The punctal implant of claim 1, wherein the occlusive member comprises two or more holes.

17. The punctal implant of claim 1, wherein the closed distal end comprises a plug.

* * * * *